United States Patent
Shewmaker et al.

(10) Patent No.: US 6,653,530 B1
(45) Date of Patent: *Nov. 25, 2003

(54) METHODS FOR PRODUCING CAROTENOID COMPOUNDS, TOCOPHEROL COMPOUNDS, AND SPECIALTY OILS IN PLANT SEEDS

(75) Inventors: Christine K. Shewmaker, Woodland, CA (US); B. Ganesh Bhat, St. Louis, MO (US); Mylavaraapu Venkatramesh, St. Louis, MO (US); Shaukat H. Rangwala, Ballwin, MO (US); Ganesh M. Kishore, Creve Coeur, MO (US); Sekhar S. Boddupalli, Manchester, MO (US)

(73) Assignee: Calgene LLC, Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/023,587

(22) Filed: Feb. 13, 1998

(51) Int. Cl.$^7$ .............. A01H 5/00; A01H 5/10; C12N 15/31; C12N 15/82
(52) U.S. Cl. .......... 800/282; 800/286; 800/287; 800/288; 800/298; 800/306; 800/310; 800/312; 800/313; 800/314; 800/320; 800/320.1; 800/320.2; 800/320.3; 800/322; 800/281
(58) Field of Search .............. 800/278, 282, 800/285, 287, 290, 295, 300.1, 305, 306, 308, 310, 312, 313, 314, 317–320.3, 322, 286, 281, 288, 298; 435/410, 419

(56) References Cited

U.S. PATENT DOCUMENTS

| | | | |
|---|---|---|---|
| 4,727,219 A | 2/1988 | Brar et al. | |
| 5,304,478 A | 4/1994 | Bird et al. | |
| 5,429,939 A | 7/1995 | Misawa et al. | |
| 5,432,069 A | 7/1995 | Gruninger et al. | |
| 5,618,988 A | * 4/1997 | Hauptmann et al. | 800/205 |
| 5,684,238 A | 11/1997 | Ausich et al. | |
| 5,750,865 A | 5/1998 | Bird et al. | |
| 5,792,903 A | 8/1998 | Hirschberg et al. | |
| 6,429,356 B1 | 8/2002 | Shewmaker | |
| 2002/0092039 A1 | 7/2002 | Shewmaker et al. | |

FOREIGN PATENT DOCUMENTS

| | | |
|---|---|---|
| WO | 91/02059 | 2/1991 |
| WO | 91/09128 | 6/1991 |
| WO | 91/13078 | 9/1991 |
| WO | 93/18158 | 9/1993 |
| WO | 94/11516 | 5/1994 |
| WO | 94/12014 | 6/1994 |
| WO | 94/18337 | 8/1994 |
| WO | 95/06128 A2 | 3/1995 |
| WO | 95/06128 A3 | 3/1995 |
| WO | 95/08914 | 4/1995 |
| WO | 95/18220 | 7/1995 |
| WO | 95/23863 | 9/1995 |
| WO | 95/34668 | 12/1995 |
| WO | 96/02650 A2 | 2/1996 |
| WO | 96/02650 A3 | 2/1996 |
| WO | 96/06172 | 2/1996 |
| WO | 96/13149 | 5/1996 |
| WO | 96/13159 | 5/1996 |
| WO | 96/36717 A2 | 11/1996 |
| WO | 96/36717 A3 | 11/1996 |
| WO | 97/17447 | 5/1997 |
| WO | WO 97/27285 | 7/1997 |
| WO | 98/06862 | 2/1998 |
| WO | 98/18910 | 5/1998 |
| WO | 99/07867 | 2/1999 |
| WO | 99/55889 | 11/1999 |
| WO | 01/088169 | 11/2001 |

OTHER PUBLICATIONS

Misawa, N. et al., "Expression of an Erwinia phytoene desaturase gene not only confers multiple resistance to herbicides interfering with cartenoid biosynthesis . . . " 1994, The Plant Journal, vol. 6, pp. 481–489.*

Verwoert, I. et al., "Developmental specific expression and organelle targeting of the *Escherichia coli* fabD gene, encoding malonyl coenzyme A–acyl carrier protein transacylase . . . " 1994, Plant Molecular Biology, vol. 26, pp. 189–202.*

Smith, C. J. S. et al., "Antisense RNA inhibition of polygalacturonase gene expression in transgenic tomatoes." 1988, Nature, vol. 334, pp. 724–726.*

De luca, V. "Molecular characterization of secondary metabolic pathways." 1993, AgBiotech News and Information, vol. 5, pp. 225N–229N.*

Sandler et al. Inhibition of gene expression in transformed plants by antisense RNA. Plant Molecular Biology, 1988, vol. 11, No. 3, pp. 301–310.*

Bentley, et al., "The shikimate pathway—a metabolic tree with many branches" *Critical Reviews in Biochemistry and Molecular Biology* 25(5), 307–384 (1990).

Garcia, et al., "Subcellular localization and purification of a p–hydroxyphenylpyruvate dioxygenase from cultured carrot cells and characterization of the corresponding cDNA" *Biochemical Journal* 325, 761–769 (1997).

Fuqua, et al., "Characterization of melA: a gene encoding melanin biosynthesis from the marine bacterium *Shewanella colwelliana*" *Gene* 109, 131–136 (1991).

(List continued on next page.)

Primary Examiner—David T. Fox
Assistant Examiner—Cynthia Collins
(74) Attorney, Agent, or Firm—Grace L. Bonner; Brian K. Stierwalt; Arnold & Porter

(57) ABSTRACT

Methods are provided for producing plants and seeds having altered carotenoid, fatty acid and tocopherol compositions. The methods find particular use in increasing the carotenoid and tocopherol levels in oilseed plants, and in providing desirable high oleic acid seed oils.

52 Claims, 27 Drawing Sheets

OTHER PUBLICATIONS

Herrmann, et al., "The shikimate pathway as an entry to aromatic secondary metabolism" *Plant Physiology* 107, 7–12 (1995).

d'Harlingue, et al., "Plastid enzymes of terpenoid biosynthesis" *The Journal of Biological Chemistry* 260(28), 15200–15203 (1985).

Kishore, et al., "Amino acid biosynthesis inhibitors as herbicides" *Annual Review of Biochemistry* 57, 627–663 (1988).

Soll, et al., "Hydrogenation of geranylgeraniol" *Plant Physiology* 71, 849–854 (1983).

Fiedler, et al., "The formation of homogentisate in the biosynthesis of tocopherol and plastoquinone in spinach chloroplasts" *Planta* 155, 511–515 (1982).

Soll, et al., "Tocopherol and plastoquinone synthesis in spinach chloroplasts subfractions" *Archives of Biochemistry and Biophysics* 204(2), 544–550 (1980).

Marshall, et al., "Biosynthesis of tocopherols: a re–examination of the biosynthesis and metabolism of 2–methyl–6–phytyl–1,4–benzoquinol" *Phytochemistry* 24(8), 1705–1711 (1985).

Yamamoto, E., "Purification and metal requirements of 3–dehydroquinate synthase from *Phaseolus mungo* seedlings" *Phytochemistry* 19, 779–781 (1980).

Chaudhuri, et al., "The purification of shikimate dehydrogenase from *Escherichia coli*" *Biochemical Journal* 226, 217–223 (1985).

Singh, et al., "Chorismate mutase isoenzymes from *Sorghum bicolor*: purification and properties" *Archives of Biochemistry and Biophysics* 243(2), 374–384 (1985).

Stocker, et al., "The substrate specificity of tocopherol cyclase" *Bioorganic and Medicinal Chemistry* 4(7), 1129–1134 (1996).

Shigeoka, et al., "Isolation and properties of γ–tocopherol methyltransferase in *Euglena gracilis*" *Biochimica et Biophysica Acta* 1128, 220–226 (1992).

Furuya, et al., "Production of tocopherols by cell culture of safflower" *Phytochemistry* 26(10), 2741–2747 (1987).

Ruzafa, et al., "The protein encoded by the *Shewanella colwelliana melA* gene is a p–hydroxyphenylpyruvate dioxygenase" *FEMS Microbiology Letters* 124, 179–184 (1994).

d'Amato, et al., "Subcellular localization of chorismate–mutase isoenzymes in protoplasts from mesophyll and suspension–cultured cells of *Nicotiana silvestris*" *Planta* 162, 104–108 (1984).

Goers, et al., "Separation and characterization of two chorismate–mutase isoenzymes from *Nicotiana silvestris*" *Planta* 162, 109–116 (1984).

Norris, et al., "Genetic dissection of carotenoid synthesis in Arabidopsis defines plastoquinone as an essential component of phytoene desaturation" *The Plant Cell* 7, 2139–2149 (1995).

Keller, et al., "Metabolic compartmentation of plastid prenyllipid biosynthesis; Evidence for the involvement of a multifunctional geranylgeranyl reductase" *European Journal of Biochemistry* 251, 413–417 (1998).

Addlesee, et al., "Cloning, sequencing and functional assignment of the chlorophyll biosynthesis gene, chlP, of *Synechocystis* sp. PCC 6803" *FEBS Letters* 389, 126–130 (1996).

Peisker, et al., "Phytol and the breakdown of chlorophyll in senescent leaves" *Journal of Plant Physiology* 135, 428–432 (1989).

Zaka, et al., "Changes in carotenoids and tocopherols during maturation of Cassia seeds" *Pakistan Journal of Scientific and Industrial Research* 30(11), 812–814 (1987).

International Search Report, PCT/US 01/15264, WO 01/088169 A3, May 8, 2002, pp. 1–2.

International Search Report, PCT/US 98/16466, Dec. 8, 1998, pp. 1–3.

International Search Report, PCT/US 97/14035, Jan. 15, 1998, pp. 1–3.

C. Bayley, et al, "Engineering 2,4–D resistance into cotton," *Theor Appl Genet* 83:645–649 (1992).

P. Beyer, "Phytoene–forming activities in wild–type and transformed rice endosperm," *IRRN* 21:2–3 (Aug.–Dec. 1996).

P. Bramley, et al, "Biochemical characterization of transgenic tomato plants in which carotenoid synthesis has been inhibited through the expression of antisense RNA to pTOM5," *The Plant Journal* 2(3): 343–349 (1992).

J. Breitenbach, et al, "Expression in *Escherichia coli* and properties of the carotene ketolase from *Haematococcus pluvialis*," *FEMS Microbiology Letters* 140: 241–46 (1996).

B. Buckner, et al, "The y1 Gene of Maize Codes for Phytoene Synthase," *Genetics* 143: 479–488 (May 1996).

P. Burkhardt, et al, "Genetic Engineering of Provitamin A Biosynthesis in Rice Endosperm," *Experientia*, S08–07.

P. K. Burkhardt, et al, "Transgenic rice (*Oryza sativa*) endosperm expressing daffodil (*Narcissus pseudonarcissus*) phytoene synthase accumulates phytoene, a key intermediate of provitamin A biosynthesis" *The Plant Journal* 11(5): 1071–1078 (1997).

K. Duncan, et al, "The overexpression and complete amino acid sequence of *Excherichia coli* 3–dehydroquinase," *Biochem. J.* 238: 475–483 (1986).

M. L. Ericson, et al, "Analysis of the promoter region of napin genes from *Brassica napus* demonstsrates binding of nuclear protein in vitro to a conserved sequence motif," *Eur. J. Biochem.* 197: 741–746 (1991).

V. S. Fedenko, et al, Abstract: RU 2005353, Derwent Accession No.: 1994–253787.

P. D. Fraser, et al, "Enzymic confirmation of reactions involved in routes to astaxanthin formation, elucidated using a direct substrate in vitro assay," *Eur. J. Biochem.* 252: 229–236 (1998).

P P. D. Fraser, et al, "In Vitro Characterization of Astaxanthin Biosynthetic Enzymes," *The Journal of Biological Chemistry* 272(10) 6128–6135 (Mar. 7, 1997).

R. G. Fray, et al, "Identification and genetic analysis of normal and mutant phytoene synthase genes of tomato by sequencing, complementation and co–suppression," *Plant Molecular Biology* 22: 589–602 (1993).

R. G. Fray, et al, Constitutive expression of a fruit phytoene synthase gene in transgenic tomatoes causes dwarfism by redirecting metabolites from the gibberellin pathway,*The Plant Journal* 8(5): 693–701 (1995).

M. Harker, et al, "Biosynthesis of ketocarotenoids in transgenic cyanobacteria expressing the algal gene for β–C–4–oxygenase, crtO," *FEBS Letters* 404: 129–134 (1997).

S. Kajiwara, et al, "Isolation and functional identification of a novel cDNA for astaxanthin biosynthesis from *Haematococcus pluvialis*, and astaxanthin synthesis in *Escherichia coli*," *Plant Molecular Biology 29*: 343–352 (1995).

M. H. Kumagai, et al, "Cytoplasmic inhibition of carotenoid biosynthesis with virus–derived RNA," *Proc. Natl. Acad. Sci. USA 92*: 1679–1683, (Feb. 1995).

T. Lotan, et al, "Cloning and expression in *Escherichia coli* of the gene encoding β–C–4–oxygenase, that converts β–carotene to the ketocarotenoid canthaxanthin in *Haematococcus pluvialis*," *FEBS Letters 364*: 125–128 (1995).

N. Misawa, et al, "Elucidation of the *Erwinia uredovora* Carotenoid Biosynthetic Pathway by Functional Analysis of Gene Products Expressed in *Escherichia coli*," *Journal of Bacteriology* 6704–6712 (Dec. 1990).

N. Misawa, et al, "Functional expression of the *Erwinia uredovora* carotenoid biosynthesis gene crtI in transgenic plants showing an increase of β–carotene biosynthesis activity and resistance to the bleaching herbicide norflurazon," *The Plant Journal 4*(5): 833–840 (1993).

N. Misawa, et al, "Structure and Functional Analysis of a Marine Bacterial Carotenoid Biosynthesis Gene Cluster and Astaxanthin Biosynthetic Pathway Proposed at the Gene Level," *Journal of Bacteriology 177*(22): 6575–6584 (Nov. 1995).

C. Napoli, et al, "Introduction of a Chimeric Chalcone Synthase Gene into Petunia Results in Reversible Co–Suppression of Homologous Genes in trans," *The Plant Cell.2*: 279–289, (Apr. 1990).

S. R. Norris, et al, "Genetic Dissection of Carotenoid Synthesis in Arabidopsis Defines Plastoquinone as an Essential Component of Phytoene Desaturation," *The Plant Cell 7*: 2139–2149 (Dec. 1995).

S. R. Norris, et al, "Complementation of the Arabidopsis pds1 Mutation with the Gene Encoding p–Hydroxyphenylpyruvate Dioxygenase," *Plant Physiol. 117*: 1317–1323 (1998).

A. Oommen, et al, "The Elicitor–Inducible Alfalfa Isoflavone Reductase Promotor Confers Different Patterns of Developmental Expression in Homologous and Heterologous Transgenic Plants," *The Plant Cell 6*: 1789–1803, (Dec. 1994).

D. L. Pompliano, et al, "Probing Lethal Metabolic Perturbations in Plants with Chemical Inhibition of Dehydroquinate Synthase," *J. Am. Chem. Soc.111*: 1866–1871 (1989).

Raven, et al, eds., Biology of Plants, Worth publs, 5th edition, 629–30 (1992).

S. Römer, et al, "Expression of the Genes Encoding the Early Carotenoid Biosynthetic Enzymes in *Capsicum annuum*," *Biochemical and Biophysical Research Communications 196*(3): 1414–1421 (Nov. 15, 1993).

G. Sandmann, et al, "New functional assignment of the carotenogenic genes crtB and crtE with constructs of these genes from Erwinia species," *FEMS Microbiology Letters 90*: 253–258 (1992).

C. K. Shewmaker, et al, "Seed–specific overexpression of phytoene synthase: increase in carotenoids and other metabolic effects," *The Plant Journal 20*(4): 401–412 (1999).

C.J.S. Smith, et al, "Antisense RNA inhibition of polygalacturonase gene expression in transgenic tomatoes," *Nature 334*: 724–726 (Aug. 25, 1998).

Z. Sun, et al, "Cloning and Functional Analysis of the β–Carotene Hydroxylase of *Arabidopsis thaliana*," *The Journal of Biological Chemistry 271*(40): 24349–24352 (Oct. 4, 1996).

J. A. Suzich, et al, "3–Deoxy–D–arabino–Heptulosonate 7–Phosphate Synthase from Carrot Root (*Daucus carota*) Is a Hysteretic Enzyme," *Plant Physiol. 79*: 765–770 (1985).

X. Zhu, et al, "Cloning and Functional Expression of a Novel Geranylgeranyl Pyrophosphate Synthase Gene from *Arabidopsis thaliana* in *Escherichia coli*," *Plant Cell Physiol.* 38(3): 357–361 (1997).

* cited by examiner

```
BglII
AGATCTGCTA GAGAGCTTTG CAATTCATAC AGAAGTGAGA AAAATGGCTT CTATGATATC      60
CTCTTCCGCT GTGACAACAG TCAGCCGTGC CTCTAGGGGG CAATCCGCCG CAGTGGCTCC     120
ATTCGGCGGC CTCAAATCCA TGACTGGATT CCCAGTGAAG AAGGTCAACA CTGACATTAC     180
TTCCATTACA AGCAATGGTG GAAGAGTAAA GTGCATGAAT AATCCGTCGT TACTCAATCA     240
TGCGGTCGAA ACGATGGCAG TTGGCTCGAA AAGTTTTGCG ACAGCCTCAA AGTTATTTGA     300
TGCAAAAACC CGGCGCAGCG TACTGATGCT CTACGCCTGG TGCCGCCATT GTGACGATGT     360
TATTGACGAT CAGACGCTGG GCTTTCAGGC CCGGCAGCCT GCCTTACAAA CGCCCGAACA     420
ACGTCTGATG CAACTTGAGA TGAAAACGCG CCAGGCCTAT GCAGGATCGC AGATGCACGA     480
ACCGGCGTTT GCGGCTTTTC AGGAAGTGGC TATGGCTCAT GATATCGCCC CGGCTTACGC     540
GTTTGATCAT CTGGAAGGCT TCGCCATGGA TGTACGCGAA GCGCAATACA GCCAACTGGA     600
TGATACGCTG CGCTATTGCT ATCACGTTGC AGGCGTTGTC GGCTTGATGA TGGCGCAAAT     660
```

FIG. 1A

| | | | | |
|---|---|---|---|---|
| CATGGGCGTG | CGGGATAACG | CCACGCTGGA | CCGCGCCTGT | GACCTTGGGC | TGGCATTTCA | 720 |
| GTTGACCAAT | ATTGCTCGCG | ATATTGTGGA | CGATGCGCAT | GCGGGCCGCT | GTTATCTGCC | 780 |
| GGCAAGCTGG | CTGGAGCATG | AAGGTCTGAA | CAAAGAGAAT | TATGCGGCAC | CTGAAAACCG | 840 |
| TCAGGCGCTG | AGCCGTATCG | CCCGTCGTTT | GGTGCAGGAA | GCAGAACCTT | ACTATTTGTC | 900 |
| TGCCACAGCC | GGCCTGGCAG | GGTTGCCCCT | GCGTTCCGCC | TGGGCAATCG | CTACGGCGAA | 960 |
| GCAGGTTTAC | CGGAAAATAG | GTGTCAAAGT | TGAACAGGCC | GGTCAGCAAG | CCTGGGATCA | 1020 |
| GCGGCAGTCA | ACGACCACGC | CCGAAAAATT | AACGCTGCTG | CTGGCCCGCT | CTGGTCAGGC | 1080 |
| CCTTACTTCC | CGGATGCGGG | CTCATCCTCC | CCGCCCTGCG | CATCTCTGGC | AGCGCCCGCT | 1140 |
| CTAGCGCCAT | GTCTTTCCCG | GAGCGTCCGA | ATTATCGATG | AATTCGAGCT | CGGTACCCGG | 1200 |

BamHI
GGATCCTCTA GAGTCGACCT GCAGGCATGC AA         1232

FIG. 1B

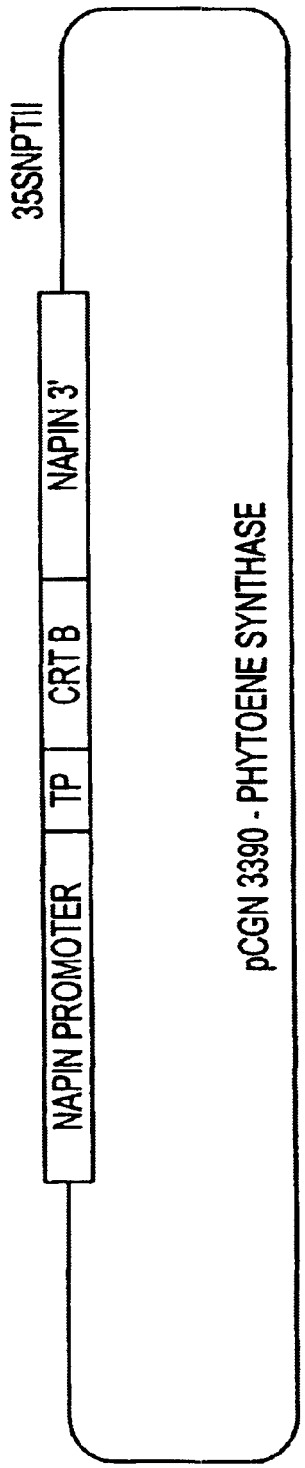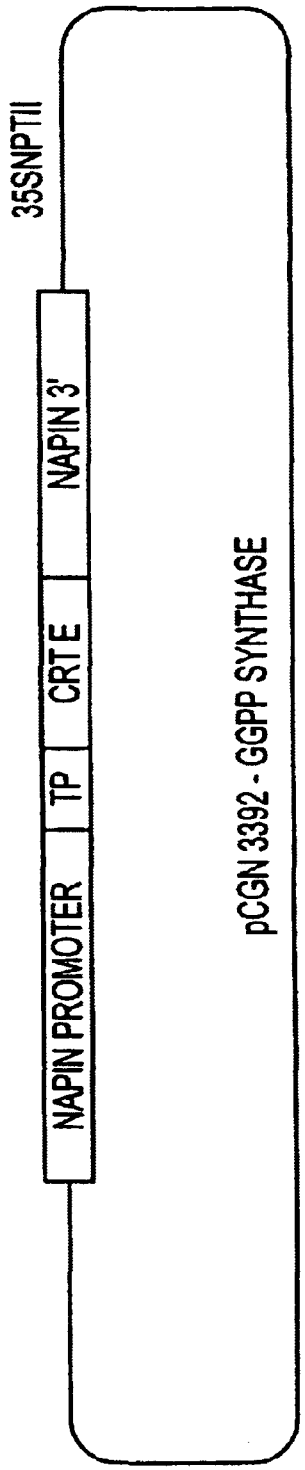
FIG. 2A
FIG. 2B

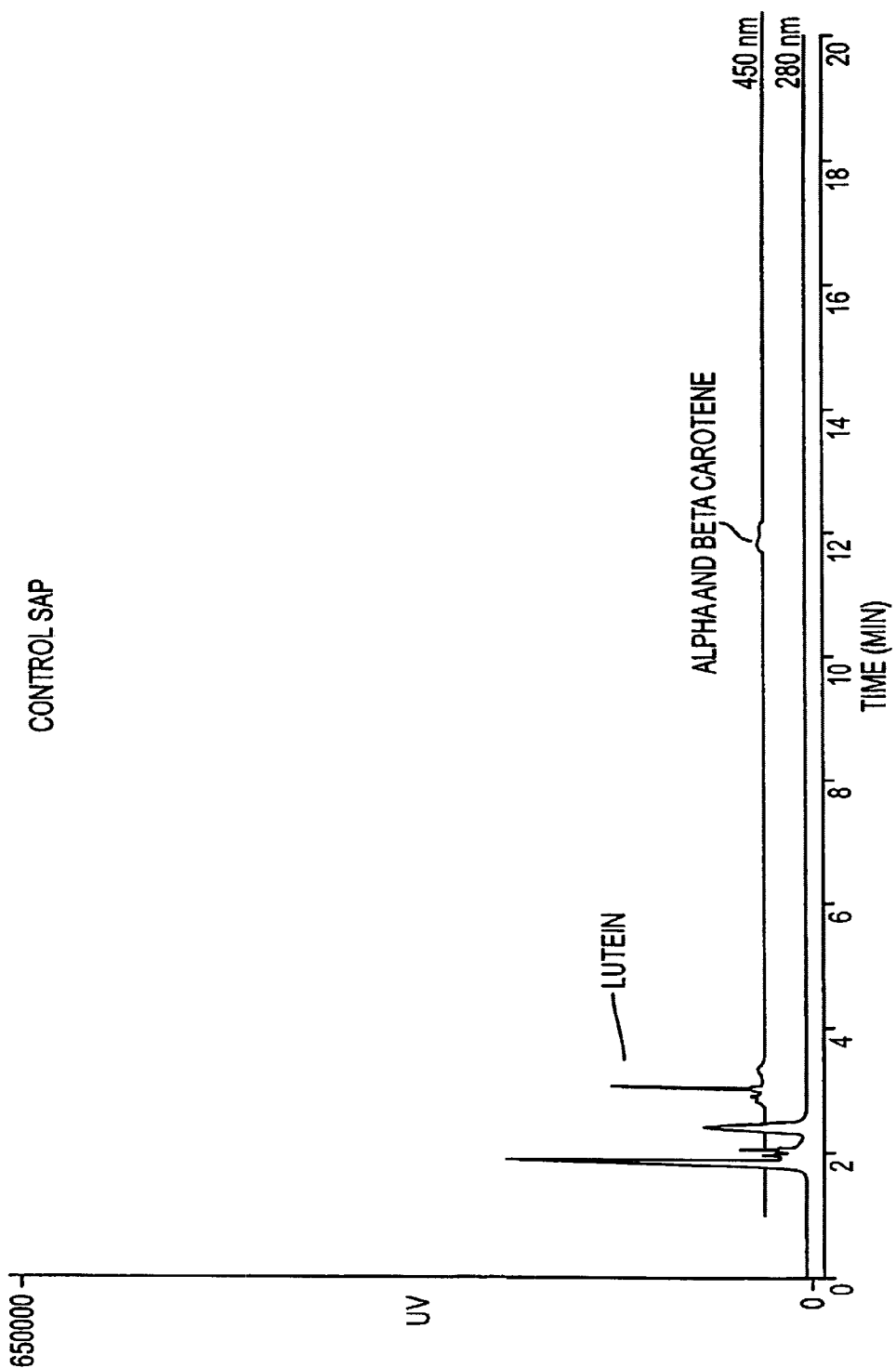

```
              >AluI       >AluI                    >HaeIII |
                |           |                         |    |
              * |    500    |       *         520     |  * |    540
                *           *                         *    *
       CTTCTGGAGCAGCTTCTGGGAAGCTCTTGCAATACGAAGTTGGAGGGCCTAGAGTCTGTG

>HinfI      >Sau3AI
                                         |            |
                       *    560     *         580     |   *          600
                            *            *        | *   | *            *
       TCCAAACTGCTTACGGCTTGGAGGTTGAGGTGGAAAAGAGTCCATATGATCCAGAGCAGA >AluI
                                                   |
                                         >MspI    |     >AluI
                                           |      |       |
                   *    620        *     640|     |       |    660
                        *                   *|            *    *
       TGGTGTTCATGGATTACAGAGATTATACAAACGAGAAAATCCGGAGCTTAGAAGCTGAAT >HinfI
                                              |
                       *    680        *     700        *         720
                            *                 *                    *
       ATCCAACGTTTCTCTACGCCATGCCTATGACAAAGACCAGAGTCTTCTTTGAGGAGACAT >AluI
                                                      |
                       *    740        *      760     |   *      780
                            *                  *      |           *
       GTCTTGCTTCAAAAGATGTCATGCCCTTTGATTTGCTTAAAAAGAAGCTCTTGTTGAGAT >HinfI
           |
           |     *    800        *      820        *         840
           |          *                  *                    *
       TAGAGACACTCGGAATCCGAATACTAAAGACTTACGAAGAGGAATGGTCTTATATCCCAG >AluI
                                                                |
                            >HinfI                           >PstI
                              |                                ||
                       *    860      *  |   880       *        || 900
                            *              *                   ||  *
       TAGGTGGTTCCTTGCCAAACACGGAACAAAAGAATCTCGCCTTTGGCGCTGCAGCTAGCA >SpeI   >BamHI
                                                         |        |
                       >EcoRI    >BstXI   >HaeIII |    >Sau3AI
                         |         |        |    |       |
                       * |   920   |  *     | 940 |      | *    960
                         *         |  *     |  *  |      |        *
       TGGTACATCCCGCAACAGAAGCCGAATTCCAGCACACTGGCGGCCGTTACTAGTGGATCC
       GA
```

FIG. 9B

```
                                                               >EcoRI
                                                               >PstI
         >HinfI                    >XhoI
                    >HaeIII  >XbaI >SphI   >HaeIII >BstXI >EcoRV
    10        20        30        40        50        60        70        80        90       100       110       120
    *         *         *         *         *         *         *         *         *         *         *         *
GTGAATTGTA ATACGACTCA CTATAGGGCG AATTGGGCCCT TCTAGATGCA TGCTCGAGCG GCCGCCAGTG TGATGGATAT CTGCAGAATT CGGCTTGTGTT GTGGTCCTGC TGGTTTAGCC
                                                                                                    >Sau3AI
>BglI >HinfI                                                                                >HincII
   130       140       150       160       170       180       190       200       210       220   >SalI 230       240
    *         *         *         *         *         *         *         *         *         *         *         *
TTGGCGGCTG AATCAGCTAA GTTAGGACTT AAAGTTGGAC TGATTGGTCC TGACCTTCCT TTCACTAACA ACTACGGTGT TTGGAAGAGAT GAGTTCAACG ATCTTGGCTT GCAAAAATGT >HaeIII
   250       260       270       280       290       300       310       320       330       340       350       360
    *         *         *         *         *         *         *         *         *         *         *         *
ATTGAGCATG TTTGGAGAGA TACCCTTGTG ATGACAATCC TATTACCATT GGTCGTGCTT ATGGAAGAGT TAGTCGACGT TTACTTCACG AGGAGTTCTT GAGGAGTGT >AluI                       >AluI   >HaeIII
>HinfI                                                     >HinfI
   370       380       390       400       410       420       430       440       450       460       470       480
    *         *         *         *         *         *         *         *         *         *         *         *
GTGGAGTCAG GTGTCTCGTA TCTTAGCTCC AAAGTTGAGA GCATAACAGA AGCTCCTGAT GGCCTTAGGC TTGTTTCCTG TGAACAAAAC ACCCCTTGTTC CGTGCAGGCT TGCCACTGTT >AluI                                      >HinfI  >Sau3AI
              >AluI         >AluI
   490       500       510       520       530       540       550       560       570       580       590       600
    *         *         *         *         *         *         *         *         *         *         *         *
GCTTCTGGAG CAGCTTCTTG GAAGCTCTG CAATACGAAG TTGGAGGGCC TAGAGTCTGT GTCCAAACTG CTTACGGCTT GGAGGTTGAG GTGGAAAAGA GTCCATATGA TCCAGAGCAG >HinfI
                            >MspI           >AluI
   610       620       630       640       650       660       670       680       690       700       710       720
    *         *         *         *         *         *         *         *         *         *         *         *
ATGGTGTTCA TGGATTACAG AGATTATACA AACGAGAAAA TCCCGGAGCTT AGAAGCTGAA TATCCAACGT TTCTCTACGC CATGCCTATG ACAAAGACCA GAGTCTTCTT TGAGGAGACA
```

FIG. 10A

```
                                                                                              >AluI     >HinfI
        730        740        750        760        770        780        790        800        810        820        830        840
         *          *          *          *          *          *          *          *          *          *          *          *
TGTCTTGCTT CAAAAGATGT CATGCCCTTT GATTTGCTTA AAAAGAAGCT CTTGTGTGAGA TTAGAGACAC TCGGAATCCG AATACTAAAG ACTTACGAAG AGGAATGGTC TTATATCCCA
                                                                                                              >BglII
                                                    >AluI                                                     >Sau3AI                      >AluI
        850        860        870        880        890        900        910        920        930        940        950        960
         *          *          *          *          *          *          *          *          *          *          *          *
GTAGGTGGTT CCTTGCCAAA CACGGAACAA AAGAATCCG TGCAGCTAGC ATGGTTCATC CTGCAACAGG CTATTCAGTT GTGAGATCTT TGTCTGAAGC TCCAAAATAC
                              >HinfI        >PstI
                                                                                                   >AluI
                                                                                                   >HindIII                            >HaeIII
        970        980        990        1000       1010       1020       1030       1040       1050       1060       1070       1080
         *          *          *          *          *          *          *          *          *          *          *          *
GCATCAGTCA TCGCTAATAT ACTAAAACAT GAGACCACTA CTTCCTTCAC CAGACACATC AACACCAATA TTTCAAGACA AGCTTGGGAT ACTTATGGC CACCAGAAAG GAAACGACAG
                                                                                                  >AluI
                 >EcoRI   >BstXI   >HaeIII       >SpeI   >BamHI   >Sau3AI           >AluI           >SacI >HindIII  >KpnI                      >AluI
        1090       1100       1110       1120       1130       1140       1150       1160       1170       1180       1190       1200
         *          *          *          *          *          *          *          *          *          *          *          *
AGAGCATTCT TTCTAAGCCG AATTCCAGCA CACTGGCGGC CGTTACTAGT GGATCCGAGC TCGGTACCAA GCTTGGCGTA ATCATGGTCA TAGCTGTTTC CTGTGTGAAA TTGTTATCCG
              >MspI
        1210       1220       1230       1240       1250       1260       1270
         *          *          *          *          *          *          *
CTCACAATTC CACACAACAT ACGAGCCGGA AGCATAAAGT GTAAAGCCTG GGGTGCCTAA TGAGTGAGCT AA
```

FIG. 10B

```
GAGCTCGGAT CCACTAGTAA CGGCCGCCAG TGTGCTGGAA TTCGGCTTCT ATCTTGTACC
                                                                60
                                                                 *
AAATTGTTGA TCATCTTAGC AAGAGGAACA GTTCCCTTCG TCATGATCTC CAACCTCGAG
                                                               120
                                                                 *
GTATTAGAAG CATGGCGAGAA GAGCGACAGC CCGAAGAACA CCAGGTCCGG GAGAAACAGC
                                                               180
                                                                 *
CTCGACGACA AGAAACCATG CCAGTAACGC GGTTCCAGGT CAAAGAACGC ATCAAAGAAC
                                                               240
                                                                 *
CTCCTAGTAG CATCCAAATC AAGCTTCAGC AAAATATCCA TCCCAAAACA GAAGAACTCC
                                                               300
                                                                 *
CTCTGTCTCC GCCTCTCAAT AGGCCACAAG TCTCTCCACA CCTCAGCCGA GAGCTCATCT
                                                               360
                                                                 *
CCTCTCAAGC CGTTGTTGTT ACCACCACCA AGTACCGGCA CTATAGCGTT TGCAACTATC
                                                               420
                                                                 *
GGAGCAGCTG CAAGAGTCCT AGCAACCATG TAACCAGTCG AAGGATGAAC CATCCCCGCC
                                                               480
                                                                 *
```

FIG. 11A

```
GTACCGCCAA TGCCAACAAC TCTTTGAGGC AAGACCGGTA AAGGACCTCC CATAGGGATC     540

ACACAACGCT CGTCTTCCTC AATCCGCTTC ACGTTGATCC CCAAATGTTT CAGCCTCGCA     600

ACCATCCTCT CTTGGATATC TTCCATCTTC AGACCCGGCC TAGCCACAAG AGACGTCTCT     660

TCAAGAAAGA TCCTGTTGGA AGAAAACGGC ATCGCGTACA GGAACGTAGG GATCTTGCTG     720

TTCCGCTCTT TAACCTCAGG GTACGGCGTCA AGATGCTTAT CTCTCCAGTC CATGAACACC     780

ATCTTATCCA CATCAAACGG GTGACCATCG ACCTCAGCAA TGATACCATA AGCTACTTGA     840

TACCCAGGGT TATAAGGCTT ATCATACTGA ACCAAGCATC TTGAAAAACC AGTAGCGTCG     900

AGAACAACAG AAGCCTGAAT CTTCACACCG TCACTGCAGA CAACAGTGGA GTTAACCTCC     960
```

FIG. 11B

TCGTGAACCA CGTCAGTGAC TTTAGCCTGA TGGAATCTAA CACCGTTGGT GATGCACTTC 1020
TGAAGCATCT TGGATTTGAG CTGTTTACGG TTCACTCTCC CGTAAGGCCG GGACAGGTCC 1080
TTTTCGGAGC CGTCGTTGAT GTAGACGACG GCGCCGGACC AGGTGGGTGTC GAGGCAGTCT 1140
AGCAAGTCCA CTCGTCAACC CAAACTCCGT AGTTGTTAGG CCAAATGAGT 1200
TTGGGGGAAG GATCGATGGA GCAGACAGAG AGTCCAGCTT CGGAGACTTG CTGAGCCACG 1260
GCTAAACCAG CGGGGCCGCC GCCAACGATA GCTAGATCAA CAACTTTGTT CAGGGAAGTG 1320
TCGTTTAAAG GAAGGTCCAA GTCGAGATTC TCCTTCTTGG TTTCAGGAAC AAGATCCAAA 1380
AGAGCACTAC TAGCACTAGT GATACTACTA CCGATTCTGA TTGCTCTTTT CTTCAAACCA 1440

FIG. 11C

```
AGCTTAACCC TTGAAGGATT TGGACTTAAT CTCTCGAACC CATGAAACTG AGGGATGAAA
                                                              1500
                                                               *
AACTCGAGCT TGTTGGGTGT TTTCAACAGA GTATCCATCG AATTCTGCAG ATATCCATCA
                                                              1560
                                                               *
CACTGGGCGGC CGCTCGAGCA TGCATCTAGA
```

FIG. 11D

| Sample ID # | Segregation ratio | Carotenoid concentration (μg/gFW) | | | | |
|---|---|---|---|---|---|---|
| | | Lutein | Lycopene | α-Carotene | β-Carotene | Total |
| SP30021 control 1 | | 24.4 | ND | ND | 1.9 | 26.3 |
| SP30021 control 2 | | 34.0 | ND | ND | 4.9 | 38.9 |
| T2 3390-SP30021-1 | 3:1 | 33.5 | 6.1 | 229.0 | 385.7 | 654.3 |
| T2 3390-SP30021-2 | 15:1 | 50.4 | 6.2 | 372.4 | 721.4 | 1150.4 |
| T2 3390-SP30021-3 | no fit | 45.8 | 3.9 | 352.9 | 580.9 | 983.5 |
| T2 3390-SP30021-4 | 3:1 | 31.0 | 4.9 | 306.1 | 463.3 | 805.3 |
| T2 3390-SP30021-5 | 3:1 | 36.8 | 10.5 | 370.6 | 659.4 | 1077.3* |
| T2 3390-SP30021-6 | 15:1 | 46.9 | 9.1 | 445.1 | 797.0 | 1298.1 |
| T2 3390-SP30021-7 | 15:1 | 51.2 | 7.4 | 494.9 | 941.4 | 1494.9 |
| T2 3390-SP30021-8 | 15:1 | 41.9 | 11.3 | 468.4 | 904.3 | 1425.9 |
| T2 3390-SP30021-9 | no fit | 68.4 | 11.9 | 394.2 | 949.2 | 1423.7 |
| T2 3390-SP30021-10 | >63:1 | 51.6 | ND | 12.6 | 22.8 | 87.0 |
| T2 3390-SP30021-11 | null | 52.2 | 9.5 | 409.8 | 714.5 | 1186.0* |
| T2 3390-SP30021-12* | 3:1 | 48.0 | 10.2 | 400.0 | 738.8 | 1197.0* |
| T2 3390-SP30021-13 | 3:1 | 66.1 | 3.9 | 98.0 | 216.0 | 384.1 |
| T2 3390-SP30021-14 | 3:1 | 49.1 | 8.9 | 320.0 | 611.6 | 989.6 |
| T2 3390-SP30021-15 | null | 27.0 | ND | ND | 1.2 | 28.2 |
| T2 3390-SP30021-16 | 3:1 | 55.6 | 6.4 | 283.1 | 527.4 | 872.5 |
| T2 3390-SP30021-17 | 3:1 | 53.0 | 9.1 | 324.9 | 614.3 | 1001.3 |
| T2 3390-SP30021-18 | >63:1 | 49.6 | 8.1 | 449.0 | 759.3 | 1266.0 |
| T2 3390-SP30021-19 | 3:1 | 62.2 | 7.6 | 346.0 | 613.2 | 1029.1 |
| T2 3390-SP30021-20 | 3:1 | 52.1 | 6.3 | 285.0 | 544.9 | 888.3 |
| T2 3390-SP30021-21 | 3:1 | 56.2 | 4.1 | 187.9 | 334.2 | 582.4 |
| T2 3390-SP30021-22 | null | 43.1 | ND | ND | 4.9 | 48.0 |
| T2 3390-SP30021-23 | 3:1 | 71.0 | 10.9 | 358.6 | 693.9 | 1134.4* |
| T2 3390-SP30021-24 | no fit | 53.9 | 7.3 | 272.1 | 520.4 | 853.7 |
| T2 3390-SP30021-25 | 3:1 | 31.9 | 12.2 | 309.1 | 580.9 | 934.1 |
| T2 3390-SP30021-26* | 3:1 | 34.3 | 9.3 | 311.2 | 584.4 | 939.2* |
| T2 3390-SP30021-27 | 3:1 | 52.6 | 9.8 | 299.8 | 686.3 | 1048.5 |

FIG. 12A

| | | | | | | |
|---|---|---|---|---|---|---|
| T2_3390-SP30021-28 | no fit | 68.4 | 10.0 | 446.3 | 907.7 | 1432.4 |
| T2_3390-SP30021-29 | >63:1 | 85.1 | 8.5 | 459.4 | 822.9 | 1375.9 |
| T2_3390-SP30021-30 | 3:1 | 63.7 | 5.8 | 356.9 | 598.4 | 1024.8 |
| T2_3390-SP30021-31 | 3:1 | 76.0 | 7.3 | 302.5 | 527.1 | 912.9 |
| T2_3390-SP30021-32 | null | 51.8 | 2.3 | 31.4 | 55.0 | 140.5 |
| T2_3390-SP30021-33 | 3:1 | 36.3 | 8.9 | 283.1 | 546.9 | 875.2 |
| T2_3390-SP30021-34 | >63:1 | 86.9 | 12.1 | 502.3 | 808.3 | 1409.6 |
| T2_3390-SP30021-35 | 3:1 | 39.3 | 8.1 | 224.5 | 461.0 | 732.9 |
| T2_3390-SP30021-36 | 15:1 | 55.5 | 11.0 | 538.5 | 829.9 | 1434.9 |
| T2_3390-SP30021-37* | 3:1 | 50.3 | 10.0 | 291.1 | 625.9 | 977.3* |
| T2_3390-SP30021-38 | 3:1 | 70.5 | 8.1 | 309.0 | 576.1 | 963.7 |
| T2_3390-SP30021-39 | null | 37.3 | ND | ND | 3.6 | 40.9 |
| T2_3390-SP30021-40 | 3:1 | 37.5 | 1.8 | 251.1 | 505.2 | 796.0 |
| T2_3390-SP30021-41 | 3:1 | 47.5 | 8.4 | 414.1 | 719.3 | 1189.3* |
| T2_3390-SP30021-42 | 3:1 | 42.6 | 5.1 | 230.3 | 352.9 | 630.9 |
| T2_3390-SP30021-43 | no fit | 83.3 | 5.6 | 128.4 | 219.8 | 437.9 |
| T2_3390-SP30021-46 | 3:1 | 21.6 | 1.4 | 211.2 | 368.3 | 602.5 |
| T2_3390-SP30021-47 | 3:1 | 79.1 | 3.7 | 312.5 | 570.5 | 965.8 |
| T2_3390-SP30021-48 | 3:1 | 45.3 | 3.0 | 225.2 | 401.5 | 675.0 |
| T2_3390-SP30021-49 | 15:1 | 28.3 | 1.6 | 346.0 | 677.2 | 1053.1 |
| T4_3390-SP001-1-6-13 | Homo | 52.4 | 1.5 | 439.5 | 669.3 | 1162.7 |

FIG. 12B

| Sample ID # | Segregation status | Lutein | Lycopene | α-Carotene | B-Carotene | Total |
|---|---|---|---|---|---|---|
| T3 3390-SP001-4-12 | Homo | 43.9 | 17.2 | 282.1 | 636.8 | 980.0 |
| T3 3390-SP001-5-7 | Het | 50.7 | 6.3 | 190.6 | 386.8 | 634.4 |
| T3 3390-SP001-5-12 | Homo | 45.5 | 19.5 | 255.9 | 633.4 | 954.3 |
| T3 3390-SP001-11-6 | Homo | 46.5 | 12.8 | 372.2 | 538.4 | 969.9 |
| T3 3390-SP001-11-9 | Homo | 54.0 | 10.2 | 406.0 | 556.0 | 1026.2 |
| T3 3390-SP001-14-2 | Homo | 59.7 | 12.5 | 342.4 | 764.0 | 1178.6 |
| T3 3390-SP001-14-6 | Homo | 66.3 | 12.9 | 431.0 | 673.9 | 1184.1 |
| T3 3390-SP001-15-9 | Homo | 30.8 | 14.3 | 271.8 | 559.8 | 876.7 |
| T3 3390-SP001-15-12 | Homo | 39.6 | 13.1 | 241.7 | 649.1 | 943.5 |
| T3 3390-SP001-16-3 | Homo | 49.9 | 17.1 | 230.2 | 519.7 | 816.9 |
| T3 3390-SP001-16-6 | Homo | 35.5 | 21.1 | 263.8 | 547.7 | 868.1 |
| T3 3390-SP001-35-2 | Het | 37.6 | 7.2 | 125.4 | 313.9 | 484.1 |
| T3 3390-SP001-35-10 | Homo | 43.7 | 16.6 | 234.7 | 503.9 | 798.9 |
| T3 3390-SP001-35-12 | Homo | 50.2 | 21.3 | 361.7 | 695.7 | 1128.9 |
| T3 3390-SP001-8-3 | Het | 41.4 | 9.9 | 178.2 | 434.4 | 663.9 |
| T3 3390-SP001-8-9 | Homo | 39.1 | 18.2 | 309.3 | 505.0 | 871.6 |
| T3 3390-SP001-8-11 | Homo | 35.9 | 19.6 | 260.7 | 580.4 | 896.6 |
| T3 3390-SP001-18-8 | Het | 29.2 | 12.2 | 112.1 | 247.6 | 441.1 |
| T3 3390-SP001-16-10 | Het | 38.0 | 14.6 | 248.2 | 486.3 | 787.1 |
| T4 3390-SP001-1-6-1 | Homo | 27.8 | 20.5 | 248.7 | 379.1 | 676.1 |
| T4 3390-SP001-1-6-8 | Homo | 38.5 | 16.8 | 304.1 | 383.9 | 743.3 |
| VAR SP001-4-5 | | 54.2 | ND | ND | 5.8 | 60.0 |
| VAR SP001-4-6 | | 51.2 | ND | ND | 7.0 | 58.2 |
| VAR SP001-4-10 | | 30.2 | ND | ND | ND | 30.2 |

FIG. 13

Carotenoid concentrations of canola seeds from T2 9002-SP30021 lines

| Sample ID | Segregation ratio | Carotenoid concentration (μg/gFW) | | | | | |
|---|---|---|---|---|---|---|---|
| | | Lutein | Lycopene | α-Carotene | β-Carotene | Phytoene | Total |
| SP30021 control | Homo | 21 | ND | ND | 2 | ND | 23 |
| 9002-SP30021-1* | 3:1 | 20 | 2 | 394 | 618 | 210 | 1244 |
| 9002-SP30021-2 | 3:1 | 17 | 2 | 285 | 537 | 128 | 969 |
| 9002-SP30021-3 | >64:1 | 19 | 7 | 489 | 689 | 381 | 1585 |
| 9002-SP30021-4 | 3:1 | 58 | 5 | 105 | 266 | 94 | 528 |
| 9002-SP30021-5 | 15:1 | 24 | 3 | 416 | 649 | 265 | 1357 |
| 9002-SP30021-6 | 3:1 | 13 | 2 | 324 | 546 | 176 | 1061 |
| 9002-SP30021-7 | 3:1 | 13 | 4 | 344 | 465 | 212 | 1038 |
| 9002-SP30021-8 | 15:1 | 12 | 3 | 449 | 690 | 224 | 1378 |
| 9002-SP30021-9 | >64:1 | 24 | 5 | 499 | 724 | 313 | 1565 |
| 9002-SP30021-10 | 15:1 | 52 | 25 | 387 | 505 | 245 | 1214 |
| 9002-SP30021-11 | 3:1 | 29 | 2 | 301 | 480 | 187 | 999 |
| 9002-SP30021-12 | >64:1 | 43 | 10 | 575 | 779 | 436 | 1843 |
| 9002-SP30021-13 | 3:1 | 19 | 3 | 357 | 509 | 279 | 1167 |
| 9002-SP30021-14 | null | 33 | ND | ND | 3 | ND | 36 |
| 9002-SP30021-15* | 3:1 | 29 | 7 | 472 | 599 | 354 | 1461 |
| 9002-SP30021-16 | 64:1 | 40 | 3 | 315 | 436 | 203 | 997 |
| 9002-SP30021-17 | 15:1 | 25 | 7 | 322 | 467 | 144 | 967 |
| 9002-SP30021-18 | >64:1 | 8 | 4 | 447 | 647 | 313 | 1419 |
| 9002-SP30021-19 | 15:1 | 38 | 17 | 537 | 570 | 327 | 1489 |
| 9002-SP30021-20* | 3:1 | 32 | 8 | 363 | 629 | 173 | 1205 |
| 9002-SP30021-21 | >64:1 | 1 | 6 | 468 | 736 | 348 | 1559 |
| 9002-SP30021-22 | 15:1 | 68 | 29 | 308 | 423 | 173 | 1001 |
| 9002-SP30021-23 | 15:1 | 51 | 20 | 449 | 553 | 423 | 1496 |
| 9002-SP30021-24 | 3:1 | 47 | 20 | 339 | 515 | 311 | 1232 |
| 9002-SP30021-25 | null | 27 | ND | ND | 2 | ND | 29 |
| 9002-SP30021-26* | 3:1 | 4 | 3 | 346 | 605 | 150 | 1108 |
| 9002-SP30021-27 | >64:1 | 25 | 5 | 416 | 698 | 376 | 1520 |
| 9002-SP30021-28 | 15:1 | 75 | 9 | 464 | 527 | 333 | 1408 |
| 9002-SP30021-29 | null | 32 | ND | 16 | 34 | ND | 82 |
| 9002-SP30021-30 | 3:1 | 25 | 9 | 316 | 525 | 182 | 1057 |
| 9002-SP30021-31 | null | 28 | ND | ND | 2 | ND | 30 |
| 9002-SP30021-32 | 3:1 | 29 | 5 | 198 | 283 | 132 | 647 |
| 9002-SP30021-33 | 15:1 | 50 | 40 | 408 | 557 | 324 | 1379 |
| 9002-SP30021-34 | 15:1 | 43 | 5 | 216 | 289 | 132 | 685 |
| 9002-SP30021-35 | 3:1 | 29 | 8 | 303 | 511 | 281 | 1132 |
| 9002-SP30021-36 | 3:1 | 26 | 9 | 324 | 402 | 157 | 918 |
| 9002-SP30021-37 | 3:1 | 34 | 11 | 263 | 418 | 143 | 869 |
| 9002-SP30021-39 | 15:1 | 54 | 13 | 219 | 420 | 118 | 824 |
| 9002-SP30021-40 | 15:1 | 30 | 7 | 382 | 716 | 235 | 1370 |
| 9002-SP30021-41 | 3:1 | 52 | 15 | 440 | 506 | 396 | 1409 |
| 9002-SP30021-42 | 3:1 | 49 | 20 | 317 | 516 | 170 | 1072 |
| 9002-SP30021-44 | >64:1 | 34 | 7 | 368 | 647 | 310 | 1366 |
| 9002-SP30021-45 | >64:1 | 45 | 9 | 429 | 636 | 402 | 1521 |
| 9002-SP30021-46 | 3:1 | 100 | 14 | 456 | 699 | 347 | 1617 |
| 9002-SP30021-48 | 3:1 | 37 | 5 | 191 | 354 | 231 | 818 |
| 9002-SP30021-50 | 64:1 | 51 | 22 | 522 | 756 | 303 | 1654 |

The transgenic lines with * signs were selected for further tests in advanced generations.

FIG. 14

```
   1 GAATTCGGCT CGAGGGCGGC GGCTGCGGGT GGCGGTGGTG GGAGGCGGCC
  51 CCGCCGGTGG CGCCGCGGCG GAGGCGCTGG CCAAGGGCGG CGTGGAGACG
 101 GTGCTGATCG AGCGGAAGAT GGACAACTGC AAGCCCTGCG GCGGCGCTAT
 151 CCCGCTGTGC ATGGTGTCGG AGTTCGACCT GCCGCTCGAC CTCGTGGACC
 201 GCAAGGTGAG GAAGATGAAG ATGATTTCGC CGTCCAACGT CGCCGTCGAC
 251 ATCGGCCGCA CGCTCGCGCC CCACGAGTAC ATCGGGATGG TCAGGCGCGA
 301 GGTGCTCGAC GCCTACCTCC GCTCACGGGC ACAGTCCGTC GGCGCGGAGG
 351 TCGTCAACGG CCTCTTCCTA AGGTACGAGG CGCCCAAAGA GCCGAACGGC
 401 TCGTACGTGG TGCACTACAA CCACTACGAC GGCAGCAACG GCAAGGTCGG
 451 CGGCGAGAAG CGGTCGTTCG AGGTGGACGC GATCGTGGGC GCGGACGGCG
 501 CCAACTCTCG CGTGGCCAAC GACATGGGCG CGGGCGACTA CGAGTACGCC
 551 ATCGCGTTCC AGGAGCGCGT CAAGATCCCC GACGACAAGA TGGTGTACTA
 601 CGAGGAGCGC GCGGAGATGT ACGTCGGCGA CGACGTCTCT CCCGACTTCT
 651 ACGGCTGGGT GTTCCCCAAG TGCGACCACG TCGCCGTCGG CACCGGCACC
 701 GTCACGCACA AGGCCGACAT CAAGAAGTTT CAGGCCGCCA CGCGCCTCCG
 751 CGCCAAGGAC AAGATTGAGG CGGCAAGAT CATCCGCGTC GAGGCGCACC
 801 CCATCCCCGA GCACCCCAGG CCTAAGAGGG TGTCCGGGCG GGTGACGCTT
 851 GTGGGCGATG CCGCGGGGTA CGTGACCAAG TGCTCTGGCG AGGGCATCTA
 901 CTTCGCGGCG AAGAGCGGGC GGATGTGCGC CGAGGCCATC GTGGCGGGCT
 951 CCGCCAACGG GACGCGGATG GTGGAGGAGA GCGACCTGCG CAAGTACCTG
1001 GCCGAGTTCG ACCGCCTCTA CTGGCCCACT TACAAGGTGC TGGACATCCT
1051 GCAGAAGGTG TTCTACCGCT CCAACGCGGC GCGCGAGGCC TTCGTGGAGA
1101 TGTGCGCCGA CGACTACGTG CAGAAGATGA CCTTCGACAG CTACCTCTAC
1151 AAGCGCGTCG TGCCGGGCAA CCCGCTCGAC GACATCAAGC TCGCCGTCAA
1201 CACCATCGGC AGCCTCGTCA GGGCCACCGC ACTGCGCCGG AGATGGAGA
1251 AGGTCACCTT GTGAGCCGCC GCCCGCCACG TCATTGCCGT CGAAATGGTG
1301 TCGCAGCTGA TCGGCCGGTG TATTAGTAGA GATTTGCGGC TGATCGGGTT
1351 AATTTAGGCC AACATGCGTG GGCAGTGGGC GCGGAGAGGA AGAGAAACAA
1401 GTTGTGCAAG TGCAGCAAGT AGATCAAAAG TGCTGCCTGT TTGTATCGAT
1451 GGATCCTGCA ACATATAGCA TCTGGTGATG TTGAGAATTC GGAGCAGTTC
1501 ATCGACTGGA TTCTGACGCC GGCAAGCATC GACGTCAATG AATGTCTAAT
1551 ACTTAGTACA TCAAGACATG TAATAAAACT GAAACTCCCC CGTTCTGGTT
1601 CAAAAAAAAA AAAAAAAAA AAAAAAAAA AAAAGGGCG GCCGC
```

FIG. 16

```
  1  LRVAVVGGGP AGGAAAEALA KGGVETVLIE RKMDNCKPCG GAIPLCMVSE
 51  FDLPLDLVDR KVRKMKMISP SNVAVDIGRT LAPHEYIGMV RREVLDAYLR
101  SRAQSVGAEV VNGLFLRYEA PKEPNGSYVV HYNHYDGSNG KVGGEKRSFE
151  VDAIVGADGA NSRVANDMGA GDYEYAIAFQ ERVKIPDDKM VYYEERAEMY
201  VGDDVSPDFY GWVFPKCDHV AVGTGTVTHK ADIKKFQAAT RLRAKDKIEG
251  GKIIRVEAHP IPEHPRPKRV SGRVTLVGDA AGYVTKCSGE GIYFAAKSGR
301  MCAEAIVAGS ANGTRMVEES DLRKYLAEFD RLYWPTYKVL DILQKVFYRS
351  NAAREAFVEM CADDYVQKMT FDSYLYKRVV PGNPLDDIKL AVNTIGSLVR
401  ATALRREMEK VTL*AAARDV IAVEMVSQLI GRCISRDLRL IGLI*ANMRG
451  QWARRGRETS CASAASRSKV LPVCIDGSCN I*HLVMLRIR SSSSTGF*RR
501  QASTSMNV*Y LVHQDM**N* NSPVLVQKKK KKKKKKKGG R
```

METHODS FOR PRODUCING CAROTENOID COMPOUNDS, TOCOPHEROL COMPOUNDS, AND SPECIALTY OILS IN PLANT SEEDS

INCORPORATION OF SEQUENCE LISTING

A paper copy of the Sequence Listing and a computer readable form of the sequence listing ("CRF") on diskette, containing the file named "16516.122. txt", which is 14,451 bytes in size (measured in MS-DOS), and which was created on Jan. 22, 2002, are herein incorporated by reference.

FIELD OF THE INVENTION

The invention relates to genetic modification of plants, plant cells and seeds, particularly altering carotenoid biosynthesis, tocopherol biosynthesis, and fatty acid composition.

BACKGROUND OF THE INVENTION

Carotenoids

Carotenoids are pigments with a variety of applications. They are yellow-orange-red lipids which are present in green plants, some molds, yeast and bacteria. Carotenoid hydrocarbons are referred to as carotenes, whereas oxygenated derivatives are referred to as xanthophylls. The carotenoids are part of the larger isoprenoid biosynthesis pathway, which, in addition to carotenoids, produces such compounds as chlorophyll and tocopherols, Vitamin E active agents. The carotenoid pathway in plants produces carotenes, such as α- and βcarotene, and lycopene, and xanthophylls, such as lutein.

The biosynthesis of carotenoids involves the condensation of two molecules of the $C_{20}$ precursor geranyl $PP_i$ to yield the first $C_{40}$ hydrocarbon phytoene. In a series of sequential desaturatioris, phytoene yields lycopene. Lycopene is the precursor of the cyclic carotenes, β-carotene and a α-carotene. The xanthophylls, zeaxanthin and lutein are formed by hydroxylation of β-carotene and a α-carotene, respectively.

βcarotene, a carotene whose color is in the spectrum ranging from yellow to orange, is present in a large amount in the roots of carrots and in green leaves of plants. βcarotene is useful as a coloring material and also as a precursor of vitamin A in mammals. Current methods for commercial production of β-carotene include isolation from carrots, chemical synthesis, and microbial production.

A number of crop plants and a single oilseed crop are known to have substantial levels of carotenoids, and consumption of such natural sources of carotenoids have been indicated as providing various beneficial health effects. The below table provides levels of carotenoids that have been reported for various plant species.

| CAROTENOID CONTENTS OF VARIOUS CROPS (µg/g) | | | | | |
|---|---|---|---|---|---|
| Crop | Beta-Carotene | Alpha-Carotene | Lycopene | Lutein | Total |
| Carrots | 30–110 | 10–40 | 0–0.5 | 0–2 | 65–120 |
| Pepper (gr) | 2 | — | — | 2 | 8 |
| Pepper (red) | 15 | 1 | — | — | 200 |
| Pumpkin | 16 | 0.3 | tr | 26 | 100 |
| Tomato | 3–6 | — | 85 | — | 98 |
| Watermelon | 1 | tr | 19 | — | 25 |
| Marigold petals | 5 | 4 | — | 1350 | 1500 |
| Red palm oil | 256 | 201 | 8 | — | 545 |

The pathway for biosynthesis of the carotenoids has been studied in a variety of organisms and the biosynthetic pathway has been elucidated in organisms ranging from bacteria to higher plants. See, for example, Britton, G. (1988) *Biosynthesis of carotenoids*, p. 133–182, In T. W. Goodwin (ed.), *Plant pigments*, 1988. Academic Press, Inc. (London), Ltd., London. Carotenoid biosynthesis genes have also been cloned from a variety of organisms including *Erwinia uredovora* (Misawa et al. (1990) *J. Bacteriol.* 172:6704–6712; *Erwinia herbicola* (Application WO 91/13078, Armstrong et al. (1990) *Proc. Nat. Acad. Sci., USA* 87:9975–9979); *R. capsulatus* (Armstrong et al. (1989) *Mol. Gen. Genet.* 216:254–268, Romer et al. (1993) *Biochem. Biophys. Res. Commun.* 196:1414–1421); *Thermus thermophilus* (Hoshino et al. (1993) *Appl. Environ. Microbiol.* 59:3150–3153); the cyanobacterium Synechococcus sp. (Genbank accession number X63873). See also, application WO 96/13149 and the references cited therein.

While the genes have been elucidated, little is known about the use of the genes in plants. Investigations have shown that over expression or inhibition of expression of the plant phytoene synthase (Psy1) gene in transgenic plants can alter carotenoid levels in fruits. See, Bird et al. (1991) *Biotechnology* 9:635–639; Bramley et al. (1992) *Plant J.* 2:343–349; and Fray and Grierson (1993) *Plant Mol. Biol.* 22:589–602. Further, as reported by Fray et al. (1995) *The Plant Journal* 8:693–701, constitutive expression of a fruit phytoene synthase gene in transgenic tomatoes causes dwarfism by redirecting metabolites from the gibberellin pathway.

Application WO 96/13149 reports on enhancing carotenoid accumulation in storage organs such as tubers and roots of genetically engineered plants. The application is directed towards enhancing colored native carotenoid production in specific, predetermined non-photosynthetic storage organs. The examples of the application are drawn to increasing colored carotenoids in transformed carrot roots and in orange flesh potato tubers. Both of these tissues are vegetative tissues, not seeds, and natively have a high level of carotenoids.

Carotenoids are useful in a variety of applications. Generally, carotenoids are useful as supplements, particularly vitamin supplements, as vegetable oil based food products and food ingredients, as feed additives in animal feeds and as colorants. Specifically, phytoene finds use in treating skin disorders. See, for example, U.S. Pat. No. 4,642,318. Lycopene, α- and β-carotene are used as food coloring agents. Consumption of β-carotene and lycopene has also been implicated as having preventative effects against certain kinds of cancers. In addition, lutein consumption has been associated with prevention of macular degeneration of the eye.

Plant oils are useful in a variety of industrial and edible applications. Novel vegetable oils compositions and/or improved means to obtain oils compositions, from biosynthetic or natural plant sources are needed. Depending upon the intended oil use, various different fatty acid compositions are desired. The demand for modified oils with specific fatty acid compositions is great, particularly for oils high in oleic acid. See, Haumann, B. F. (1996) *INFORM* 7:320–334. As reported by Haumann, the ideal frying oil would be a low-saturate, high oleic and low linolenic oil. Furthermore, studies in recent years have established the value of monounsaturated fatty acids as a dietary constituent.

Attempts have been made over the years to improve the fatty acid profiles of particular oils. For example, the oxidative stability of vegetable oil is related to the number of double bonds in its fatty acids. That is, molecules with several double bonds are recognized to be more unstable. Thus, scientists have attempted to reduce the content of α-linolenic acid in order to improve shelf life and oxidative stability, particularly under heat.

It is apparent that there is needed a method for producing significant levels of carotenoid compounds in crop plants and particularly in plant seeds. It would additionally be beneficial to alter the fatty acid content of the plants and seeds. Such altered seed products would be useful nutritionally as well as provide a source for producing more stable oils. There is no report of methods to substantially altering the levels and composition of carotenoids produced in a plant seed, particularly with respect to increasing the level of production of carotenoids. There is therefore needed, a useful method for altering carotenoid levels in plants, particularly seeds, and for producing oils with modified carotenoid composition and/or content.

Tocopherols

A number of unique and interconnected biochemical pathways leading to secondary metabolites, including tocopherols, exist in chloroplasts of higher plants. Tocopherols not only perform vital functions in plants, but are also important from mammalian nutritional perspectives. In plastids, tocopherols account for up to 40% of the total quinone pool. As shown in FIG. 15, the biosynthesis of α-tocopherol in higher plants involves condensation of homogentisic acid and phytylpyrophosphate to form 2-methyl-6 phytylbenzoquinol that can, by cyclization and subsequent methylations (Fiedler et al., 1982, *Planta*, 155: 511–515, Soll et al., 1980, *Arch. Biochem. Biophys.* 204: 544–550, Marshall et al., 1985 *Phytochem.*, 24: 1705–1711, all of which are herein incorporated by reference in their entirety), form various tocopherols. Considering the structure and source from which the structural moieties can be derived, the plant tocopherol biosynthetic pathway can be divided into four parts: formation of homogentisic acid; synthesis of phytylpyrophosphate; cyclization; and S-adenosylmethionine-dependent methylation of the aromatic ring.

PCT International Application WO 97/27285 discloses a cDNA clone from *Arabidopsis thaliana* that encodes p-hydroxyphenyl pyruvic acid dioxygenase (OHPP dioxygenase, or HPD), which catalyzes the production of homogentisic acid from the shikimate pathway intermediate p-hydroxyphenyl pyruvic acid via an oxidation/decarboxylation reaction. This application also discloses a method of creating a transgenic plant in which the levels of OHPP dioxygenase are elevated sufficiently such that production of plastoquinones, Vitamin E, and carotenoids are modified. Organelle targetting of the OHPP dioxygenase is not discussed.

Tocopherols and tocotrienols (unsaturated tocopherol derivatives) are well known antioxidants, and play an important role in protecting cells from free radical damage, and in the prevention of many diseases, including cardiac disease, cancer, cataracts, retinopathy, Alzheimer's disease, and neurodegeneration, and have been shown to have beneficial effects on symptoms of arthritis, and in anti-aging. Vitamin E is used in chicken feed for improving the shelf life, appearance, flavor, and oxidative stability of meat, and to transfer tocols from feed to eggs. Vitamin E has been shown to be essential for normal reproduction, improves overall performance, and enhances immunocompetence in livestock animals. Vitamin E supplement in animal feed also imparts oxidative stability to milk products.

The demand for natural tocopherols as supplements has been steadily growing at a rate of 10–20% for the past three years. At present, the demand exceeds the supply for natural tocopherols, which are known to be more biopotent than racemic mixtures of synthetically produced tocopherols. Naturally occurring tocopherols are all d-stereomers, whereas synthetic α-tocopherol is a mixture of eight d,l-α-tocopherol isomers, only one of which (12.5%) is identical to the natural d-α-tocopherol. Natural d-α-tocopherol has the highest vitamin E activity (1.49 IU/mg) when compared to other natural topherols or tocotrienols. The synthetic α-tocopherol has a vitamin E activity of 1.1 IU/mg. In 1995, the worldwide market for raw refined tocopherols was $1020 million; synthetic materials comprised 85–88% of the market, the remaining 12–15% being natural materials. The best sources of natural tocopherols and tocotrienols are vegetable oils and grain products. Currently, most of the natural Vitamin E is produced from γ-tocopherol derived from soy oil processing, which is subsequently converted to α-tocopherol by chemical modification (α-tocopherol exhibits the greatest biological activity).

Methods of enhancing the levels of tocopherols and tocotrienols in oil seeds and cereal grains, especially levels of the more desirable compounds that can be used directly, without chemical modification, would be useful to the art as such molecules exhibit better functionality and biovailability.

SUMMARY OF THE INVENTION

Transformed plants, plant cells and seeds having altered carotenoid levels and/or modified fatty acid compositions, as well as altered tocopherol levels and composition, are provided. The plants, plant cells and seeds are transformed with at least one carotenoid biosynthesis gene, one tocopherol biosynthesis gene, or a combination thereof. Methods for making and using the transformed compositions of the invention are also provided. Methods find use in altering carotenoid and tocopherol levels in plants, particularly seeds, as well as increasing particular compounds for molecular farming, such as for production of particular carotenoids and tocopherols. At the same time, the transformed compositions, particularly seeds, provide a source of modified oils, which oils may be extracted from the seeds in order to provide an oil product comprising a natural source of various carotenoids, carotenoid mixtures, individual tocopherol compounds, and tocopherol mixtures. In a particular aspect of the present invention, transformed seed can provide a source for particular carotenoid compounds and/or for modified speciality oils having altered carotenoid or tocopherol compositions and/or altered fatty acid composition, particularly having increased levels of oleic acid and decreased levels of linoleic and linolenic acids, and increased levels of α-tocopherol.

BRIEF DESCRIPTION OF THE FIGURES

FIGS. 1A and 1B show the nucleotide sequence of the SSU/crtB fusion sequence.

FIGS. 2A–2F present constructs for expression genes in plant seeds. FIG. 2A presents constructs for expression of carotenoid biosynthesis genes in plant seeds. FIG. 2A shows plasmid pCGN3390 which contains the napin promoter operably linked to the SSU/crtB sequence. FIG. 2B shows plasmid pCGN3392 which contains the napin promoter operably linked to the SSU/crtE sequence. FIG. 2C shows plasmid pCGN9010 which contains the napin promoter operably linked to the SSU/crtI sequence. FIG. 2D shows plasmid pCGN9009 which contains the napin promoter operably linked to the SSU/crtB sequence and the napin promoter operably linked to the SSU/crtI sequence. FIG. 2E shows plasmid pCGN9002 which contains the napin promoter operably linked to the SSU/crtB sequence and the napin promoter operably linked to an antisense epsilon cyclase sequence. FIG. 2F shows plasmid pCGN9017 which contains the napin promoter operably linked to the SSU/crtB sequence and the napin promoter operably linked to an antisense beta cyclase sequence.

FIG. 3 shows the results of analyses of saponified samples for control seeds.

FIGS. 9A and 9B provide sequence of *B. napus* epsilon cyclase cDNA clone 9–4.

FIGS. 10A and 10B provide sequence of *B. napus* epsilon cyclase cDNA clone 7–6.

FIGS. 11A–11D provide sequence of a *B. napus* beta cyclase cDNA clone.

FIGS. 12A and 12B provide T2 seed analysis of 3390 transformed *Brassica napus* plants.

FIG. 13 provides T3 seed analysis of 3390 transformed *Brassica napus* plants.

FIG. 14 provides T2 seed analysis of 9002 transformed *Brassica napus* plants.

FIGS. 16A–16B provides sequence of *Zea mays* geranylgeranylpyrophosphate hydrogenase.

FIG. 17 provides the deduced amino acid sequence of *Zea mays* geranylgeranylpyrophosphate hydrogenase based on the sequence provided in FIG. 16.

DETAILED DESCRIPTION OF THE INVENTION

Figure 2C:
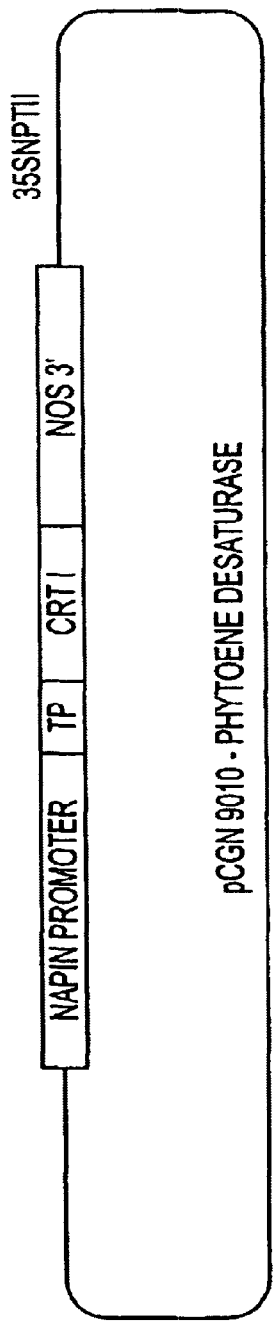

In accordance with the subject invention, methods for increasing production of carotenoid and tocopherol compounds, as well as for altering fatty acid compositions in a plant, particularly in plant seeds, are provided. The method involves transforming a plant cell with at least one carotenoid biosynthesis and/ortocopherol biosynthesis gene. This has the effect of altering carotenoid and/or tocopherol biosynthesis, particularly increasing the production of downstream products, as well as providing novel seed oils having desirable fatty acid compositions. A second gene can then be utilized to shunt the metabolic activity to the production of particular carotenoid or tocopherol compounds, or to further alter the fatty acid composition.

Surprisingly, it has been found that transformation of a plant with an early carotenoid biosynthesis gene leads to a significant increase in the flux through the carotenoid pathway resulting in an increase in particular carotenoids. That is, there is an increase in the metabolic activity that can be further manipulated for the production of specific carotenoids. In addition, the transformed seeds may demonstrate altered fatty acid compositions as the result of the carotenoid gene expression, such as seen with the seeds described herein from plants transformed with a phytoene synthase gene.

Thus, using the methods of the invention, seeds are provided which produce high levels of particular carotenoids or tocopherol, and/or produce speciality oils having a desired fatty acid composition. In oilseed Brassica, for example, transformation with an early carotenoid biosynthesis gene leads to seeds having significant increases in the levels of α-carotene, β-carotene and lutein. In addition, the Brassica seeds demonstrate an altered fatty acid composition and yield a vegetable oil which has increased oleic acid content and decreased linoleic and linolenic acid content. Thus, the transformed seed can provide a source of carotenoid products as well as modified seed oil. In this manner, modified speciality oils can be produced and new sources of carotenoids for extraction and purification are provided.

The oils of the present invention also provide a substantial improvement with respect to stability as compared to two other major plant sources of carotenoids, marigold petals and red palm oil (mesocarp). Although instability is observed in seeds stored in air at room temperature as demonstrated by loss of approximately 20–30% of total carotenoids after 4 weeks of storage, the loss after 1–2 weeks is only 10%. Palm mesocarp, by contrast, must be processed within a day or two of harvest in order to avoid major losses of carotenoids. Furthermore, the carotenoid decomposition in the seeds of the present invention may be reduced significantly by storage of the seeds under nitrogen.

For the production of a seed having an increase in carotenoid biosynthesis, transformation of the plant with an early carotenoid biosynthesis gene is sufficient. By early carotenoid biosynthesis gene is intended geranylgeranyl pyrophosphate synthase, phytoene synthase, phytoene desaturase, and isopentenyl diphosphate (IPP) isomerase. A variety of sources are available for the early carotenoid biosynthesis genes and for the most part, a gene from any source can be utilized. However, it is recognized that because of co-suppression, the use of a plant gene native to the target host plant may not be desirable where increased expression of a particular enzyme is desired.

A number of early carotenoid biosynthesis genes have been isolated and are available for use in the methods of the present invention. See, for example:

IPP isomerase has been isolated from: *R. Capsulatus* (Hahn et al. (1996) *J. Bacteriol.* 178:619–624 and the references cited therein), GenBank Accession Nos. U48963 and X82627, *Clarkia xantiana* GenBank Accession No. U48962, *Arabidopsis thaliana* GenBank Accession No. U48961, *Schizosaccharmoyces pombe* GenBank Accession No. U21154, human GenBank Accession No. X17025, *Kluyveromyces lactis* GenBank Accession No. X14230;

geranylgeranyl pyrophosphate synthase from *E. Uredovora* Misawa et al. (1990) *J. Bacteriol.* 172:6704–6712 and Application WO 91/13078; and from plant sources, including white lupin (Aitken et al. (1995) *Plant Phys.* 108:837–838), bell pepper (Badillo et al. (1995) *Plant Mol. Biol.* 27:425–428) and *Arabidopsis* (Scolnik and Bartely (1994) *Plant Physiol.* 104:1469–1470; Zhu et al. (1997) *Plant Cell Physiol.* 38:357–361).

phytoene synthase from a number of sources including *E. Uredovora, Rhodobacter capsulatus*, and plants Misawa et al. (1990) *J. Bacteriol.* 172:6704–6712, GenBank Accession No. D90087, Application WO 91/13078, Armstrong et al. (1989) *Mol. Gen. Genet.* 216:254–268, Armstrong, G. A. "Genetic Analysis and regulation of carotenoid biosynthesis. In R. C. Blankenship, M. T. Madigan, and C. E. Bauer (ed.), *Anoxygenic photosynthetic bacteria; advances in photosynthesis*. Kluwer Academic Publishers, Dordrecht, The Netherlands, Armstrong et al. (1990) *Proc. Natl. Acad. Sci USA* 87:9975–9979, Armstrong et al. (1993) *Methods Enzymol.* 214:297–311, Bartley and Scolnik (1993) *J. Biol. Chem.* 268:27518–27521, Bartley et al. (1992) *J. Biol Chem.* 267:5036–5039, Bramley et al. (1992) *Plant J.* 2:291–343, Ray et al. (1992) *Plant Mol. Biol.* 19:401–404, Ray et al. (1987) *Nucleic Acids Res.* 15:10587, Romer et al. (1994) *Biochem. Biophys. Res. Commun.* 196:1414–1421, Karvouni et al. (1995) *Plant Molecular Biology* 27:1153–1162, (GenBank Accession Nos. U32636, Z37543, L37405, X95596, D58420, U32636, Z37543, X78814, X82458, S71770, L27652, L23424, X68017, L25812, M87280, M38424, X69172, X63873, and X60441, Armstrong, G. A. (1994) *J. Bacteriol.* 176:4795–4802 and the references cited therein; and, phytoene desaturase from bacterial sources including *E. uredovora* Misawa et al. (1990) *J. Bacteriol.* 172:6704–6712, and Application WO 91/13078 (GenBank Accession Nos. L37405, X95596, D58420, X82458, S71770, and M87280); and from plant sources, including maize(Li et al. (1996) *Plant Mol. Biol.* 30:269–279), tomato (Pecker et al. (1992) *Proc. Nat. Acad. Sci.* 89:4962–4966 and Aracri et al. (1994) *Plant Physiol.* 106:789), and *Capisum annuum* (bell beppers) (Hugueney et al. (1992) *J. Biochem.* 209:399–407), GenBank Accession Nos. U37285, X59948, X78271, and X68058).

See, generally, Misawa et al. (1990) *J. of Bacteriology* 172:6704–6712, E. P. 0393690 B1, U.S. Pat. No 5,429,939, Bartley et al. (1992) *J. Biol. Chem.* 267:5036–5039, Bird et al. (1991) *Biotechnology* 9:635–639, and U.S. Pat. No. 5,304,478, which disclosures are herein incorporated by reference.

Transformation with an early carotenoid gene, (herein referred to as the primary gene), increases the biosynthetic activity of the carotenoid pathway, and can lead to increased production of particular carotenoids such as for example, α- and β-carotene. As described in more detail in the following examples, by expression of phytoene synthase as the primary gene, large increases in the carotenoid content generally, and particularly in the levels of α- and β-carotene, are obtained in seeds of transformed plants. Oil comprising the carotenoids so produced may be extracted from the seeds to provide a valuable source of α- and β-carotenes. Such an oil may find use as a food colorant, for example to add color to margarines, or as a food oil. An edible food oil with high α- and β-carotene levels is of interest for prevention of Vitamin A deficiency which can result in night blindness. Thus, production of transformed plants and extraction of the high α- and β-carotene oil to provide a useful food oil is particularly desirable in regions where night blindness is a widespread problem, such as in India and Asia.

In addition to high α- and β-carotene levels, levels of other carotenoids are also increased in the oils exemplified herein. For example, lutein levels are increased in seeds from plants transformed with a phytoene synthase gene, as well as in seeds from plants transformed with a GGPP synthase gene, crtE (3392), or with phytoene desaturase, crtI (9010).

Furthermore, additional primary genes may be expressed to provide for even greater flux through the carotenoid pathway. For example, in oilseed Brassica seeds transformed with a phytoene synthase gene as described herein, increased levels of phytoene are observed. Thus, increasing the expression of phytoene desaturase as well as phytoene synthase may result in further increases in the levels of carotenoids, such as α- and β-carotene and lutein, produced. Such further modification of carotenoid composition is demonstrated here in transgenic plant seeds transformed with pCGN9009 for the expression of crtB and crtI genes. Additionally, plants expressing both phytoene synthase and GGPP synthase genes are desirable. Such plants may demonstrate even greater flux through the carotenoid pathway as indicated by the increased production of chlorophyll observed in plants of the present invention which have been transformed to express a GGPP synthase gene (crtE) in the absence of crtB over expression.

Interestingly, plants expressing a GGPP synthase gene did not have significant modifications of the tocopherol content. Since GGPP is a branch point of the carotenoid, chlorophyll and tocopherol pathways in plants, these observations suggest that the next enzymatic step in tocopherol biosynthesis, catalyzed by GGPP hydrogenase, is a rate limiting step for tocopherol production. Thus, providing for increased expression of GGPP hydrogenase, alone or in conjunction with increased expression of GGPP synthase would be expected to result in an increase of flux to the tocopherol pathway.

Also of interest are plants which are transformed to express three early carotenoid biosynthesis gens, crtB, crtE, and crtI. Plants expressing two or three different carotenoid biosynthsis genes may be produced by either transforming a plant with a construct providing for expression of the desired genes, using a multiple gene construct or by cotransformation with multiple constructs, or by crossing plants which contain the different desired genes.

In addition to the production of the carotenoids described herein, once the biosynthetic activity has been increased by expression of the primary carotenoid biosynthesis gene or genes, the pathway can be diverted for the production of specific compounds. The diversion involves the action of at least one second gene of interest, (the secondary gene). The secondary gene can encode an enzyme to force the production of a particular compound or alternatively can encode a gene to stop the pathway for the accumulation of a particular compound. For forcing the production of a particular compound, expression of a carotenoid biosynthesis gene in the pathway for the desired carotenoid compound is used. Genes native or foreign to the target plant host may find use in such methods, including, for example, carotenoid biosynthesis genes from sources other than higher plant, such as bacteria, including Erwinia and Rhodobacter species. For stopping the pathway in order to accumulate a particular carotenoid compound, the secondary gene will provide for inhibition of transcription of a gene native to the target host plant, wherein the enzyme encoded by the inhibited gene is capable of modifying the desired carotenoid compound. Inhibition may be achieved by, transcription of the native gene to be inhibited in either the sense (cosuppression) or antisense orientation of the gene.

For example, for alteration of the carotenoid composition towards the accumulation of higher levels of β-carotene derived carotenoids, such as zeaxanthin, zeaxanthin diglucoside, canthaxanthin, and astaxanthin, inhibition of lycopene epsilon cyclase is desired to prevent accumulation of alpha carotene and its derivative carotenoids, such as lutein. In addition, overexpression of lycopene β-cyclase may be. used to increase the accumulation of β-carotene derived carotenoids. Thus, antisense lycopene epsilon cyclase and lycopene β-cyclase are examples of sequences which find use in secondary gene constructs of interest in the present invention. Furthermore, in conjunction with the inhibition of lycopene epsilon cyclase, increased expression of additional secondary genes may be desired for increased accumulation of a particular beta-carotene derived carotenoid. For example, increased, β-carotene hlydroxylase; expression is useful for production of zeaxanthin, wherease increased β-carotene hydroxylase and keto-introducing enzyme expression is useful for production of astaxanthin. Alternatively, for accumulation of lycopene, inhibition of lycopene beta cyclase or of lycopene epsilon cyclase and lycopene beta cyclase is desired to reduce conversion of lycopene to alpha- and beta β-carotene.

Thus, the carotenoid pathway can be manipulated by expression of carotenoid biosynthesis genes to increase production of particular carotenoids, or by decreasing levels of a particular carotenoid by transformation with antisense DNA sequences which prevent the conversion of a'selected precursor compound into the next carotenoid in the pathway.

Secondary genes of interest in the present application include but are not limited to:

β-carotene hydrdxylase or crtZ (Hundle et al. (1993) *FEBS Lett*. 315:329–334, GenBank Accession No. M87280) for the production of zeaxanthin;

genes encoding keto-introducing enzymes, such ascrtW (Misawa et al. (1995) *J. Bacteriol*. 177:6575–6584, WO 95/18220, WO 96/06172) or β-C-4-oxygenzse (crtO; Harker and Hirschberg (1997) *FEBS Lett*. 404:129–134) for the production of canthaxanthin;

crtZ and crtW or crtO for the production of astaxanthin;

ε-cyclase and ε-hydroxylase for the production of lutein;

ε-hydroxylase and crtZ for the production of lutein and zeaxanthin;

lycopene β-cyclase (crtY) (Hugueney et al. (1995) *Plant J*. 8:417–424, Cunningham FX Jr (1996) *Plant Cell* 8:1613–1626, Scolnik and Bartley (1995) *Plant Physiol*. 108:1343, GenBank Accession Nos. X86452, L40176, X81787, U50739 and X74599) for increased production of β-carotene.

antisense lycopene ε-cyclase (GenBank Accession No. U50738) for increased production of β-carotene;

antisense lycopene ε-cyclase and lycopene β-cyclase for the production of lycopene;

antisense plant phytoene desaturase for the production of phytoene; etc.

In this manner, the pathway can be modified for the high production of any particular carotenoid compound of interest. Such compounds include but are not limited to the particular compounds described above, as well as, α-cryptoxanthin, β-cryptoxanthin, ζ-carotene, phytofluene, neurosporane, and the like. Using the methods of the invention, any compound of interest in the carotenoid pathway can be produced at high levels in a seed.

Secondary genes can also be selected to alter the fatty acid content of the plant for the production of speciality oils. For example, acyl-ACP thioesterase genes having specificity for particular fatty acid chain lengths may be used. See, for example, U.S. Pat. No. 5,304,481, U.S. Pat. No. 5,455,167, WO 95/13390, WO 94/10288, WO 92/20236, WO 91/16421, WO 97/12047 and WO 96/36719. Other fatty acid biosynthesis genes of interest include, but are not limited to, β-keto acyl-ACP synthases (U.S. Pat. No. 5,510,255), fatty acyl CoA synthases (U.S. Pat. No. 5,455,947), fatty acyl reductases (U.S. Pat. No. 5,370,996) and stearoyl-ACP desaturases (WO 91/13972).

Of particular interest is the use of a mangosteen acyl-ACP thioesterase as a secondary gene for fatty acid content modification. As described in WO 96/36719 and WO 97/12047, a high stearate content may be obtained in seeds by expression of a mangosteen acyl-ACP thioesterase. To combine the high oleic acid trait of the 3390 plants described herein with the 5266 high stearate plants described in WO 97/12047, crosses were made between 3390-1 and 5266-35 and between 3390-1 and 5266-5. Seeds resulting from these crosses contained oil having a high stearate, low linoleic, low linolenic and high carotenoid phenotype.

Any means for producing a plant comprising the primary gene or both the primary and secondary genes are encompassed by the present invention. For example, the secondary gene of interest can be used to transform a plant at the same time as the primary gene either by inclusion of both expression constructs in a single transformation vector or by using separate vector, each of which express desired primary or secondary. genes. The secondary gene can be introduced into a plant which has already been transformed with the primary gene, or alternatively, transformed plants, one expressing the primary gene and one expressing the secondary gene, can be crossed to bring the genes together in the same plant.

By combining the genes with tissue specific promoters, the carotenoid levels can be altered in particular tissues of the plant. Thus, carotenoid levels in the seed, including embryos and endosperm, can be altered by the use of seed specific transcriptional initiation regions. Such regions are disclosed, for example, in U.S. Pat. No. 5,420,034, which disclosure is herein incorporated by reference.

In this manner, the transformed seed provides a factory for the production of modified oils. The modified oil may be used or alternatively, the compounds in the oils can be isolated. Thus, the present invention allows for the production of particular compounds of interest as well as speciality oils.

The primary or secondary genes encoding the enzymes of interest can be used in expression cassettes for expression in the transformed plant tissues. To alter the carotenoid or fatty acid levels in a plant of interest, the plant is transformed with at least one expression cassette comprising a transcriptional initiation region linked to a gene of interest. Such an expression cassette is provided with a plurality of restriction sites for insertion of the gene of interest to be under the transcriptional regulation of the regulatory regions.

The transcriptional initiation may be native or analogous to the host or foreign or heterologous to the host. By foreign is intended that the transcriptional initiation region is not found the wild-type host into which the transcriptional initiation region is introduced.

Of particular interest are those transcriptional initiation regions associated with storage proteins, such as napin, cruciferin, β-conglycinin, phaseolin, or the like, and proteins involved in fatty acid biosynthesis, such as acyl carrier protein (ACP). See, U.S. Pat. No 5,420,034, herein incorporated by reference.

The transcriptional cassette will include the in 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al., (1991), *Mol. Gen. Genet.*, 262:141–144; Proudfoot, (1991), *Cell*, 64:671–674; Sanfacon et al., (1991), *Genes Dev.*, 5:141–149; Mogen et al., (1990), *Plant Cell*, 2:1261–1272; Munroe et al., (1990), *Gene*, 91:151–158; Ballas et al., (1989), *Nucleic Acids Res.*, 17:7891–7903; Joshi et al., (1987), *Nucleic Acid Res.*, 15:9627–9639).

For the most part, the genes of interest of the present invention will be targeted to plastids, such as chloroplasts, for expression. Thus, the carotenoid biosynthesis gene or genes of interest may be inserted into the plastid for expression with appropriate plastid constructs and regulatory elements. Alternatively, nuclear transformation may be used in which case the expression cassette will contain a gene encoding a transit peptide to direct the carotenoid biosynthesis gene of interest to the plastid. Such transit peptides are known in the art. See, for example, Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481. Plant carotenoid genes useful in the invention may utilize native or heterologous transit peptides.

It is noted that where the gene or DNA sequence of interest is an antisense DNA, targeting to a plastid is not required.

The construct may also include any other necessary regulators such as plant translational consensus sequences (Joshi, C. P., (1987), *Nucleic Acids Research*, 15:6643–6653), introns (Luehrsen and Walbot, (1991), *Mol. Gen. Genet.*, 225:81–93) and the like, operably linked to the nucleotide sequence of interest.

It may be beneficial to include 5' leader sequences in the expression cassette which can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) *PNAS USA* 86:6126–6130); potyvirus leaders, for example, TEV leader (Tobacco Etch Virus) (Allison et al., (1986); MDMV leader (Maize Dwarf Mosaic Virus); *Virology*, 154:9–20), and human immunoglobulin heavy-chain binding protein (BiP), (Macejak, D.G., and Sarnow, P., (1991), *Nature*, 353:90–94; untranslated leader from the coat protein mRNA of alfalfa mosaic virus (AMV RNA 4), (Jobling, S. A., and. Gehrke, L., (1987), *Nature*, 325:622–625; tobacco mosaic virus leader (TMV), (Gallie, D. R. et al., (1989), *Molecular Biology of RNA*, pages 237–256; and maize chlorotic mottle virus leader (MCMV) (Lommel, S. A. et al., (1991), *Virology*, 81:382–385. See also, Della-Cioppa et al., (1987), *Plant Physiology*, 84:965–968.

Depending upon where the DNA sequence of interest is to be expressed, it may be desirable to synthesize the sequence with plant preferred codons, or alternatively with chloroplast preferred codons. The plant preferred codons may be determined from the codons of highest frequency in the proteins expressed in the largest amount in the particular plant species of interest. See, EPA 0359472; EPA 0385962; WO 91/16432; Perlak et al. (1991) *Proc. Natl. Acad. Sci. USA* 88:3324–3328; and Murray et al. (1989) *Nucleic Acids Research* 17: 477–498. In this manner, the nucleotide sequences can be optimized for expression in any plant. It is recognized that all or any part of the gene sequence may be optimized or synthetic. That is, synthetic or partially optimized sequences may also be used. For the construction of chloroplast preferred genes, see U.S. Pat. No. 5,545,817.

In preparing the transcription cassette, the various DNA fragments may be manipulated, so as to provide for the DNA sequences in the proper orientation and, as appropriate in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g. transitions and transversions, may be involved.

The recombinant DNA molecules of the invention can be introduced into the plant cell in a number of art-recognized ways. Those skilled in the art will appreciate that the choice of method might depend on the type of plant, i.e. monocot or dicot, targeted for transformation. Suitable methods of transforming plant cells include microinjection (Crossway et al. (1986) *BioTechniques* 4:320–334), electroporation (Riggs et al. (1986) *Proc. Natl. Acad. Sci. USA* 83:5602–5606, Agrobacterium mediated transformation (Hinchee et al. (1988) *Biotechnology* 6:915–92 1) and ballistic particle acceleration (see, for example, Sanford et al., U.S. Pat. No. 4,945,050; and McCabe et al. (1988) *Biotechnology* 6:923–926). Also see, Weissinger et al. (1988) *Annual Rev. Genet.* 522:421–477; Sanford et al. (1987) *Particulate Science and Technology* 5:27–37(onion); Christou et al. (1988) *Plant Physiol.* 87:671–674(soybean); McCabe et al. (1988) *Bio/Technology* 6:923–926 (soybean); Datta et al. (1990) *Biotechnology* 8:736–740(rice); Klein et al. (1988) *Proc. Natl. Acad. Sci. USA*, 85:4305–4309 (maize); Klein et al. (1988) *Biotechnology* 6:559–563 (maize); Klein et al. (1988) *Plant Physiol.* 91:440–444 (maize); Fromm et al. (1990) *Biotechnology* 8:833–839; and Gordon-Kamm et al. (1990) *Plant Cell*, 2:603–618 (maize).

Alternatively, a plant plastid can be transformed directly. Stable transformation of chloroplasts has been reported in higher plants, see, for example, SVAB et al. (1990) *Proc. Nat'l. Acad. Sci. USA* 87:8526–8530; SVAB & Maliga (1993) *Proc. Nat'l Acad. Sci. USA* 90:913–917; Staub & Maliga (1993) *Embo J.* 12:601–606. The method relies on. particle gun delivery of DNA containing a selectable marker and targeting of the DNA to the plastid genome through homologous recombination. In such methods, plastid gene expression can be accomplished by use of a plastid gene promoter or by trans-activation of a silent plastid-borne transgene positioned for expression from a selective promoter sequence such as that recognized by T7 RNA polymerase. The silent plastid gene is activated by expression of the specific RNA polymerase from a nuclear expression construct and targeting of the polymerase to the plastid by use of a transit peptide. Tissue-specific expression may be obtained in such a method by use of a nuclear-encoded and plastid-directed specific. RNA polymerase expressed from a suitable plant tissue specific promoter. Such a system has been reported in McBride et al. (1994) *Proc. Natl. Acad. Sci., USA* 91:7301–7305.

The cells which have been transformed may be grown into plants in accordance with conventional ways. See, for example, McCormick et al., *Plant Cell Reports* (1986), 5:81–84. These plants may then be grown, and either self or crossed with a different plant strain, and the resulting homozygotes or hybrids having the desired phenotypic characteristic identified. Two or more generations may be grown to ensure that the subject phenotypic characteristic is stably maintained and inherited and then seeds harvested to ensure the desired phenotype or other property has been achieved.

As a host cell, any plant variety may be employed. Of particular interest, are plant species which provide seeds of interest. For the most part, plants will be chosen where the seed is produced in high amounts, a seed-specific product of interest is involved, or the seed or a seed part is edible. Seeds of interest include the oil seeds, such as oilseed Brassica seeds, cotton seeds, soybean, safflower, sunflower, coconut, palm, and the like; grain seeds, e.g. wheat, barley, oats, amaranth, flax, rye, triticale, rice, corn, etc.; other edible seeds or seeds with edible parts including pumpkin, squash, sesame, poppy, grape, mung beans, peanut, peas, beans, radish, alfalfa, cocoa, coffee, tree nuts such as walnuts, almonds, pecans, chick-peas etc.

It is noted that the methods of the present invention have been demonstrated to provide increased carotenoid production in both oilseed Brassica, which has a green embryo, and in cotton, which has a white embryo.

In seed of cotton plants transformed with phytoene synthase, increases of total carotenoid levels ranging from 10 to 300 fold may be obtained. The majority of the increase in carotenoid levels, in this case, about 80%, is observed as an increase in phytoene levels. Increases in lutein levels are also obtained in this case, ranging from 1.5 to a fold increase. In addition, β-carotene and β-carotene levels are also increased to 100 fold, with β-carotene levels being fold higher than β-carotene levels. Thus, as seen with Brassica, a second early carotenoid biosynthesis gene, such as phytoene desaturase, may be used with crtB to increase the metabolic flux through the carotenoid/isoprenoid pathway in cotton to produce a particular carotenoid.

In one embodiment of the invention, seed transcriptional initiation regions are used in combination with at least one carotenoid biosynthesis gene. This increases the activity of the carotenoid pathway and alters carotenoid levels in the transformed seed. In this manner, particular genes can be selected to promote the formation of compounds of interest. Where the gene selected is an early carotenoid biosynthesis gene the transformed seed has a significant increase in carotenoid biosynthesis as the result of an increase in the flux through the pathway. For Brassica seeds transformed with an early carotenoid biosynthesis gene, significant increases in the production of α-carotene, β-carotene and smaller increases in lutein in the seed oil, as well as altered oil fatty acid compositions are obtained.

Where the early carotenoid biosynthesis gene is phytoene synthase, significant increases of a particular carotenoid include those ranging from a to a 50 fold increase, preferably at least a 50 to a 100 fold increase, more preferably, at least a 50 to, a 200 fold increase, such as the increases seen in α-carotene and β-carotene levels. Lutein levels, in this case, are also increased, but lower increases of 1.5–2 fold are obtained. At the same time, total carotenoid levels may be increased at least 10 to 25 fold, preferably 25 to 60 fold, and more preferably 25 to 100 fold. Thus, a seed of the invention transformed with a phytoene synthase gene has a substantial increase in levels of α- and β-carotene and total carotenoids, as well as smaller increases in lutein and other carotenoids, including phytoene. In some cases, it is not possible to quantitate the fold increase in a given carotenoid compound, as the levels are too low to detect in seeds from comparable non-transformed plants. In *Brassica napus*, for example, α-cryptoxanthin, lycopene, phytoene and phytofluene are all detected in various levels in seeds transformed with a crtB gene, but are not detectable in seeds from untransformed *Brassica napus* plants.

Where the early carotenoid biosynthesis gene is GGPP synthase or phytoene desaturase, 1.5 to 2 fold increases in lutein and β-carotene have been obtained in at least one transgenic plant for each gene. Lycopene is also detected in seeds from *Brassica napus* plants transformed with a crtE (GGPP synthase) gene. Total carotenoids in crtE or crtI transformants are also increased approximately 2 fold. Chlorophyll levels are also increased in *B. napus* transgenic plants expressing a crtE gene suggesting an increase in the levels of geranylgeranyl pyrophosphate (GGPP), which is the branch point substrate for carotenoid, chlorophyll and tocopherol biosynthesis. Increases in chlorophyll levels of 1.5 to 2 fold may be obtained in developing and mature seeds. Thus, also of interest as sources of carotenoids are plants which have been engineered to express increased levels of both crtB and crtE.

As demonstrated herein, the effect of one early carotenoid biosynthesis gene on the metabolic energy flux through the carotenoid pathway may be further effected by the addition of a second early carotenoid biosynthesis gene. Thus, the addition of a second early carotenoid biosynthesis gene for increasing the metabolic flow through the carotenoid biosynthesis pathway is also of interest in the present invention, and may find use for production of particular carotenoids either in the presence or absence of a secondary carotenoid biosynthesis gene.

Where the early carotenoid biosynthesis gene phytoene synthase is cotransformed into Brassica napus with a second early carotenoid biosynthesis gene, phytoene desaturase, significant increases of particular carotenoids include increases in α-carotene, β-carotene, and lutein such as observed by expression of crtB alone. In addition, lycopene and phytoene levels are also increased in such plants, but increases are difficult to quantitate as these levels are too low to be detected in untransformed Brassica napus plants.

Furthermore, when crtI and crtB are both expressed, total carotenoid levels greater than those observed with crtB alone may be obtained. In at least one plant, total carotenoid levels of 1.5 fold those observed in crtB plants were obtained. Lycopene levels are also increased over levels obtained in seeds of plants transformed with crtB alone. Lycopene levels may be increased from 4 to 15 fold over those obtained in seed of a homozygous crtB plant. In addition, a reduction in the ratio of phytoene to total carotenoids is also obtained, and as a result, levels of α-carotene and β-carotene are increased 1.2 to 1.8 fold over those obtained with crtB alone. In seeds of plants transformed with phytoene synthase alone, phytoene levels constituted as much as 20% of total carotenoids, while in plants cotransformed with phytoene synthase and phytoene desaturase, phytoene levels represent only 4% to 7% of the total carotenoids.

This metabolic energy effected by transformation with an early carotenoid gene can be funneled into a metabolic compound of choice by transformation with a second gene. As discussed above, the second gene is designed to promote the synthesis of a particular carotenoid by promoting the formation of the carotenoid of interest or alternatively by stopping the pathway to allow for the buildup of compounds. Therefore, significant amounts of carotenoids of interest can be produced in the transformed seeds of the present invention.

Where the primary carotenoid biosynthesis gene phytoene synthase is cotransformed with an antisense secondary carotenoid biosynthsis gene, $\epsilon$-cyclase, large increases in levels of $\alpha$-carotene, $\beta$-carotene and phytoene, such as those seen with transformation with crtB alone, are obtained. Some difference in the ratio of $\beta$-carotene to $\alpha$-carotene is observed as compared to plants transformed with crtB alone, but large increases in both $\alpha$-carotene and $\beta$-carotene levels are still observed. Lutein levels, on the other hand, are either unchanged, increased, or in some cases decreased by as much as 80% as compared to seeds of untransformed control plants.

Initiation of carotenoid biosynthesis begins at approximately 15 days post anthesis in *B. napus* seeds, while expression of transformed genes utilizing the napin promoter begins about 18 days post anthesis. Thus, in order to more tightly control the $\alpha$-carotene pathway to allow for the build up of $\beta$-caroteniods using antisense $\epsilon$-cyclase, an earlier promoter, such as that of the Lesquerella kappa hyrodoxylase (described in pending U.S. patent application 08/898,038, filed Jul. 18, 1997), may find use. Thus, for increasing levels of a particular carotenoid using antisense, an earlier seed specific tanscriptional initiation region, may be used with a secondary carotenoid biosynthesis gene.

The seeds of the invention which have been transformed with the primary early carotenoid biosynthesis gene also provide a source for novel oil compositions. The use of phytoene synthase as the primary gene, for example, results in substantial increases in oleic acid content in seed oil. By substantial increase is intended an increase of from about 5% to about 40%, specifically from about 20% to about 40%, more specifically from about 30% to about 40%. Thus, the seeds of the invention which have been transformed with a primary early carotenoid biosynthesis gene provide a source for modified oils having a high oleic acid content. That is, carotenoid biosynthesis genes, particularly early carotenoid biosynthesis genes can be used to produce seeds having at least 70% oleic acid, on a weight percentage basis. The oleic acid content in any seed can be altered by the present methods, even those seeds having a naturally high oleic acid content. Alteration of seeds having naturally high oleic acid contents by the present methods can result in total oleic acid contents of as high as 80%.

Importantly, there is also a decrease in linoleic and linolenic acid content. By decrease in linoleic fatty acid content is intended a decrease from about 10% to about 25%, preferably about 25% to about 40%, more preferably about 35% to about 60%. By decrease in linolenic fatty acid content is intended a decrease from about 10% to about 30%, preferably about 30% to about 60%, more preferably about 50% to about 75%. Thus, the methods of the invention result in oils which are more oxidatively stable than the naturally occurring oils. The modified oils of the invention are low-saturate, high oleic and low linolenic. Furthermore, the present invention provides oils high in monounsaturated fatty acids which are important as a dietary constituent.

Based on the methods disclosed herein, seed oil can be modified to engineer an oil with a high oleic acid content as well as a high level of a carotenoid of interest. High oleic acid and and high $\alpha$- and , $\beta$-carotene oils would have a longer shelf life as both the oleic acid and $\alpha$- and $\beta$-carotene content would lend stability. It is also noted that such oils are more desirable as sources of carotenoids than the natural red palm oil, which oil contains high levels of saturated fatty acids.

The transformed seed of the invention can thus provide a source of carotenoid products as well as modified fatty acids. Where the intent is to produce particular carotenoid compounds of interest, methods are available in the art for the purification of the carotenoid compounds. In the same manner, methods available in the art can be utilized to produce oils purified of carotenoids. See, generally, WO 96/13149 and Favati et al. (1988) *J. Food Sci.* 53:1532 and the references cited therein.

The transformed seed and embryos additionally find use as screenable markers. That is, transformed seed and embryos can be visually determined and selected based on color as a result of the increased carotenoid content. The transformed seeds or embryos display a color ranging from yellow to orange to red as a result of the increased carotenoid levels. Therefore, where plant transformation methods involve an embryonic stage, such as in transformation of cotton or soybean, the carotenoid gene can be used in plant transformation experiments as a marker gene to allow for visual selection of transformants. Likewise, segregating'seed can easily be identified as described further in the examples.

In addition to altering the carotenoid levels in seeds, the tocopherol levels can be altered, preferably increased. Such seeds with increased levels of tocopherol, particularly $\alpha$-tocopherol, are desirable as $\alpha$-tocopherol is the most important form of the vitamin E family. Vitamin E is essential for the nutrition of humans and other animals. Evidence is available that vitamin E functions in the body in maintaining the integrity of the red blood cells, as essential in cellular respiration, is involved in the biosynthesis of DNA, and acts as an antioxidant which may have implications in protecting cells from carcinogens. Thus, seeds and oils having increased tocopherol levels are desirable. Oils having a nearly 50% increase in $\alpha$-tocopherol levels are provided herein, and seed oils having even greater increases, up to 2–5 fold, are envisioned using the methods of the present invention.

For the production of seed having an increase in tocopherol biosynthesis, or a modification in the level of tocopherol isomers, transformation of the plant with a tocopherol biosynthesis gene is sufficient. Transgenic plants in which both tocopherol and carotenoid biosynthesis is enhanced can be produced by transforming the plant with at least one tocopherol biosynthesis gene and/or at least one carotenoid biosynthesis gene.

As noted above, the plant tocopherol biosynthetic pathway can be divided into four parts:

1. Formation of homogentisic acid, which contributes to the aromatic ring of tocopherol, from shikimate pathway derived p-hydroxyphenylpyruvate;
2. Synthesis of phytylpyrophosphate, which contributes to the side chain of tocopherol, from the isoprenoid pathway, and prenyltransfer of the phytyl moiety to the aromatic ring;
3. Cyclization, which plays a key role in chirality and chromanol substructure of the vitamin E family; and
4. S-adenosyl methionine-dependent methylation of the aromatic ring, which determines the compositional quality of the vitamin E family produced $\alpha$-, $\beta$-, $\gamma$, or $\delta$-tocols).

The enzymes variously involved in these biochemical steps are as follows.

1) Synthesis of Homogentisic Acid

Homogentisate is well known as the aromatic precursor in the biosynthesis of tocopherols in the chloroplast, and is formed from the aromatic shikimate metabolite p-hydroxyphenylpyruvate. The aromatic amino acids phenylalanine, tyrosine, and tryptophan are formed by a reaction sequence leading from the two carbohydrate precursors, D-erythrose 4-phosphate and phosphoenolpyruvate, via shikimate, to further prearomatic and aromatic compounds (Bentley 1990, *Critical Rev. Biochem. Mol. Biol.* 25: 307–384, the entirety of which herein incorporated by reference). Approximately 20% of the total carbon fixed by green plants is routed through the shikimate pathway, with end products being aromatic amino acids and other aromatic secondary metabolites such as flavonoids, vitamins, lignins, alkaloids, and phenolics (Herrmann 1995, *Plant Physiol.* 107: 7–12; Kishore and Shah 1988, *Ann. Rev. Biochem.*, 57:67–663, all of which are herein incorporated by reference in their entirety). Various aspects of the shikimate pathway have been reviewed (Bentley 1990, *Critical Rev. Biochem. Mol. Biol.* 25: 307–384, Herrmann 1995, *Plant Physiol.* 107: 7–12, Kishore and Shah 1988, *Ann. Rev. Biochem.*, 57:67–663, all of which are herein incorporated by reference in their entirety):

The first committed reaction in the shikimate pathway is catalyzed by the enzyme 3-deoxy-D-arabino- heptulosonate-7-phosphate synthase (DAHP synthase, EC. 4.1.2.15), which controls carbon flow into the shikimate pathway. The plastid-localized DAHP synthase catalyzes the formation of 3-deoxy-D-arabino-heptulosonate 7-phosphate by condensing D-erythrose 4-phosphate with phosphoenolpyruvate. This enzyme has been isolated and well characterized from plant sources including carrot and potato, has highest substrate specificity for D-erythrose 4-phosphate and phosphoenolpyruvate, is a dimer of subunits of Mr=53,000, and is activated by $Mn^{2+}$ (Herrmann 1995, Plant Physiol. 107: 7–12, 770 the entirety of which is herein incorporated by reference). The aromatic amino acids are not feed back regulators: the purified enzyme is activated by tryptophan and to a lesser extent by tyrosine in a hysteric fashion (Suzich et al., 1985, *Plant Physiol.* 79: 765–770, the entirety of which is herein incorporated by reference).

The next enzyme in the shikimate pathway, 3-dehydroquinate synthase (EC. 4.6.1.3), catalyzes the formation of dehydroquinate, the first carbocyclic metabolite in the biosynthesis of aromatic amino acids, from D-erythrose 4-phosphate with phosphoenolpyruvate. The enzyme reaction involves AND cofactor-dependent oxidation-reduction, β-elimination, and intramolecular aldol condensation. 3-Dehydroquinate synthase has been purified from *Phaseolus mungo* seedlings and pea seedlings, and has a native Mr of 66,000 with a dimer subunit (Yamamoto, 1980, *Phytochem.*, 19: 779, Pompliano et al., 1989, *J. Am. Chem. Soc.*, 111: 1866, all of which are herein incorporated by reference in their entirety).

3-Dehydroquinate dehydratase (EC 4.2.1.10) catalyzes the stereospecific syn-dehydration of dehydroquinate to dehydroshikimate, and is responsible for initiating the process of aromatization by introducing the first of three double bonds of the aromatic ring system. 3-Dehydroquinate dehydratase has not been well studied in plant sources, but has been cloned from *E coli* (Duncan, et al., 1986, *Biochem. J.*, 238:485, the entirety of which is herein incorporated by reference).

Shikimate dehydrogenase (EC 1.1.1.25) catalyzes the NADPH-dependent conversion of dehydroshikimate to shikimate. Bifunctional dehydroquinate dehydratase (EC 4.2.1.10) shikimate dehydrogenase has been well studied in spinach, pea seedlings, and corn (Bentley 1990, *Critical Rev. Biochem. Mol. Biol.* 25: 307–384, Kishore and Shah 1988, *Ann. Rev. Biochem.*, 57:67–663, all of which are herein incorporated by reference in their entirety). The *E coli* enzyme is a monomeric, Monofunctional protein of Mr 32,000 (Chaudhuri and Coggins, 1985, *Biochem. J.*, 226:217–223, the entirety of which is herein incorporated by reference).

Shikimate kinase (EC 2.7.1.71) catalyzes the phosphorylation of shikimate to shikimate-3-phosphate. Shikimate kinase exists in isoforms in *E coli* and *S. typhimurium*, and plant shikimate kinase has been only partially purified from mung bean and sorghum (Bentley 1990, *Critical Rev. Biochem. Mol. Biol.* 25: 307–384, Kishore and Shah 1988, *Ann. Rev. Biochem.*, 57:67–663, all of which are herein incorporated by reference in their entirety).

5-Enolpyruvyl-shikimate-3-phosphate synthase catalyzes the reversible transfer of the carboxyvinyl moiety of phosphoenolpyruvate to shikimate-3-phosphate, yielding 5-enolpyruvyl-shikimate-3-phosphate, and is one of the most characterized enzymes of the aromatic pathway. 5-Enolpyruvyl-shikimate-3-phosphate synthase has assumed considerable importance as this enzyme is the major target for inhibition by the broad spectrum, nonselective, postemergence herbicide, glyphosate. Chemical modification studies indicate that Lys, Arg, and His residues are essential for activity of the enzyme (Kishore and Shah 1988, Ann. Rev. Biochem., 57:67–663, the entirety of which is herein incorporated by reference). 5-Enolpyruvyl-shikiimate-3-phosphate synthase has been isolated and chemically and kinetically well characterized from microbial and plant sources, including tomato, petunia, Arabidtapsis, and Brassica (Kishore and Shah 1988, *Ann. Rev. Biochem.*, 57:67–663, the entirety of which is herein incorporated by reference).

Chorismate synthase (EC 4.6.1.4) catalyzes the conversion of 5-enolpyruvyl-shikimate-3-phosphate to chorismic acid, and introduces the second double bond of the aromatic ring in a trans- 1,4-elimination of inorganic phosphorous. Chorismate is the last common intermediate in the biosynthesis of aromatic compounds via the shikimate pathway. Very litter is known plant chorismate synthase. Although the enzeme reaction involves no change in the oxidation state of the substrate, chorismate synthase from various sources is unusual in requiring a reduced flavin cofactor, $FMNH_2$ or $FADH_2$, for catalytic activity ((Bentley 1990, *Critical Rev. Biochem. Mol Biol.* 25: 307–384, Kishore and Shah 1988, *Ann. Rev. Biochem.*, 57:67–663, all of which are herein incorporated by reference in their entirety).

The next enzyme in the tocopherol biosynthetic pathway is chorismate mutase (EC 5.4.99.5), which catalyzes the conversion of chorismic acid to prephenic acid. Chorismic acid is a substrate for a number of enzymes involved in the biosynthesis of aromatic compounds. Plant chorismate mutase exists in two isoforms, chorismate mutase-1 and chorismate mutase-2, that differ in feed back regulation by aromatic amino acids (Singh et al., 1985, *Arch. Biochem. Biophys.*, 243: 374–384, Goers et al., 1984, *Planta*, 162: 109–116, and 117–124, all of which are herein incorporated by reference in their entirety). It has been suggested that chioroplastic chorismate mutase-1 may play a central role in the biosynthesis of aromatic amino acids as this enzyme is activated by Tyr and Phe. The cytosolic isozyme chorismate mutase-2 is not regulated by aromatic amino acids, and may play a role in providing the aromatic nucleus for synthesis of aromatic secondary metabolites including tocopherol (d'Amato et al., 1984, *Planta*, 162: 104–108, the entirety of which is herein incorporated by reference).

The branching from prephenic acid is extensive, and leads not only to Phe and Tyr, but also to a number of secondary metabolites. Tyrosine is synthesized from prephenate via either 4-hydroxyphenylpyruvate or arogenate. Both routes have been identified in plants. but the enzymes involved in tyrosine biosynthesis via arogenate have not been cloned or purified to homogeneity (Bentley 1990, *Critical Rev. Biochem. Mol. Biol.* 25: 307–384, the entirety of which is herein incorporated by reference).

The formation of 4-hydroxyphenylpyruvate from prephenate is catalyzed by prephenate dehydrogenase (EC 1.3.1.12 (AND-specific) and EC 1.3.1.13 (NADP specific)).

4-Hydroxyphenylpyruvate for tocopherol biosynthesis may also come from tyrosine pool by the action of tyrosine transaminase (EC 2.6.1.5) or L-amino acid oxidase (EC 1.4.3.2). Tyrosine transaminase catalyzes the pyridoxal-phosphate-dependent conversion of L-tyrosine to 4-hydroxyphenylpyruvate. This reversible enzyme reaction transfers the amino group of tyrosine to 2-oxoglutarate to form 4-hydroxyphenylpyruvate and glutamate. L-Amino acid oxidase catalyzes the conversion of tyrosine to 4-hydroxyphenylpyiuvate by acting on the amino group of tyrosine, with oxygen as acceptor. This enzyme is not specific to tyrosine. In *E coli*, aromatic amino acid amino transferase (EC 2.6.1.57), which converts 4-hydroxyphenylpyruvate to tyrosine, plays a major role in Phe and Tyr biosynthesis. An Asp aminotransferase or transaminase A (EC 2.6.1.1) has broad specificity, and will utilize phenylpyruvate of p-hydroxyphenylpyruvate to form Phe and Tyr, respectively.

The precursor molecule homogentisic acid is produced from the shikimate pathway intermediate p-hydroxyphenylpyruvate p-Hydroxyphenylpyruvate dioxygenase (EC 1.13.11.27) catalyzes the formation of homogentisate from hydroxyphenylpyruvate through an oxidative decarboxylation of the 2-oxoacid side chain of the substrate, accompanied by hydroxylation of the aromatic ring and a 1,2 migration of the carboxymethyl group. Norris et al. reported functional identification of the pdsI gene as encoding p-hydroxyphenylpyruvate dioxygenase (Norris et al., 1995, *Plant Cell* 7: 2139–2149, the entirety of which is herein incorporated by reference) p-hydroxyphenylpyruvate dioxygenase has been cloned from Arabidopsis and carrot (GenBank accession #U89267, AF000228, U87257). Fiedler et al. reported the localization and presence of this enzyme in both isolated spinach chloroplasts and peroxisomes (Fiedler et al., 1982, *Planta*, 155: 511–25 515, the entirety of which is herein incorporated by reference). Garcia et al. purified and cloned a cytosolic form of hydroxyphenylpyruvate dioxygenase from cultured carrot protoplasts (Garcia et al., 1997 *Biochem. J.* 325: 761–769, the entirety of which is herein incorporated by reference). These reports suggest that there exists two forms of hydroxyphenylpyruvate dioxygenase in chloroplasts and peroxisomes: the chloroplastic isoform would be involved in the biosynthesis of prenylquinones, and the peroxisomal and cytosolic isoform would be involved in the degradation of tyrosine.

2) Synthesis of Phytylpyrophosphate and Phytyl/Prenyl Transfer to Homogentisate

Carbon flow to phytol occurs via plastidic, non-mevalonate (Rohmer) and cytosolic, mevalonate pathways. Geranylgeranylpyrophosphate synthase (EC 2.5.1.29) catalyzes the formation of geranylgeranyl-pyrophosphate by condensation of isoprene moieties. The gene encoding geranylgeranylpyrophosphate synthase has been cloned from *Arabidopsis* and *Cantharanthus roseus* (Zhu et al., 1997, *Plant Cell Physiol.* 38: 357–361, Bantignies et al., 1995, *Plant Physiol.* 110: 336–336, the disclosures of which are each herein incorporated by reference in their entirety). This enzyme-synthesized geranylgeranylpyrophosphate pool splits for use in carotenoid and tocopherol biosynthesis, as well as for other isoprenoid compounds.

The NADPH-dependent hydrogenation of geranylgeranylpyrophosphate is catalyzed by geranylgeranylpyrophosphate hydrogenase (no EC number available, also called geranylgeranylpyrophosphate reductase) to form phytylpyrophosphate (Soll et al., 1983, *Plant Physiol.* 71: 849–854, the entirety of which is herein incorporated by reference). This enzyme appears to be localized in two sites: one in the chloroplast envelope for the hydrogenation of geranylgeranylpyrophosphate to the phytyl moiety, and the other in the thylakoids for the stepwise reduction of chlorophyll esterified with geranylgeraniol to chlorophyll esterified with phytol. The chloroplast envelope-located geranylgeranylpyrophosphate hydrogenase has been implicated to play a role in tocopherol and phylloquinone synthesis. The ChlP gene cloned from Synechocystis has been functionally assigned, by complementation in *Rhodobactor sphaeroides*, to catalyze the stepwise hydrogenation of geranylgeraniol moieties to phytol moieties (Addlesse et al., 1996, *FEBS Lett.* 389: 126–130, the entirety of which is herein incorporated by reference).

Homogentisate:phytyl transferase (no EC number available) catalyzes the decarboxylation, followed by condensation, of homogentisic acid with the phytol moiety of phytylpyrophosphate to form 2-methyl-6-phytyl- benzoquinol. The existence of this prenyltrnsferase activity has been demonstrated in spinach chloroplasts, and the activity is believed to be located in chloroplast envelope membranes (Fiedler et al., 1982, *Planta*, 155: 511–515, the entirety of which is herein incorporated by reference). A possible prenyltransferase gene, termed the pdsII mutant, specific to tocopherol biosynthesis, has been identified by Norris et al from a T-DNA-tagged population of Arabidopsis (Norris et al., 1995, *Plant Cell* 7: 2139–2149, the entirety of which is herein incorporated by reference).

3) Cyclization

Tocopherol cyclase catalyzes the cyclization of 2,3-dimethyl-5-phytylbenzoquinol to form γ-tocopherol, and plays a key role in the biosynthesis of the enantioselective chromanol substructure of the vitamin E subfamily (Stocker et al., 1996, *Bioorg. Medic. Chem.* 4: 1129–1134). Regarding its substrate specificity, it is not clear whether the enzyme prefers 2,3-dimethyl-5-phytylbenzoquinol or 2-methyl-6-phytylbenzoquinol. If the enzyme is specific to the former substrate, then 2-methyl-6 phytylbenzoquinol formed from prenyl-transferase requires methylation by an S-adenosylmethionine-dependent methyltransferase prior to cyclization. Tocopherol cyclase has been purified from the green algae *Chlorella protothecoides* and *Dunaliella salina*, and from wheat leaves (U.S. Pat. No. 5,432,069).

4) Methylation

Synthesis of γ-tocopherol from 2-methyl-6- phytylbenzoquinol occurs by two pathways, with either δ-tocopherol or 2,3-dimethyl-5-phytylbenzoquinol as an intermediate. α-tocopherol is then synthesized from γ-tocopherol in the final methylation step with S-adenosylmethionine. All the steps of α-tocopherol biosynthesis are located in the chloroplast membrane in higher plants. Formation of α-tocopherol from other tocopherols occurs due to S-adenosylmethionine (SAM)-dependent γ-tocopherol methyltransferase (EC 2.1.1.95). This enzyme has been partially purified from *Capsicum* and *Euglena gracilis* (Shigeoka et al., 1992, *Biochim. Biophys. Acta*, 1128: 220–226, d'Harlingue and Camara, 1985, *J. Biol. Chem.* 260: 15200–15203, the contents of both of which are herein incorporated by reference in their entirety).

Biosynthesis of Tocotrienols

The tocotrienols are similar to the tocopherols in molecular structure, except that there are three double bonds in the isoprenoid side chain. Although tocotrienols are not detected in soybean, they are widely distributed in plant kingdom. The tocotrienol biosynthetic pathway is similar to that of tocopherol up to the formation of homogentisic acid; the subsequent biosynthetic pathway leading to tocotrienols is not known. One of two possibilities is that the phytyl/prenyltransferase is able to transfer GGPP (geranylgeranylpyrophosphate) to homogentisic acid, and the other possibility is that the side chain is desaturated after the addition of phytylpyrophosphate to homogentisate. However, evidence from a study by Stocker indicates that reduction of the side chain's double bond occurs at an earlier stage of the biosynthesis, that is, either phytylpyrophosphate or GGPP (geranylgeranyl-pyrophosphate) is condensed with HGA (homogentisic acid) to yield different hydroquinone precursors that are cyclized by the same enzyme (Stocker, A., Fretz, H., Frick, H., Ruttimann., and Woggon, W.-D. *Bioorg. Medicinal Chem.*, 1996, 4:1129–1134, the entirety of which is herein incorporated by reference).

Regulation of Tocopherol Biosynthesis

Tocopherol levels vary in different plants, tissues, and developmental stages, indicating a highly regulated biosynthetic pathway. The production of homogentisic acid by p-hydroxyphenylpyruvate dioxygenase is likely to be a key regulatory point for bulk flow through the pathway because of irreversible enzyme action and because homogentisic acid production is the first committed step in tocopherol biosynthesis (Norris et al., 1995, *Plant Cell* 7: 2139–2149, the entirety of which is herein incorporated by reference). The other key regulatory step in tocopherol biosynthesis is the availability of the phytylpyrophosphate pool. Feeding studies (Fury et al., 1987, *Phytochem.*, 26: 2741–2747, the entirety of which is herein incorporated by reference) in safflower callus culture demonstrated 1.8-fold and 18-fold increases in tocopherol synthesis by feeding homogentisate and phytol, respectively. In meadow rescue leaf, vitamin E increases in the initial phase of foliar senescence when phytol is cleaved off from the chlorophylls and when free phytol is available (Peskier et al., 1989, *J. Plant Physiol.* 135: 428432, the entirety of which is herein incorporated by reference). These reports suggest tight coupling of tocopherol biosynthesis to the availability of homogentisic acid and phytol.

A summary of the enzymes involved in tocopherol biosynthesis is provided in Table 1.

TABLE 1

Enzymes of the Tocopherol Biosynthetic Pathway

| Enzyme | EC Number |
| --- | --- |
| 3-Deoxy-D-arabino-heptulosonate-7-P-synthase (DAHP synthase) | 4.1.2.15 |

TABLE 1-continued

Enzymes of the Tocopherol Biosynthetic Pathway

| Enzyme | EC Number |
| --- | --- |
| 3-Dehydroquinate synthase | 4.6.1.3 |
| 3-dehydroquinate dehydratase | 4.2.1.10 |
| Shikimate dehydrogenase | 1.1.1.25 |
| Shikimate kinase | 2.7.1.71 |
| 5-enoylpyruvyl-shikimate-3-P-synthase (EPSPS) | 2.5.1.19 |
| Chorismate synthase | 4.6.1.4 |
| Chorismate mutase | 5.4.99.5 |
| Prephenate dehydrogenase-NAD specific | 1.3.1.12 |
| Prephenate dehydrogenase-NADP specific | 1.3.1.13 |
| Tyrosine transaminase | 2.6.1.5 |
| Aromatic amino acid transaminase | 2.6.1.57 |
| Transaminase A | 2.6.1.1 |
| L-Amino-acid oxidase | 1.4.3.2 |
| 4-Hydroxyphenylpyruvate dioxygenase (HPD or OHPP) | 1.13.11.27 |
| Geranylgeranylpyrophosphate synthase (GGPP Synthase) | 2.5.1.29 |
| Geranylgeranylpyrophosphate hydrogenase | no EC # (GGH) |
| Homogentisate:phytyl transferase (Phytyl/Prenyltransferase) | no EC # |
| 2-methyl-6-phytylbenzoquinol methylase | no EC # |
| Tocopherol cyclase | no EC # |
| S-adenosyl methionine (SAM)-dependent γ-tocopherol methyltransferase (GTMT or tocopherol O-methyltransferase) | 2.1.1.95 |

Nucleic acids (genomic DNA, plasmid DNA, cDNA, syshetic DNA, mRNA, etc.) encoding enzymes listed in Table 1 adove, or amino acid sequences of the purified enzymes, which permit desing of nucleidec acid probes facilitating the isolation of DNA coding sequences thereof, are known in the art and are available for use in the methods of the present invention as variously indicated by the GenBank accessions listed in Table 2 below. It is generally recognized to an artisan skilled in the field to winch the present invention pertains that the examples show in Table 2 may be used to insolated other potential tocopherol biosynthesis genes from GenBank using DNA and peptide search techniques generally known in the art.

TABLE 2

1. DHAP synthase (EC 4.1.2.15)
*A. thaliana* 3 deoxy-D-arabino-heptulosonate y-phosphate synthase (DHS1) mRNA, complete cds
gi|166687|gb|M74819
*E. coli* aroF gene for DAHP synthase (Tyr), complete coding sequence
gi|145361|gb|K01989
*S. cerevisiae* aro4 gene for DAHP-Synthase (EC 4.1.2.15)
gi|416186|emb|X61107
2. 3-Dehydroquinate synthase (EC 4.6.1.3)
*Pseudomonas aeruginosa* dehydroquinate synthase (aroB) gene, partial cds
gi|309861|gb|L13866
*E. coli* aroB gene for 3-dehydroquinate synthase (EC 4.6.1.3)
gi|40967|emb|X03867
3. 3-Dehyroquinate dehydratase (4.2.1.10)
*Nicotiana tabacum* (clone: SP-3) dehydroquinate dehydratase/shikimate dehydrogenase (aroD-E) mRNA, 3' end gi|535770|gb|L32794
*Neisseria gonorrhoeae* dehydroquinate dehydratase (aroD) gene and recA gene, partial cds
gi|1143313|gb|U39803
4. Shikimate dehydrogenase (EC 1.1.1.25)
*Escherichia coli* aroE gene for shikimate dehydrogenase (EC 1.1.1.25)
gi|40977|emb|Y00710
*Neisseria meningitidis* shikimate dehydrogenase (aroE) gene, complete cds
gi|1785881|gb|U82835
5. Shikimate kinase (EC 2.7.1.71)
*Escherichia coli* shikimic acid kinase I (aroK) gene, complete cds
gi|662834|gb|L39822
*E. coli* aroL gene for shikimate kinase II (EC 2.7.1.71)

TABLE 2-continued

*L. esculentum* mRNA for shikimate kinase precursor
gi|19348|emb|X63560
6. EPSP Synthase (EC 2.5.1.19)
Petunia 5-enolpyruvylshikimate-3-phosphate synthase (EPSP synthase) gene, 5' end
gi|169212|gb|M37029
*E. coli* gene aroA for 5-enolpyruvylshikimate 3-phosphate synthase (EPSP synthase, EC 2.5.1.19, alternative name 3-phosphoshikimate 1-carboxyvinyltransferase)
gi|40965|emb|X00557
*Brassica napus* 5-enolpyruvylshikimate-3-phosphate synthase gene
gi|17814|emb|X51475
*Z. mays* mRNA for EPSP-synthase
gi|1524382|emb|X63374
7. Chorismate synthase (EC 4.6.1.4)
*L. esculentum* chorismate synthase 2 precursor
gi|410483|emb|Z21791l
*L. esculentum* chorismate synthase 1 precursor
gi|410481|emb|Z21796
*E. coli* aroC gene for chorismate synthase (EC 4.6.1.4)
gi|40969|emb|Y00720
8. Chorismate mutase (5.4.99.5)
*A. thaliana* mRNA for chorismate mutase
gi|429152|emb|Z26519
*E. coli* chorismate mutase/prephenate dehydratase (pheA) gene, 5' end of cds, and leader peptide, complete cds gi|147178|gb|M58024
9. Prephenate dehydrogenase (1.3.1.12 and 1.3.1.13)
*Erwinia herbicola* prephenate dehydrogenase (tyrA) gene, partial cds
gi|415009|gb|M74135
10. Tyrosine transaminase (2.6.1.5)
*E. coli* K12 tyrB gene encoding aminotransferase, complete cds
gi|148084|gb|M12047
*H. sapiens* mRNA for tyrosine aminotransferase
gi|37501|emb|X55675
11. 4-Hydroxyphenylpyruvate dioxygenase (1.13.11.27)
*Hordeum vulgare* mRNA for 4-hydroxyphenylpyruvate dioxygenase
gi|2695709|emb|AJ000693
*H. sapiens* mRNA for 4-hydroxyphenylpyruvate dioxygenase
gi|288104|emb|X72389
*Daucus carota* 4-hydroxyphenylpyruvate dioxygenase mRNA, complete cds
gi|2231614|gb|U87257
*Mycosphaerella graminicola* 4-hydroxyphenylpyruvate dioxygenase (HPPD) gene, complete cds
gi|2708689|gb|AF038152
12. Gernaylgeranyl dehydrogenase
Synechocystis sp. PCC6803 chlP gene
gi|1332618|emb|X97972
13. Geranylgeranyl pyrophosphate synthase (2.5.1.29)
*Arabidopsis thaliana* mRNA for geranylgeranyl pyrophosphate synthase, partial cds
gi|1944370|dbj|D85029
*E. herbicola* phytoene synthase (crtE) gene, complete cds
gi|148399|gb|M38424

In addition to the foregoing sources, PCT International Publication WO 97/27285 discloses cDNA encoding Arabidopsis 4-hydroxyphenylpyruvate dioxygenase (HPD or OHPP). Further sources include Fuqua et al. (1991) Gene 109:131–136, and Ruzafa et al. (1994) FEMS *Microbiology Letters* 124:179–184. U.S. Pat. No. 5,432,069 discloses purified, homogeneous tocopherol cyclase isoiated from *Chlorella protothecoides*, *Dunaliella salina*, and wheat leaves. FIG. 16 herein shows a DNA sequence encoding geranylgeranylpyrophosphate hydrogen in maize; FIG. 17 shows the deduced amino acid sequence.

In addition to the foregoing sequences, DNA coding sequences useful in the present invention can be derived from algae, fungi, bacteria, mammalian sources, plants, etc. Homology searches in existing databases using signature sequences corresponding to the active sites of enzymes, e.g., the geranylgeranylation sequence for geranylgeranyl-pyrophosphate hydrogenase, the iron binding site for 4-hydroxyphenylpyruvate dioxygenase, the S-adenosylmethionine binding regions for methyl transferases, etc., can be employed to isolate equivalent, related genes from other sources such as plants and microorganisms. Searches in EST databases can also be employed. Furthermore, the use of DNA sequences encoding enzymes functionally enzymatically equivalent to those disclosed herein, wherein such DNA sequences are degenerate equivalents of the nucleic acid sequences disclosed herein in accordance with the degeneracy of the genetic code, is also encompassed by the present invention. Demonstration of the functionality of coding sequences identified by any of these methods can be carried out by complementation of mutants of appropriate organisms, such as Synechocystis, Shewanella, yeast, Pseudomonas, Rhodobacteria, etc., that lack specific biochemical reactions, or that have been mutated. The sequences of the DNA coding regions can be optimized by gene resynthesis, based on codon usage, for maximum expression in particular hosts.

Transformation of plants with structural DNA coding sequences that permit overexpression of enzymes that enhance the pools of subtrates which contribute to the tocol and the phytol moieties of tocophrerols and tocotrienols can be used to increase the biosynthetic activity of the tocopherol pathway, and can lead to increased production of particular tocopherol isomers, such as, for example, α-tocopherol, etc. One objective, for example, is to express coding sequences that enhance carbon flux for the formation of homogentisate and phytol, as well as those that encode methyl transferase(s) in oil accumulating tissues of plants. Formation of α-tocopherol from other tocopherols occurs due to S-adenosylmethionine, (SAM)-dependent methylases such as γ-tocopherol methyl transferases. Overexpression of methylase(s) in combination with the other approaches described herein is also contemplated in the present methods. Thus, any of the DNAs encoding enzymes of the tocopherol biosynthetic pathway, discussed above, are useful in the present invention. Transformation of plants with an early tocopherol biosynthesis gene is sufficient to produce seeds having an elevated level of tocopherols. By "early tocopherol biosynthesis gene" is meant DNA encoding geranylgeranyl-pyrophosphate synthase, geranylgeranylpyrophosphate hydrogenase, 4-hydroxyphenylpyruvate dioxygenase, and phytyl/prenyl transferase. DNA encoding enzymes active in later steps of tocopherol biosynthesis ("secondary tocopherol biosynthesi's genes") can be expressed to enhance carbon flux thru the tocopherol pathway even further, and to produce specific tocopherol isomers. In this way, the tocopherol biosynthetic pathway can be modified to enhance production of any tocopherol compound of interest, such as α-tocopherol. As noted above, a variety of sources are available for the early tocopherol biosynthesis genes (and other tocopherol biosynthesis genes), and a gene from any of these sources can be utilized. If co-suppression occurs when a plant gene native to the target host plant is used to increase expression of a particular enzyme, a coding sequence from another source can be used as an alternative.

Oil comprising the tocopherols produced by the methods disclosed herein can be extracted from seeds to provide a valuable source of tocopherols. Alternatively, seeds with increased levels of tocopherols, or fruits and vegetables with increased levels of tocopherols, can be used directly. Preferred genes for introduction into plants to alter tocopherol quantity/quality include 3-deoxy-D-arabino-heptulosonate-7-P synthase (DAHP synthase), shikiimate kinase, either or both of the prephenate dehydrogenases, 4-hydroxy-phenylpyruvate dioxygenase (OHPP or HPD), γ-tocopherol methyltransferase (GTMT), geranylgeranylpyrophosphate synthase (GGPP synthase), geranylgeranylpyrophosphate hydrogenase (GGH), phytyl/prenyltransferase, 2-methyl-6-phytylbenzoquinol methyl transferase, tocopherol cyclase, and γ-tocopherol methyltransferase (GTMT). 4-hydroxyphenylpyruvate dioxygenase and geranylgeranylpyrophosphate hydrogenase will increase the homogentisate and phytol pools, respectively. Enzymes that control fluxes through pathways are well known to be regulated in higher organisms such as plants. Therefore, 4-hydroxyphenylpyruvate diooxygenase and geranylgeranylpyrophosphate hydrogenase genes of microbial origin which are not subject to regulation in plants, or those from higher organisms (plants, algae, fungi, etc) that are deregulated, are especially attractive in this regard. Overexpression of enzymes such as 3-deoxy-arabino-heptulosonate 7-P (DAHP) synthase, prephenate dehydrogenase, and Shikimate kinase would lead to increases in the levels of homogentisate. DNA encoding any of the tocopherol biosynthetic enzymes discussed herein can be introduced alone or in various combinations to enhance tocopherol quantity and/or alter tocopherol quality. When introduction of multiple enzymes is desirable, preferred combinations include, but are not limited to, 4-hydroxyphenylpyruvate dioxygenase (OHPP or HPD) plus geranylgeranylpyrophosphate hydrogenase (GGH), and geranylgeranylpyrophosphate synthase (GGPP synthase) plus geranylgeranylpyrophosphate hydrogenase (GGH).

To increase tocotrienol levels, antisensing geranylgeranylpyrophosphate hydrogenase can lead to increased pools of geranylgeranyl-pyrophosphate. Such elevated pools of geranylgeranylpyrophosphate can be used by a phytyl/prenyl transferase to lead to increased production of tocotrienols.

Figure 18:
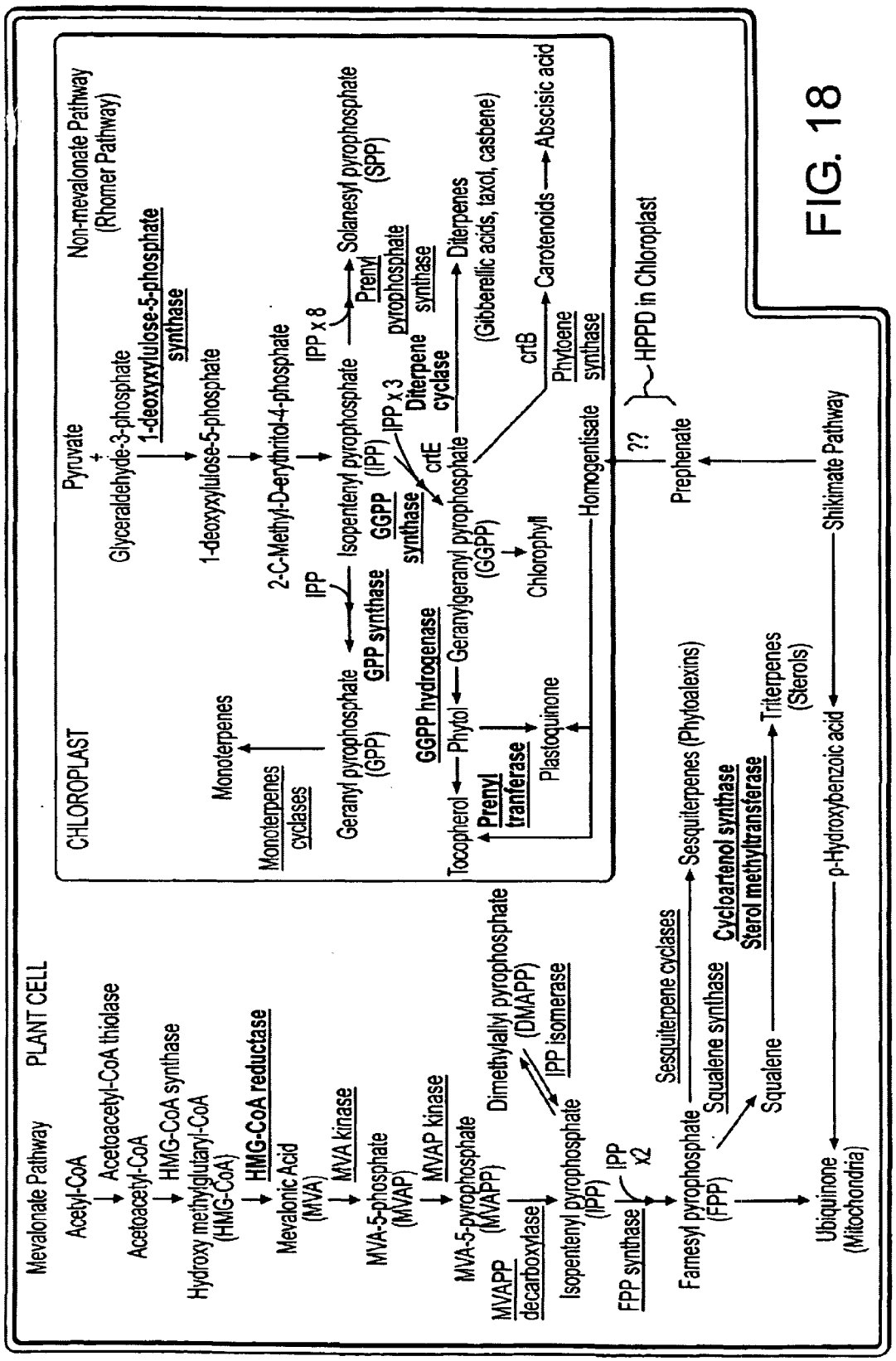
FIG. 18 shows plant cell and chloroplast carotenoid and tocopherol biosynthetic pathways.

In addition to the foregoing methods, other methods of enhancing the levels of tocopherol and tocopherol isomers in plants include the following:

Reducing the Flow of Acetyl-CoA to Fatty Acids by Tissue-specific Anti-sensing/Cosuppressing Acetyl-CoA Carboxylase and Pyruvate Dehyydrogenase to Enhance the Pools of Aacetyl-CoA and Pyruvate for Phytol Biosynthesis Carbon flow to phytol occurs via plastidic, non-mevalonate (Rohmer) and cytosolic, mevalonate pathways. Note FIG. 18. For example, the seed plastidic compartment is the major source for acetyl-CoA, which is the starting metabolite for sterols, fatty acids, quinones, etc. Reducing the flow of acetyl-CoA to fatty acids by tissue-specific antisense inhibition and/or cosuppression of acetyl-CoA carboxylase and pyruvate dehydrogenase subunits would elevate the pools of acetyl-CoA and pyruvate available for phytol biosynthesis. DNA coding sequences useful in this methodi include, but are not limited to, GenBank accession numbers L42814 (soybean acetyl-CoA carboxylase) and U80186 (*Arabidopsis thaliana pyruvate* dehydrogenaseE1 β subunit mRNA genomic coding sequence).

Overexiressing the Rohmer Pathway With or Without Concomitant GGH Overexpression to Enhance the Conversion of Pyruvate to Phytol Conversion of pyruvate to phytol can be enhanced by overexpressing enzymes of the non-mevalonate, plastidic Rohmer pathway (FIG. 18), with or without concomitant geranylgeranyl-pyrophosphate hydrogenase overexpression. This pathway, known to be present in plastids, converts pyruvate and glyceraldehyde-3-phosphate to isopentenyl pyrophosphate (IPP) through a series of reactions. The gene for the first of these steps, i.e., the synthesis of 1-deoxyxylulose-5-phosphate, catalyzed by 1-deoxyxylulose-5-phosphate synthase (dxs), has been cloned from *E coli* (GenBank accession number AF035440) and *Oryza sativa* (GenBank accession number AF024512). Overexpression of 1-deoxyxylulose-5-phosphate synthase in transgenic plants will increase isopentenyl pyrophosphate synthesis in plastids. Concomitant overexpression of geranylgeranylpyrophosphate hydrogenase, which is involved in the terminal step of phytol biosynthesis, will also lead to increased levels of tocopherol.

All the methods described above for enhancement of carotenoid biosynthesis in transgenic plants apply equally well in the case of the modifications to the tocopherol biosynthetic pathway described herein, and are intended to be applied thereto as well.

In particular, appropriate target plant tissues for enhanced tocopherol production include, but are not limited to, seeds, flowers, fruits, roots, leaves, and other vegetable. parts of plants. Within seeds, appropriate cellular compartments include, but are not limited to, the cell cytoplasm, and plastids. Within leaves, appropriate cellular compartments include, but are not limited to, the cell cytoplasm and plastids as well. Targeting of enzymes involved in altering tocopherol quantity and/or quality to plastids can be achieved by fusing DNA encoding plastid, e.g., chloroplast, leucoplast, amyloplast, etc., transit peptide sequences to the 5'-ATG of DNAs encoding tocopherol biosynthetic enzymes. Such transit peptide sequences include, but not limited to, those from RUBP carboxylase, EPSP synthase, fatty acyl-ACP thioesterases, etc. Other transit peptide sequences useful in the present invention are disclosed in Von Heijne et al., (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481. Plant tocopherol genes useful in the invention may utilize native or heterologous transit peptides.

Promoters useful in altering tocopherol quantity and/or quality in transgenic plants include promoters that confer appropriate cellular and temporal specificity of expression. Such promoters include those that are constitutive or inducible, environmentally- or developmentally-regulated, or cell- or tissue-specific. Useful seed-specific promoters include, but are not limited to, the napin, phaseolin, zein, soybean trypsin inhibitor, 7S, ADR12, ACP, stearoyl-ACP desaturase, oleosin, and Lasquerell hydroxylase promoters. Seed-specific gene regulation is discussed in EP 0 255 378. Useful embryo-specific promoters include the corn globulin 1 and oleosin promoters. A useful endosperm-specific promoter is the glutelin promoter. Useful constitutive promoters for leaf-specific expression include the CaMV 35S and enhanced 35S promoters, the Figwort Mosaic Virus (FMV) promoter, the mannopine synthase (mas) promoter, the nopaline synthase (nos) promoter, and the octopine synthase (ocs) promoter. Fruit specific promoters useful in the present invention include the E4 promoter (Cordes et al. (1989) *Plant Cell* 1:1025–1034), the E8 promoter (Deikman, et al. (1988) *EMBO J.* 7(11):3315–3320), the kiwifruit actinidin promoter (Lin, et al. (1993) *Proc Natl Acad Sci*, 90(13) :5939–5943) and the 2A 11 promoter (Houck, etal. U.S. Pat. No. 4,943,674). Useful inducible promoters include heat-shock promoters, hormone-inducible promoters, and light-inducible promoters. Promoter hybrids can also be constructed to enhance transcriptional activity (Hoffman, U.S. Pat. No. 5,106,739), or to combine desired transcriptional activity and tissue specificity. Plants suited to the tocopherol modifications discussed herein include, but are not limited to, various monocots and dicots, including high oil seed plants such as high oil seed Brassica (e.g., *Brassica napus, Brassica rapa, Brassica campestris, Brassica carinata*, and *Brassica juncea*), soybean (*Glycine max*), cotton, safflower, sunflower (*Helianthus annuus*), flax (*Linum usitatissimum*), corn (*Zea mays*), coconut, palm, and peanut, as well as tobacco, wheat, barley, rice, oats, amaranth, potato, rice, tomato, and legumes (e.g., peas, beans, lentils, alfalfa, etc.).

Plant transformation vectors capable of delivering DNAs (genomic DNAs, plasmid DNAs, cDNAs, or synthetic DNAs) encoding tocopherol and/or carotenoid biosynthetic enzymes for optimizing substrate pools for tocopherol biosynthesis can be easily designed by art-recognized methods. Various strategies can be employed to introduce these encoding DNAs to produce transgenic plants capable of biosynthesizing high levels of tocopherols and/or carotenoids, including:

1. Transforming individual plants with an encoding DNA of interest. Two or more transgenic plants, each containing one of these DNAs, can then be grown and cross-pollinated so as to produce hybrid plants containing the two DNAs. The hybrid can then be crossed with the remaining transgenic plants in order to obtain a hybrid plant containing all DNAs of interest within its genome.

2. Sequentially transforming plants with plasmids containing each of the encoding DNAs of interest, respectively:

3. Simultaneously cotransforming plants with plasmids containing each of the encoding DNAs, respectively, 4. Transforming plants with a single plasmid containing two or more encoding DNAs of interest.

5. Transforming plants by a combination of any of the foregoing techniques in order to obtain a plant that expresses a desired combination of encoding DNAs of interest.

Traditional breeding of transformed plants produced according to any one of the foregoing methods by successive rounds of crossing can then be carried out to incorporate all the desired encoding DNAs in a single homozygous plant line (Nawrath et al. (1994) *Proc. Natl Acad. Sci. USA* 91: 12760; PCT International Publication WO 93/02187).

In methods 2 and 3, the use of vectors containing different selectable marker genes to facilitate selection of plants containing two or more different encoding DNAs is advantageous. Examples of useful selectable marker genes include those conferring resistance to kanamycin, hygromycin, sulphonamides, glyphosate, bialaphos, and phosphinothricin.

The following examples are offered by way of illustration and not by way of limitation.

EXPERIMENTAL

EXAMPLE 1

Expression Construct and Plant Transformation

A. SSU Fusions to *E. uredovora* Carotenoid Biosynthesis Genes (1) Phytoene Synthase The SSU leader and crtB gene sequences were joined by PCR. The sequence of the SSU/crtB fusion is shown in FIGS. 1A and 1B. The crtB gene from nucleotides 5057 to 5363 (numbering according to Misawa et al. (1990) supra was joined to the SSU leader as follows. A BglII site was included upstream of the SSU leader start site to facilitate cloning. The thymidine nucleotide at 5057 of crtB was changed to an adenosine to make the first amino acid at the SSU leader/crtB junction a methionine, and the splice site a cys-met-asn. The native splice site for SSU is cys-met-gln. Note that Misawa et al. (1990) supra) indicates that the start site for the coding region for crtB is at nucleotide 5096.

Thus, there are 13 amino acids upstream of the published start of the coding region for crtB and after the SSU splice site in the crtB/SSU fusion. Twelve of these amino acids are translated from Erwinia crtB upstream sequence and one is the added methionine. The crtB from 5363 (EcoRV) to 6009 (EcoRI) was then attached to the SSU-crtB fusion to obtain a complete SSU-crtB fusion construct designated pCGN3373 (FIGS. 1A and 1B).

(2) Phytoene Desaturase

A plasmid comprising a *E. uredovora* crtI gene fused to the transit peptide sequence of the pea Rubisco small subunit was described by Misawa et al. (*The Plant Journal* (1993) 4:833–840. An approximately 2.1 kb XbaI/EcoRI fragment of this plasmid containing the SSU-crtI fusion and a nos 3' termination region was cloned in position for expression from a napin 5' promoter.

(3) GGPP Synthase

A similar construct containing the SSU transit fused to an *E. uredovora* crtE gene was obtained. The SSU-crtE fusion is present on an approximately 1.2 kb BglII/BamHI fragment in pCGN3360.

B. Expression Constructs for Plant Transformation (1) Phytoene Synthase pCGN3373 carrying the complete SSU/crtB fusion was cut with BglII and BamHI to excise the SSU/crtB fusion. The resulting fragment was ligated into the napin expression cassette in pCGN3223 at the BamHI site (see WO 94/10288 for description of napin expression cassette). The resulting construct, pCGN3389, was digested with HindIII to excise the napin 5'-SSU/crtB-napin 3' fragment, which was then cloned into HindIII cut pCGN1559PASS yielding pCGN3390. pCGN1559PASS is a binary vector for Agrobacterium-mediated transformation such as those described by McBride et al. (*Plant Mol. Biol.* (1990) 14:269–276) and is prepared from pCGN 1559 by substitution of the pCGN 1559 linker region with a linker region containing the following restriction digestion sites: Asp718/AscI/PacI/XbaI/BamHI/SwaI/Sse8387(PstI)/HindHIII. A map of pCGN3390 is provided in FIG. 2A.

(2) Phytoene Desaturase

A fragment comprising a napin 5'/SSU-crtI fusion/nos 3' construct as described above was cloned into a binary vector for plant transformation resulting in pCGN9010. A map of pCGN9010 is provided in FIG. 2C.

(3) GGPP Synthase pCGN3360 carrying the complete SSU/crtE fusion was cut with BglII and BamHI to excise the SSU/crtE fusion. The resulting 1.2 kb fragment was ligated into the napin expression cassette in pCGN3223 at the BamHI site. The resulting construct, pCGN3391, was digested with HindIII to excise the napin promoter-SSU/crtE napin 3' fragment, which was then cloned into HindIII cut pCGN1559PASS yielding pCGN3392. A map of pCGN3392 is provided in FIG. 2B.

(4) Phytoene Synthase+Phytoene Desaturase

Figure 2D:
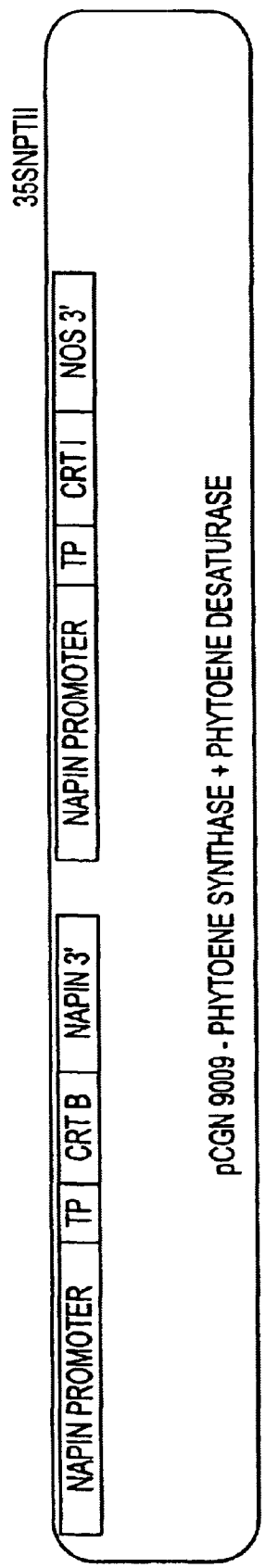

The napin5'-SSU/crtB-napin 3' fragment from pCGN3389 and the napin 5'/SSU-crtI fusion/nos 3' as present in pCGN9010 were inserted into a binary vector resulting in pCGN9009, shown in FIG. 2D.

(5) Antisense Epsilon Cyclase+Phytoene Synthase

Figure 2E:
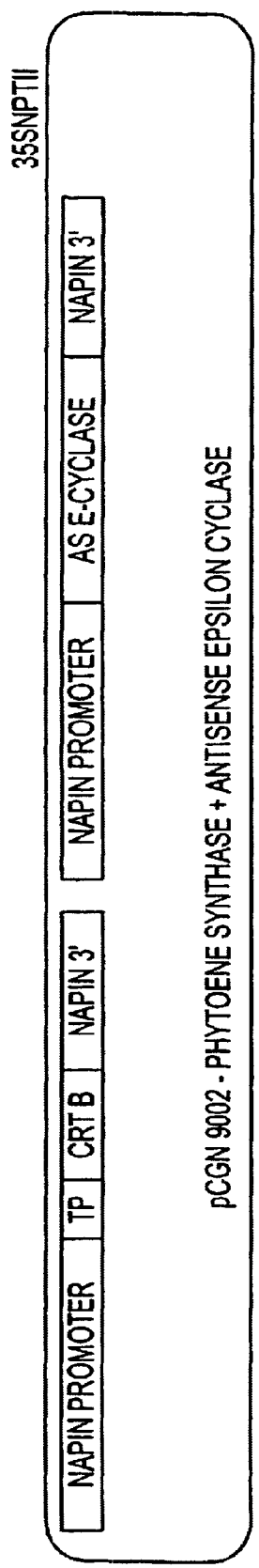
Figure 9A:
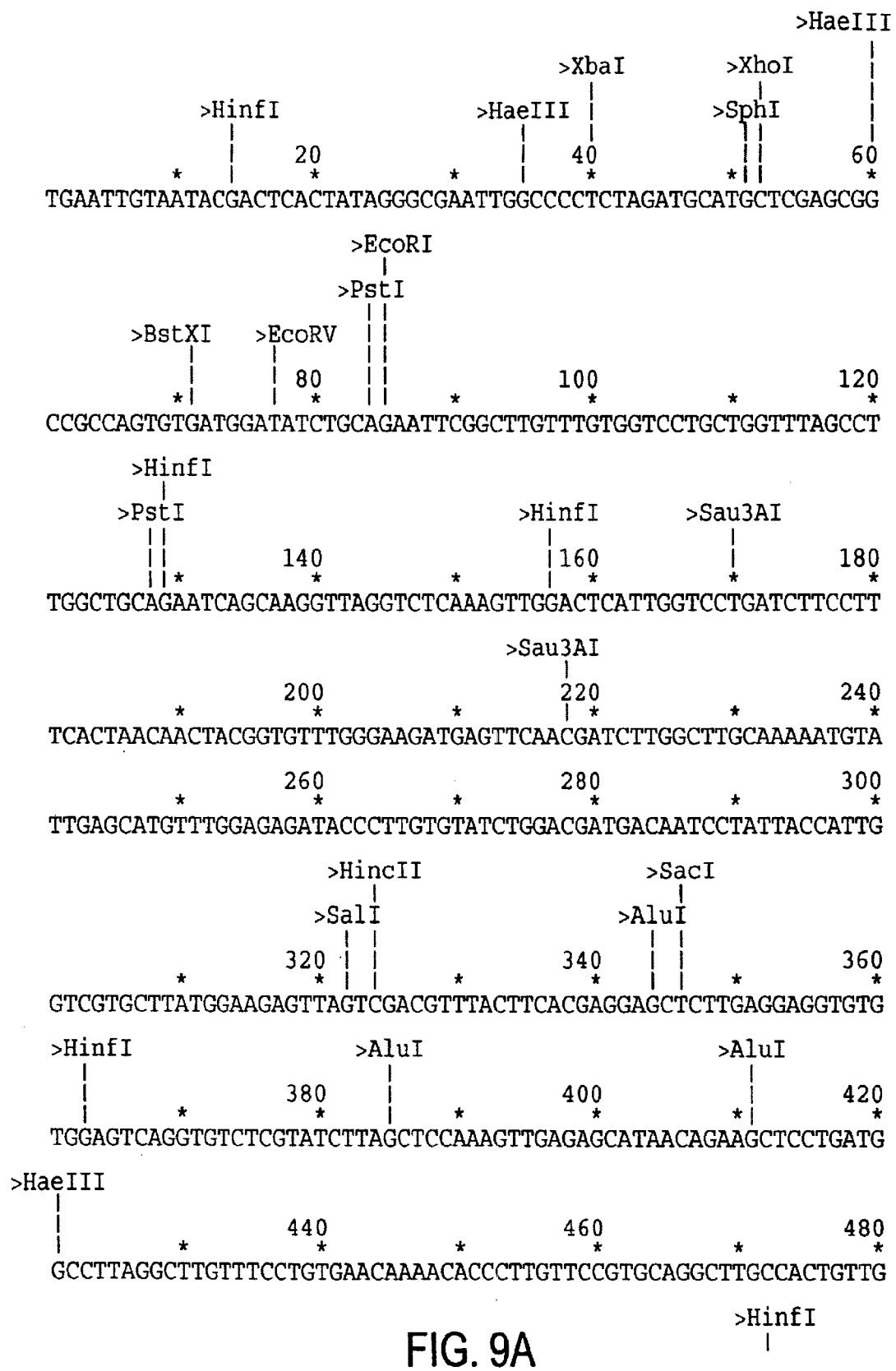
Figure 15:
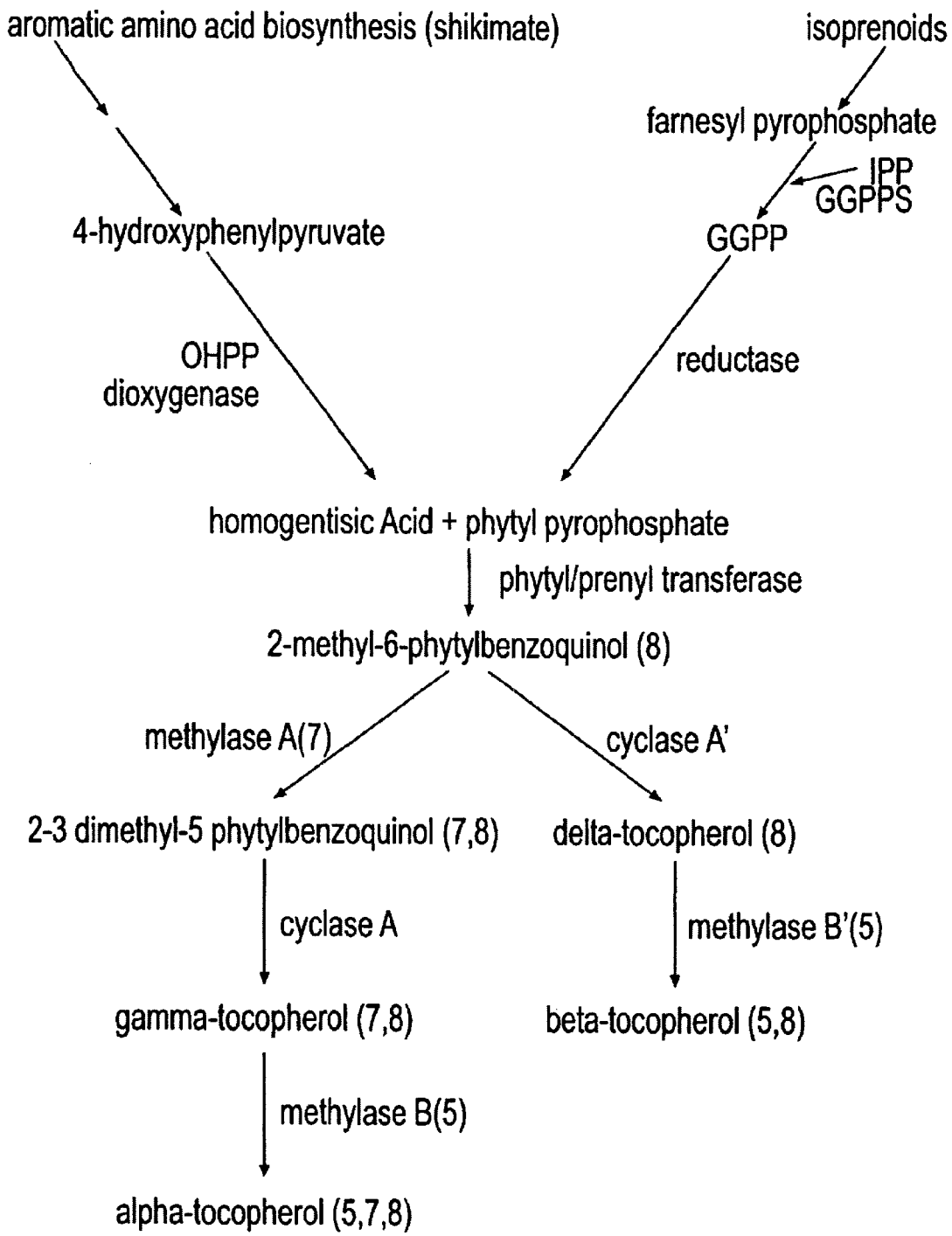
FIG. 15 shows a tocopherol biosynthetic pathway.

*Brassica napus* epsilon cyclase genes are isolated by PCR using primers designed from an Arabidopsis epsilon cyclase gene (Cunningham FX Jr (1996) *Plant Cell* 8:1613–1626). Sequence of *B. napus* epsilon cyclase genes is provided in FIGS. 9A and 9B (clone 9–4) and FIGS. 10A and 10B (clone 7–6). An antisense construct is prepared by cloning an XhoI/BamHI fragment of cDNA clone 9–4 into a napin expression cassette (pCGN3223) digested with XhoI and BglII. The napin 5'-antisense epsilon cyclase-napin 3' fragment is cloned along with a napin 5-SSU/crtB-napin 3' fragment, fragment into a binary vector for plant transformation, resulting in pCGN9002, shown in FIG. 2E.

(6) Antisense Beta Cyclase+Phytoene Synthase

Figure 2F:
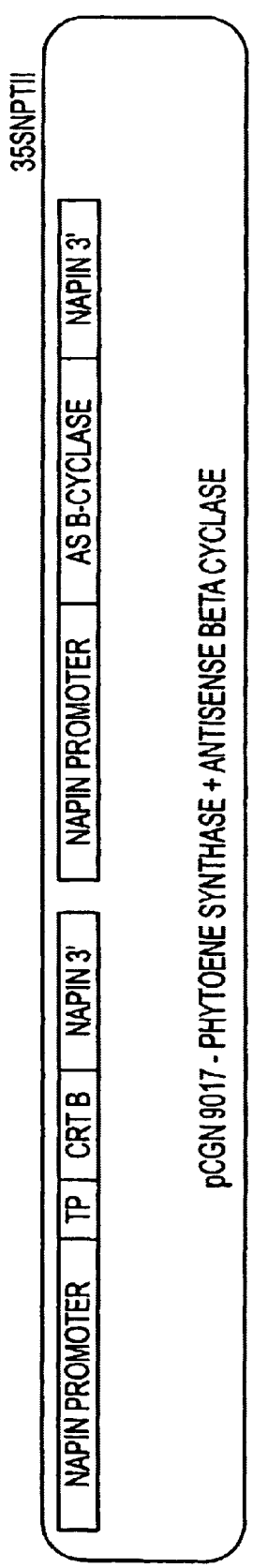

*Brassica napus* beta cyclase genes are isolated by PCR using primers designed from an Arabidopsis beta cyclase gene (Cunningham FX Jr (1996) *Plant Cell* 8:1613–1626). Sequence of a *B. napus* beta cyclase cDNA, 32–3, is provided in FIGS. 11A–11D. An antisense construct is prepared by cloning an XhoI fragment of the beta cyclase cDNA clone into a napin expression cassette (pCGN3223) digested with XhoI. A clone containing the beta cyclase in the antisense orientation is selected. The napin 5'-antisense beta cyclase-napin 3' fragment is cloned along with a napin 5-SSU/crtB-napin 3' fragment into a binary vector for plant transformation, resulting in pCGN9017, shown in FIG. 2F.

C. Plant Transformation

Transformed *Brassica napus* plants containing the above described constructs are obtained as described in Radke et al. (*Theor. Appl. Genet.* (1988) 75:685–694 and *Plant Cell Reports* (1992) 11:499–505).

Transformed cotton plants, *Gossypium hirsutum*, containing phytoene synthase may be obtained using methods described in issued U.S. Pat. Nos. 5,004,863, and 5,159,135, and in Umbeck et al. (1987) *Bio/Technology* 5:263–266, or as described in copending application 08/539,176.

EXAMPLE 2

Analysis of Transgenic Plants

A. Visual Observations and Segregation Ratios

The napin-SSU leader/crtB plants in 212/86 were tagged at 21 days, 28 days and 35 days post anthesis. When the first plant, 3390-1 was harvested at 28 days, some of the seeds were obviously orange. AT 35dpa, the orange was obvious enough that a segregation ratio could be obtained. This trend of orange seeds has continued and is seen in each of the 17 lines harvested that have been obtained. A table of the segregation ratios is included below in Table 3.

TABLE 3

| Generation | Plant # | Orange | Green | Ratio | Chi Square |
|---|---|---|---|---|---|
| T2 | 3390-1 | 291 | 88 | 3 to 1 | 0.64 |
| T2 | 3390-2 | 150 | 22 | No fit | |
| T2 | 3390-8 | 293 | 87 | 3 to 1 | 0.90 |
| T2 | 3390-4 | 277 | 82 | 3 to 1 | 0.89 |
| T2 | 3390-5 | 243 | 62 | 3 to 1 | 1.90 |
| T2 | 3390-7 | 236 | 89 | 3 to 1 | 0.99 |
| T2 | 3390-6 | 307 | 5 | 63 to 1 | 0.00 |
| T2 | 3390-3 | 121 | 50 | No fit | 1.64 |
| 12 | 3390-11 | 294 | 105 | 3 to 1 | 0.37 |
| T2 | 3390-15 | 287 | 83 | 3 to 1 | 1.30 |
| T2 | 3390-16 | 187 | 65 | 3 to 1 | 0.08 |
| T2 | 3390-17 | 105 | 104 | No fit | |
| T2 | 3390-12 | 119 | 28 | 3 to 1 | 2.78 |
| T2 | 3390-14 | 283 | 107 | 3 to 1 | 1.23 |
| T2 | 3390-19 | 238 | 94 | 3 to 1 | 1.94 |
| T2 | 3390-20 | 251 | 4 | 63 to 1 | 0.00 |
| T2 | 3390-27 | 229 | 4 | 63 to 1 | 0.04 |

B. Carotenoid Analysis of Developing Seeds

Carotenoids were extracted from seeds harvested at approximately 35 days post-anthesis as follows. Eight seed samples of orange seeds from transgenic plant 3390-1 and eight seed samples of a 212/86 variety rapeseed control plant were ground in 200 µl of 70% acetone/30% methanol. The ground seed mixture was then spun in a microcentrifuge for approximately minutes and the supernatant removed. Two additional 70% acetone/30% methanol extractions were conducted with the pelleted seed material and all three supernatants pooled and labeled A/M extract.

At this point in the extraction, the control seed pellets are white, whereas the seed pellets from the transgenic seeds have a yellow color. The pellets are then extracted twice with ether and the resultant supernatants pooled and labeled E extract. The A/M extract was then transferred to ether as follows. 450 µl ether and 600 µl of water were added to the extracts, followed by removal of the ether layers. The A/M extracts were then washed two more time with 400 µl of ether, and the ether fractions from the three A/M washes pooled. The E extracts described above were washed once with 404 µl of water and pooled with the A/M ether fractions. The pooled ether fractions were blown down to a volume of approximately 300 µl with nitrogen gas and filtered using a syringe microfilter. The sample vials were rinsed with approximately 100 µl ether and the rinse was similarly filtered and pooled with the initial filtrate, yielding total volume of approximately 150 µ. A 50 µl aliquot was stored at −20° C. until further analysis and the remaining 100 µl sample was saponified as follows. 100 µl of 10% potassium hydroxide (KOH) in methanol was added to each 100 µl sample and the mixture stored in the dark at room temperature for approximately 2 hours. 400 µl of water was then added to the samples and the ether phase removed. For better phase separation, saturated NaCl may be substituted, for the water. The water solution was then extracted twice more with 100 µl of ether and the ether samples pooled and washed with water.

The saponified samples were then analyzed by HPLC analysis on a Rainin microsorb C18 column (25 cm length, 4.6 mm outside diameter) at a, flow rate of 1.5 ml per minute. The gradient used for elution is as follows:

A=acetonitrile

B=hexane/methylene chloride (1:1)

C=methanol.

The initial solution was 70:20:10 (A:B:C). At 2.5 minutes the solution is ramped over minutes to 65:25:10 (A:B:C) and held at this for 12.5 minutes. The solution is then ramped to 70:20:10 (A:B:C) over two minutes followed by a three minute delay prior to injection of the next sample. The absorbance of the eluting samples is continuously monitored at 450 and 280 nm and known chemical and biological standards were used to identify the various absorbance peaks.

Figure 4:
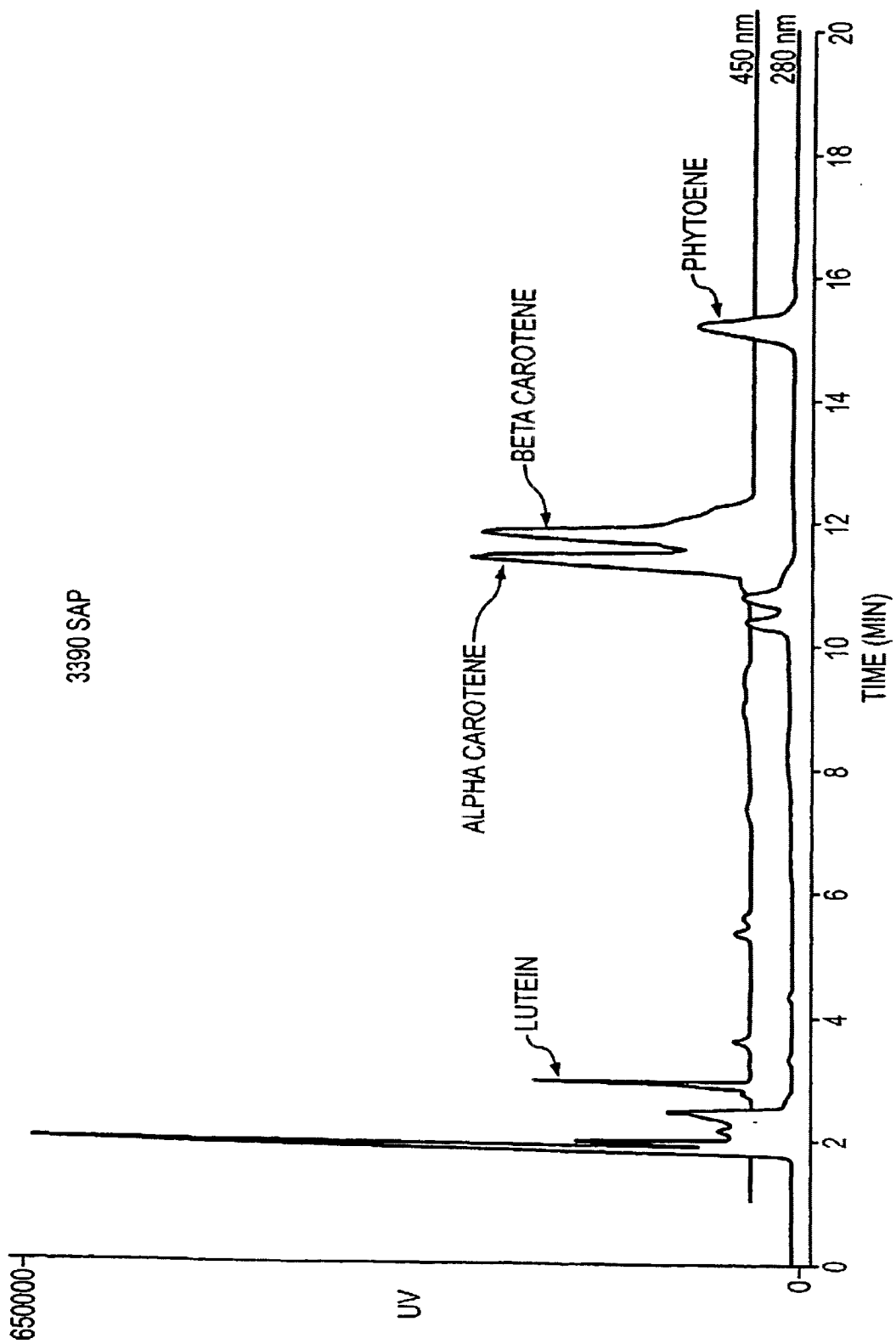
FIG. 4 shows the results of analyses of saponified samples for pCGN3390 transformed seeds.

In FIGS. 3 and 4, results of analyses of saponified samples are provided for control and pCGN3390 transformed seeds, respectively. Clear increases in the levels of α- and β-carotene and phytoene in the transagenic plant seeds are observed, as well as smaller increases in levels of the hydroxylated carotenoid, lutein.

C. Carotenoid and Tocopherol Analysis of Mature Seeds from crtB Transgenic Plants Mature 3390 T2 seed were sent to an analytical laboratory for quantitative analysis using standard HPLC methods known in the art. These results of these analysis are shown in Table 4 below. Compound levels are presented as µg/g.

Seeds designated "Maroon" were selected based on seed color. The seeds which have orange embryos appear maroon colored at maturity as opposed to the black-brown appearance of seeds from wild type plants of this cultivar. Seeds designated as "Random" were not selected for color. As 3390-1 is segregating 3 to 1 for Kan, the "Random" population includes a proportion of nulls. The maroon population contains only transgenics. Due to an effort to exclude nulls from this population, the inclusion of homozygotes may be favored.

TABLE 4

| COMPOUND | CONTROL | 3390-1 RANDOM | 3390-1 MAROON |
|---|---|---|---|
| Lutein | 7.2 | 18 | 26 |
| Zeaxanthin | nd* | nd | nd |
| α-cryptoxanthin | nd | 8 | 15 |
| β-cryptoxanthin | nd | nd | nd |
| Lycopene | nd | 2.3 | 5.1 |
| cis-Lycopene | nd | 2.9 | 5.4 |
| α-carotene | 0.6 | 124 | 244 |
| β-carotene | 0.9 | 177 | 338 |
| cis-β-carotene | 0.2 | 12 | 26 |
| Other | 6 | 34 | 51 |
| Total colored carotenoids | 14.9 | 378.2 | 710.5 |
| Phytoene | nd | 62 | 139 |
| Phytofluene | nd | 24 | 54 |
| Total all carotenoids | 14.9 | 464.2 | 903.5 |
| Alpha-tocopherol | 74 | 93 | 109 |
| Gamma-tocopherol | 246 | 188 | 95 |
| Delta-tocopherol | 3 | 5 | 5 |

*nd = not detected

In the non-transgenic sample, "other" includes mostly very polar compounds, such as neoxanthin, violaxanthin, etc. In the transgenic sample "other" includes these and additional compounds, such as zeta β-carotene, neurosporene, and mono-cyclic carotenoids.

Results of carotenoid analysis of 3390 T2 seeds from transformed plants of B. napus variety Quantum (SP30021) are presented in FIGS. 12A and 12B.

Results of carotenoid analysis of 3390 T3 seeds from transformed plants of B. napus variety 212/86 (SP001) are presented in FIG. 13.

The above results demonstrate that α- and β-carotenes levels are significantly increased in the mature seeds as the result of expression of the crtB gene. Generally, the overall increase in carotenoids is quite high, nearly 50 fold for colored carotenoids and up to 60 fold if phytoene and phytofluene are included. It is clear that the flux through the isoprenoid pathway has been dramatically increased. Additionally it is noted that the α-tocopherol (Vitamin E) levels are also increased by nearly 50%.

D. Germination Studies

Ten mature seeds of 3390-1 and seeds of 212/86 control were planted in soil and grown in a walk-in growth chamber. The transgenics emerged 1 to 2 days later than the controls, however, all seeds did germinate. The transgenics were yellowish-pink when they first emerged but greened up in one to two days. At the emergence of the first true leaf, no difference in color was observed. Plants germinated from both the transgenic and control seeds developed normally.

E. Fatty Acid Analysis

Fatty acid composition of mature seeds was determined by GC analysis of single T2 seeds harvested from trangenic plants 3390-1 and 3390-8. Single seeds from both Random (R) and Maroon (M) populations (as defined above) were analyzed and compared to seeds from a 212/86 control (SP001-1). The results of these analyses are provided in Table 5 below as weight % total fatty acids.

TABLE 5

FATTY ACID COMPOSITION OF 3390-1 AND 3390-8 LINES

| SAMPLE | 10:0 | 12:0 | 14:0 | 16:0 | 16:1 | 18:0 | 18:1 | 18:2 | 18:3 | 20:0 | 20:1 | 20:2 | 22:0 |
|---|---|---|---|---|---|---|---|---|---|---|---|---|---|
| CONTROL | 1.5 | 0 | 0.1 | 5.1 | 0.4 | 1.7 | 59.9 | 17.1 | 12.0 | 0.6 | 1.2 | 0.1 | 0.3 |
| CONTROL | 1.8 | 0 | 0.1 | 5.1 | 0.4 | 1.7 | 60.1 | 16.6 | 12.1 | 0.6 | 1.2 | 0.1 | 0.3 |
| CONTROL | 2.0 | 0 | 0.1 | 5.0 | 0.4 | 1.6 | 60.5 | 16.2 | 12.0 | 0.6 | 1.2 | 0.1 | 0.3 |
| CONTROL | 2.2 | 0 | 0.1 | 5.2 | 0.4 | 1.6 | 57.2 | 18.2 | 12.7 | 0.6 | 1.3 | 0.1 | 0.4 |
| CONTROL | 1.6 | 0 | 0.1 | 4.7 | 0.4 | 1.8 | 62.7 | 15.3 | 11.3 | 0.6 | 1.2 | 0.1 | 0.3 |
| 3390-1-R | 2.8 | 0 | 0.1 | 4.8 | 0.5 | 3.6 | 69.9 | 10.6 | 4.8 | 1.2 | 1.1 | 0.0 | 0.6 |
| 3390-1-R* | 1.5 | 0 | 0.1 | 4.7 | 0.3 | 1.5 | 58.1 | 19.3 | 12.3 | 0.5 | 1.2 | 0.1 | 0.3 |
| 3390-1-R | 3.5 | 0 | 0.1 | 4.2 | 0.3 | 2.6 | 71.1 | 9.6 | 5.8 | 1.0 | 1.2 | 0.0 | 0.6 |
| 3390-1-R* | 1.5 | 0 | 0.1 | 4.7 | 0.3 | 1.9 | 61.0 | 17.8 | 10.4 | 0.7 | 1.3 | 0.1 | 0.3 |
| 3390-1-R | 2.2 | 0 | 0.1 | 4.4 | 0.3 | 3.1 | 73.6 | 8.9 | 4.4 | 1.2 | 1.1 | 0.0 | 0.7 |
| 3390-1-R | 1.9 | 0 | 0.1 | 4.5 | 0.3 | 2.4 | 72.7 | 10.6 | 4.7 | 0.9 | 1.3 | 0.1 | 0.6 |
| 3390-1-R | 2.5 | 0 | 0.1 | 4.2 | 0.3 | 3.4 | 71.7 | 10.0 | 5.1 | 1.1 | 1.0 | 0.0 | 0.6 |
| 3390-1-R | 1.7 | 0 | 0.1 | 4.4 | 0.3 | 2.6 | 73.5 | 10.0 | 4.5 | 1.0 | 1.2 | 0.1 | 0.6 |
| 3390-1-R | 1.9 | 0 | 0.1 | 4.2 | 0.3 | 2.3 | 72.4 | 9.9 | 6.3 | 0.9 | 1.2 | 0.1 | 0.5 |
| 3390-1-R | 2.5 | 0 | 0.1 | 4.2 | 0.3 | 2.7 | 72.0 | 10.1 | 5.1 | 1.0 | 1.2 | 0.1 | 0.6 |
| 3390-1-R* | 1.5 | 0 | 0.1 | 4.7 | 0.3 | 1.7 | 58.5 | 18.5 | 12.6 | 0.6 | 1.2 | 0.1 | 0.3 |
| 3390-1-R | 2.8 | 0 | 0.1 | 4.6 | 0.4 | 3.7 | 71.8 | 9.1 | 4.2 | 1.3 | 1.2 | 0.0 | 0.7 |
| 3390-1-R | 1.8 | 0 | 0.1 | 4.0 | 0.3 | 2.3 | 72.4 | 11.1 | 5.2 | 0.9 | 1.3 | 0.1 | 0.5 |
| 3390-1-R | 1.7 | 0 | 0.1 | 4.4 | 0.3 | 2.7 | 73.9 | 9.9 | 4.2 | 1.0 | 1.2 | 0.1 | 0.6 |
| 3390-1-R | 1.7 | 0 | 0.1 | 4.6 | 0.4 | 2.6 | 71.4 | 10.9 | 5.5 | 1.0 | 1.3 | 0.1 | 0.6 |
| 3390-1-R | 2.7 | 0 | 0.1 | 4.2 | 0.3 | 2.8 | 72.1 | 9.9 | 5.0 | 1.1 | 1.3 | 0.0 | 0.6 |
| 3390-1-R | 2.0 | 0 | 0.1 | 4.5 | 0.3 | 3.0 | 72.5 | 9.7 | 4.6 | 1.2 | 1.3 | 0.1 | 0.7 |
| 3390-1-R | 1.8 | 0 | 0.1 | 4.9 | 0.4 | 3.4 | 71.8 | 10.4 | 4.2 | 1.2 | 1.2 | 0.0 | 0.7 |
| 3390-1-R* | 0.9 | 0 | 0.1 | 4.5 | 0.3 | 1.7 | 55.9 | 18.8 | 15.6 | 0.5 | 1.3 | 0.1 | 0.3 |
| 3390-1-R* | 1.4 | 0 | 0.1 | 4.8 | 0.4 | 1.7 | 57.1 | 18.0 | 14.4 | 0.6 | 1.2 | 0.1 | 0.3 |
| 3390-1-R* | 1.4 | 0 | 0.1 | 4.5 | 0.3 | 1.7 | 57.8 | 18.5 | 13.5 | 0.6 | 1.3 | 0.1 | 0.3 |
| 3390-1-R | 2.2 | 0 | 0.1 | 4.5 | 0.3 | 2.5 | 73.4 | 9.7 | 4.6 | 0.9 | 1.2 | 0.0 | 0.5 |
| 3390-1-R | 1.5 | 0 | 0.1 | 3.8 | 0.3 | 2.7 | 75.9 | 8.1 | 4.6 | 1.0 | 1.4 | 0.0 | 0.6 |
| 3390-1-R | 1.6 | 0 | 0.1 | 4.5 | 0.3 | 2.6 | 71.9 | 10.6 | 5.5 | 1.0 | 1.3 | 0.1 | 0.6 |
| 3390-1-R* | 1.3 | 0 | 0.1 | 6.2 | 0.5 | 1.4 | 53.6 | 21.7 | 13.2 | 0.5 | 1.1 | 0.1 | 0.3 |
| 3390-1-R | 2.1 | 0 | 0.1 | 4.3 | 0.3 | 2.4 | 72.3 | 10.7 | 5.1 | 0.9 | 1.2 | 0.0 | 0.6 |
| 3390-1-R* | 1.3 | 0 | 0.1 | 5.0 | 0.3 | 1.6 | 57.8 | 18.8 | 13.0 | 0.5 | 1.3 | 0.1 | 0.3 |
| 3390-1-R | 2.1 | 0 | 0.1 | 4.4 | 0.3 | 3.3 | 72.7 | 9.2 | 4.8 | 1.2 | 1.2 | 0.0 | 0.7 |
| 3390-1-R | 1.5 | 0 | 0.1 | 4.5 | 0.3 | 3.3 | 72.6 | 10.1 | 4.6 | 1.2 | 1.1 | 0.1 | 0.7 |
| 3390-1-R* | 1.2 | 0 | 0.1 | 4.7 | 0.3 | 1.9 | 59.9 | 17.1 | 12.6 | 0.6 | 1.3 | 0.1 | 0.4 |

TABLE 5-continued

FATTY ACID COMPOSITION OF 3390-1 AND 3390-8 LINES

| SAMPLE | 10:0 | 12:0 | 14:0 | 16:0 | 16:1 | 18:0 | 18:1 | 18:2 | 18:3 | 20:0 | 20:1 | 20:2 | 22:0 |
|---|---|---|---|---|---|---|---|---|---|---|---|---|---|
| 3390-1-M | 2.8 | 0 | 0.1 | 4.0 | 0.3 | 2.8 | 69.8 | 10.6 | 7.1 | 0.9 | 1.2 | 0.0 | 0.4 |
| 3390-1-M | 2.0 | 0 | 0.1 | 4.9 | 0.4 | 3.3 | 70.3 | 11.1 | 4.9 | 1.2 | 1.2 | 0.1 | 0.7 |
| 3390-1-M | 1.5 | 0 | 0.1 | 4.4 | 0.3 | 3.2 | 73.4 | 9.5 | 4.3 | 1.3 | 1.3 | 0.0 | 0.8 |
| 3390-1-M | 1.5 | 0 | 0.1 | 4.5 | 0.3 | 2.8 | 72.7 | 10.0 | 5.1 | 1.1 | 1.3 | 0.0 | 0.7 |
| 3390-1-M | 1.8 | 0 | 0.1 | 4.2 | 0.3 | 3.1 | 73.5 | 9.6 | 4.7 | 1.1 | 1.2 | 0.0 | 0.6 |
| 3390-1-M | 1.5 | 0 | 0.1 | 4.7 | 0.3 | 2.9 | 71.6 | 10.7 | 5.1 | 1.1 | 1.2 | 0.1 | 0.7 |
| 3390-1-M | 1.5 | 0 | 0.1 | 4.5 | 0.3 | 3.2 | 72.6 | 10.2 | 4.3 | 1.2 | 1.3 | 0.0 | 0.8 |
| 3390-1-M | 1.8 | 0 | 0.1 | 4.4 | 0.3 | 2.9 | 72.0 | 10.4 | 5.2 | 1.1 | 1.2 | 0.1 | 0.6 |
| 3390-1-M | 1.5 | 0 | 0.1 | 4.4 | 0.3 | 2.6 | 73.6 | 10.0 | 4.5 | 1.1 | 1.2 | 0.1 | 0.7 |
| 3390-1-M | 2.3 | 0 | 0.1 | 4.3 | 0.3 | 3.0 | 73.0 | 9.7 | 4.5 | 1.1 | 1.2 | 0.0 | 0.6 |
| 3390-8-R* | 1.0 | 0 | 0.1 | 4.9 | 0.3 | 1.6 | 59.2 | 18.9 | 11.9 | 0.5 | 1.2 | 0.1 | 0.3 |
| 3390-8-R | 2.1 | 0 | 0.1 | 4.2 | 0.3 | 2.7 | 71.9 | 10.2 | 5.6 | 1.0 | 1.2 | 0.1 | 0.6 |
| 3390-8-R | 1.5 | 0 | 0.1 | 4.4 | 0.3 | 2.3 | 72.5 | 10.4 | 5.7 | 0.9 | 1.4 | 0.1 | 0.6 |
| 3390-8-R* | 1.2 | 0 | 0.1 | 4.9 | 0.3 | 1.7 | 59.7 | 18.2 | 11.6 | 0.6 | 1.3 | 0.1 | 0.4 |
| 3390-8-R* | 1.5 | 0 | 0.1 | 4.7 | 0.3 | 1.6 | 58.7 | 18.5 | 12.2 | 0.6 | 1.3 | 0.1 | 0.4 |
| 3390-8-R | 1.8 | 0 | 0.1 | 4.2 | 0.3 | 2.9 | 73.4 | 9.2 | 5.2 | 1.1 | 1.3 | 0.0 | 0.6 |
| 3390-8-R* | 1.1 | 0 | 0.1 | 4.7 | 0.3 | 1.5 | 56.9 | 19.3 | 14.1 | 0.5 | 1.1 | 0.1 | 0.2 |
| 3390-8-R | 2.2 | 0 | 0.1 | 4.6 | 0.3 | 3.0 | 71.4 | 10.0 | 5.2 | 1.1 | 1.2 | 0.1 | 0.7 |
| 3390-8-R | 1.7 | 0 | 0.1 | 4.6 | 0.4 | 2.4 | 72.5 | 11.0 | 4.8 | 0.9 | 1.3 | 0.1 | 0.5 |
| 3390-8-R | 2.4 | 0 | 0.1 | 4.7 | 0.3 | 2.9 | 74.0 | 8.4 | 4.0 | 1.1 | 1.2 | 0.0 | 0.7 |
| 3390-8-R | 1.9 | 0 | 0.1 | 4.6 | 0.4 | 3.0 | 72.7 | 9.7 | 4.8 | 1.0 | 1.2 | 0.0 | 0.6 |
| 3390-8-R | 2.0 | 0 | 0.1 | 4.4 | 0.3 | 2.8 | 73.2 | 9.7 | 4.5 | 1.0 | 1.3 | 0.0 | 0.6 |
| 3390-8-R | 1.5 | 0 | 0.1 | 4.3 | 0.3 | 2.6 | 71.8 | 10.7 | 5.8 | 1.0 | 1.3 | 0.1 | 0.6 |
| 3390-8-R | 1.5 | 0 | 0.1 | 4.4 | 0.3 | 2.7 | 72.6 | 10.5 | 4.9 | 1.0 | 1.3 | 0.1 | 0.6 |
| 3390-8-R | 2.0 | 0 | 0.1 | 4.9 | 0.4 | 3.3 | 71.1 | 10.4 | 4.9 | 1.1 | 1.1 | 0.1 | 0.6 |
| 3390-8-R | 2.1 | 0 | 0.0 | 4.5 | 0.4 | 3.6 | 73.0 | 8.8 | 4.3 | 1.3 | 1.2 | 0.0 | 0.7 |
| 3390-8-R | 2.2 | 0 | 0.1 | 5.1 | 0.4 | 2.9 | 67.6 | 12.3 | 6.5 | 1.1 | 1.2 | 0.1 | 0.7 |
| 3390-8-R | 1.8 | 0 | 0.1 | 4.2 | 0.3 | 2.6 | 73.5 | 9.9 | 4.8 | 1.0 | 1.3 | 0.1 | 0.6 |
| 3390-8-R | 1.7 | 0 | 0.1 | 4.7 | 0.3 | 3.0 | 72.5 | 9.9 | 4.6 | 1.2 | 1.3 | 0.1 | 0.7 |
| 3390-8-R | 1.7 | 0 | 0.1 | 4.6 | 0.4 | 2.8 | 73.7 | 9.5 | 4.1 | 1.1 | 1.3 | 0.1 | 0.7 |
| 3390-8-R | 1.5 | 0 | 0.1 | 4.5 | 0.3 | 3.0 | 74.7 | 8.5 | 4.2 | 1.2 | 1.2 | 0.0 | 0.7 |
| 3390-8-R | 1.5 | 0 | 0.1 | 4.4 | 0.4 | 1.9 | 70.0 | 11.8 | 7.2 | 0.8 | 1.4 | 0.1 | 0.5 |
| 3390-8-R | 1.7 | 0 | 0.1 | 4.4 | 0.3 | 2.5 | 71.8 | 11.1 | 5.2 | 1.0 | 1.3 | 0.1 | 0.6 |
| 3390-8-R | 1.4 | 0 | 0.1 | 4.5 | 0.4 | 2.8 | 73.3 | 9.7 | 4.9 | 1.1 | 1.2 | 0.1 | 0.6 |
| 3390-8-R | 1.5 | 0 | 0.1 | 4.8 | 0.4 | 3.0 | 72.6 | 10.6 | 4.1 | 1.1 | 1.2 | 0.1 | 0.7 |
| 3390-8-R* | 1.4 | 0 | 0.1 | 5.8 | 0.4 | 2.9 | 54.0 | 20.0 | 13.0 | 0.8 | 1.1 | 0.1 | 0.4 |
| 3390-8-R | 1.4 | 0 | 0.1 | 4.4 | 0.3 | 2.7 | 71.2 | 10.8 | 6.0 | 1.0 | 1.3 | 0.1 | 0.6 |
| 3390-8-R | 1.7 | 0 | 0.1 | 4.6 | 0.4 | 2.8 | 72.6 | 10.0 | 5.1 | 1.0 | 1.2 | 0.1 | 0.6 |
| 3390-8-R* | 1.0 | 0 | 0.1 | 4.6 | 0.3 | 1.6 | 59.6 | 18.5 | 12.3 | 0.5 | 1.2 | 0.1 | 0.3 |
| 3390-8-R* | 1.1 | 0 | 0.1 | 4.6 | 0.3 | 1.4 | 56.5 | 20.4 | 13.4 | 0.5 | 1.3 | 0.1 | 0.3 |
| 3390-8-M | 1.8 | 0 | 0.1 | 4.7 | 0.4 | 3.3 | 70.1 | 11.1 | 5.5 | 1.2 | 1.1 | 0.1 | 0.7 |
| 3390-8-M | 1.5 | 0 | 0.1 | 4.3 | 0.3 | 3.0 | 73.0 | 10.3 | 4.3 | 1.1 | 1.2 | 0.1 | 0.7 |
| 3390-8-M | 1.9 | 0 | 0.1 | 4.5 | 0.4 | 3.7 | 73.1 | 8.9 | 4.2 | 1.3 | 1.2 | 0.0 | 0.7 |
| 3390-8-M | 1.6 | 0 | 0.1 | 4.4 | 0.3 | 2.5 | 73.4 | 9.7 | 5.1 | 1.0 | 1.3 | 0.1 | 0.7 |
| 3390-8-M | 1.3 | 0 | 0.1 | 4.4 | 0.3 | 3.0 | 73.7 | 9.6 | 4.4 | 1.1 | 1.3 | 0.0 | 0.7 |
| 3390-8-M | 2.1 | 0 | 0.1 | 4.3 | 0.3 | 3.2 | 74.0 | 8.9 | 4.1 | 1.2 | 1.2 | 0.1 | 0.6 |
| 3390-8-M | 2.1 | 0 | 0.1 | 3.9 | 0.3 | 1.6 | 71.6 | 11.9 | 5.7 | 0.7 | 1.5 | 0.1 | 0.5 |
| 3390-8-M | 1.6 | 0 | 0.1 | 4.6 | 0.3 | 2.8 | 71.0 | 11.8 | 4.8 | 1.0 | 1.3 | 0.1 | 0.6 |
| 3390-8-M | 2.1 | 0 | 0.1 | 4.8 | 0.4 | 3.2 | 70.3 | 10.7 | 5.2 | 1.2 | 1.2 | 0.1 | 0.7 |
| 3390-8-M | 1.6 | 0 | 0.1 | 4.5 | 0.3 | 2.9 | 72.7 | 9.9 | 4.8 | 1.1 | 1.3 | 0.0 | 0.7 |

The above data demonstrate a substantial increase in oleic acid (18:1) in seeds from each of the transgenic lines. The increase in oleic acid is at the expense of linoleic and linolenic acids, both of which were decreased in the transgenic lines. Increases in 18:0 and 20:0 fatty acids were also observed. Based on these data, the null seeds present in the Random population can be identified, and are marked on Table with an asterisk (*). All of the seeds in the Maroon populations from each transgenic line have the observed altered fatty acid composition, confirming that the altered fatty acid composition is the result of expression of the crtB gene.

Figure 5:
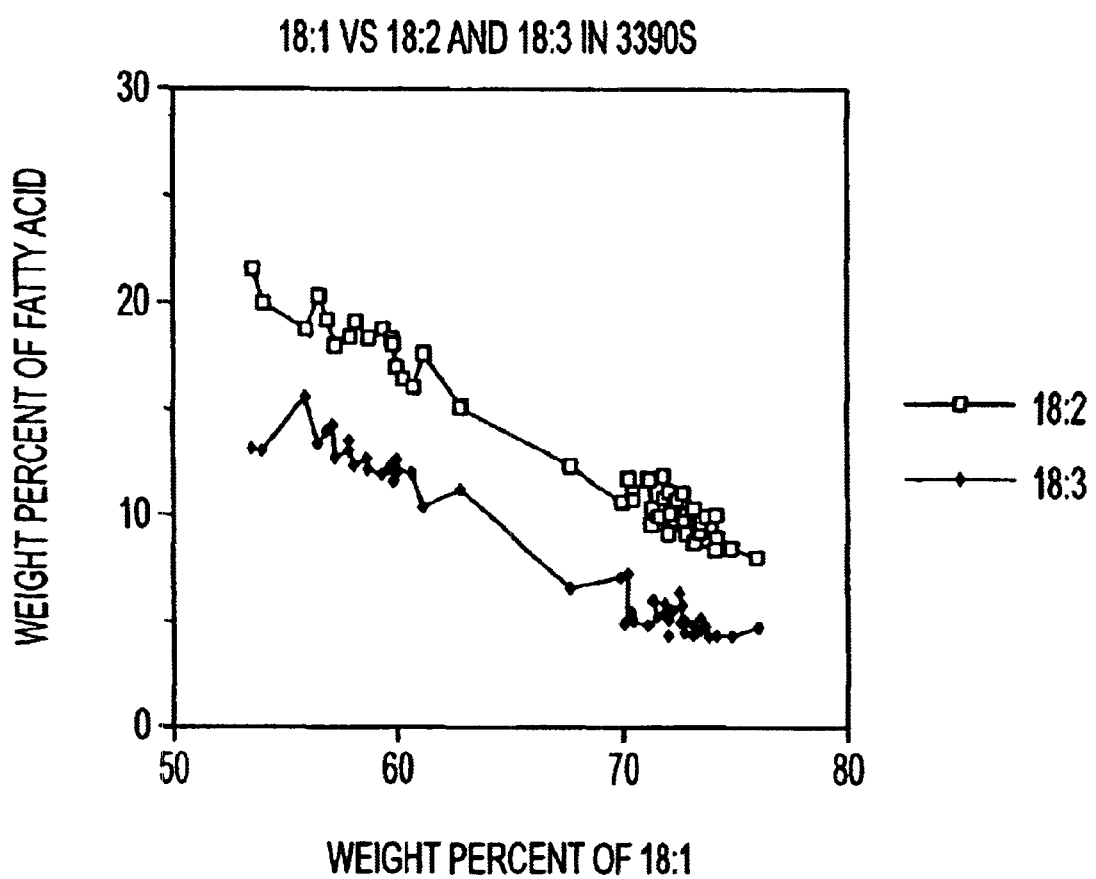
FIG. 5 shows a graph of the fatty acid analysis in pCGN3390 transformed seeds and demonstrates that the increase in 18:1 fatty acids correlates with a decrease in 18:2 and 18:3.
Figure 6:
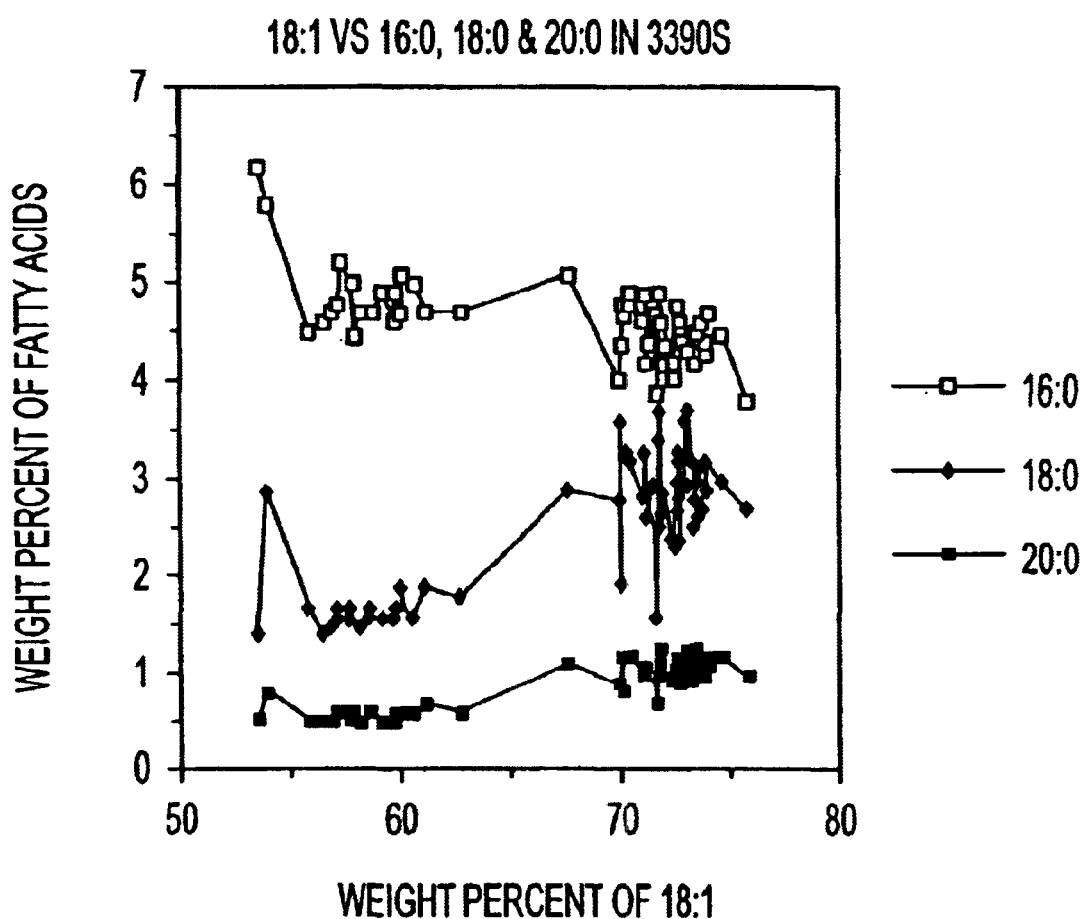
FIG. 6 shows a graph of the fatty acid analysis in pCGN3390 transformed seeds and demonstrates that the increase in 18:1 correlates with an increase in both 18:0 and 20:0, but little effect is seen in 16:0.
Figure 7:
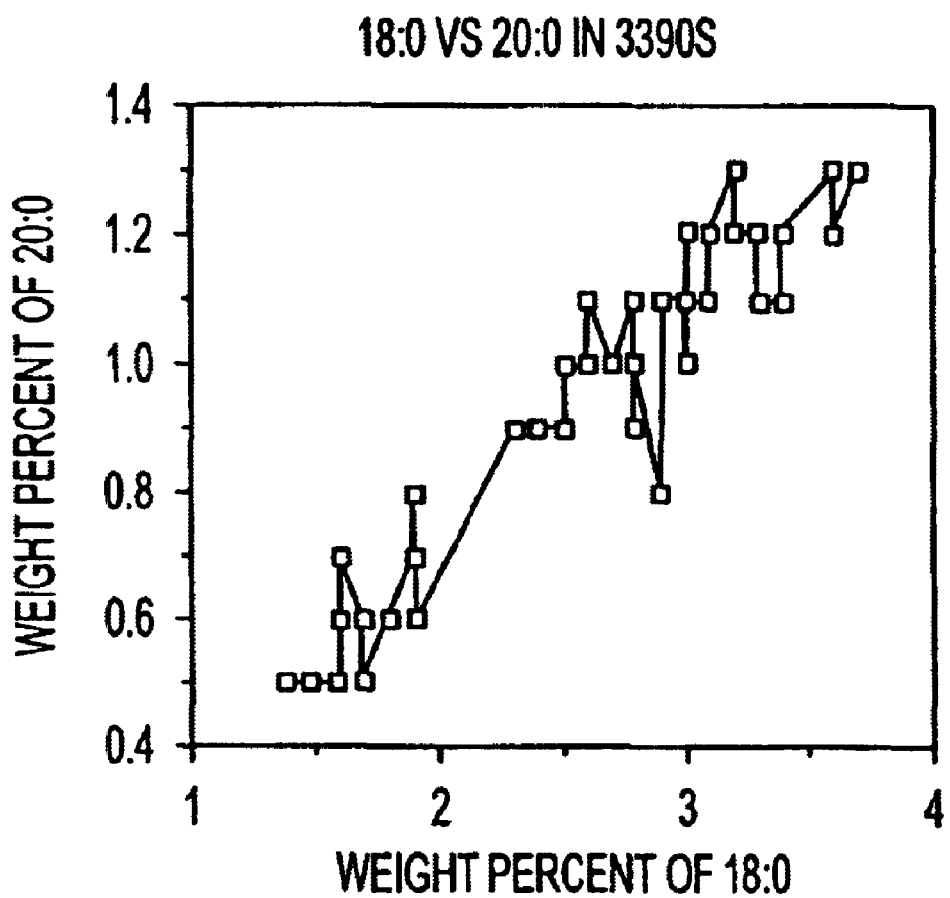
FIG. 7 shows a graph of the fatty acid analysis in pCGN3390 transformed seeds and demonstrates the increase in 18:0 correlates well with an increase in 20:0.
Figure 8:
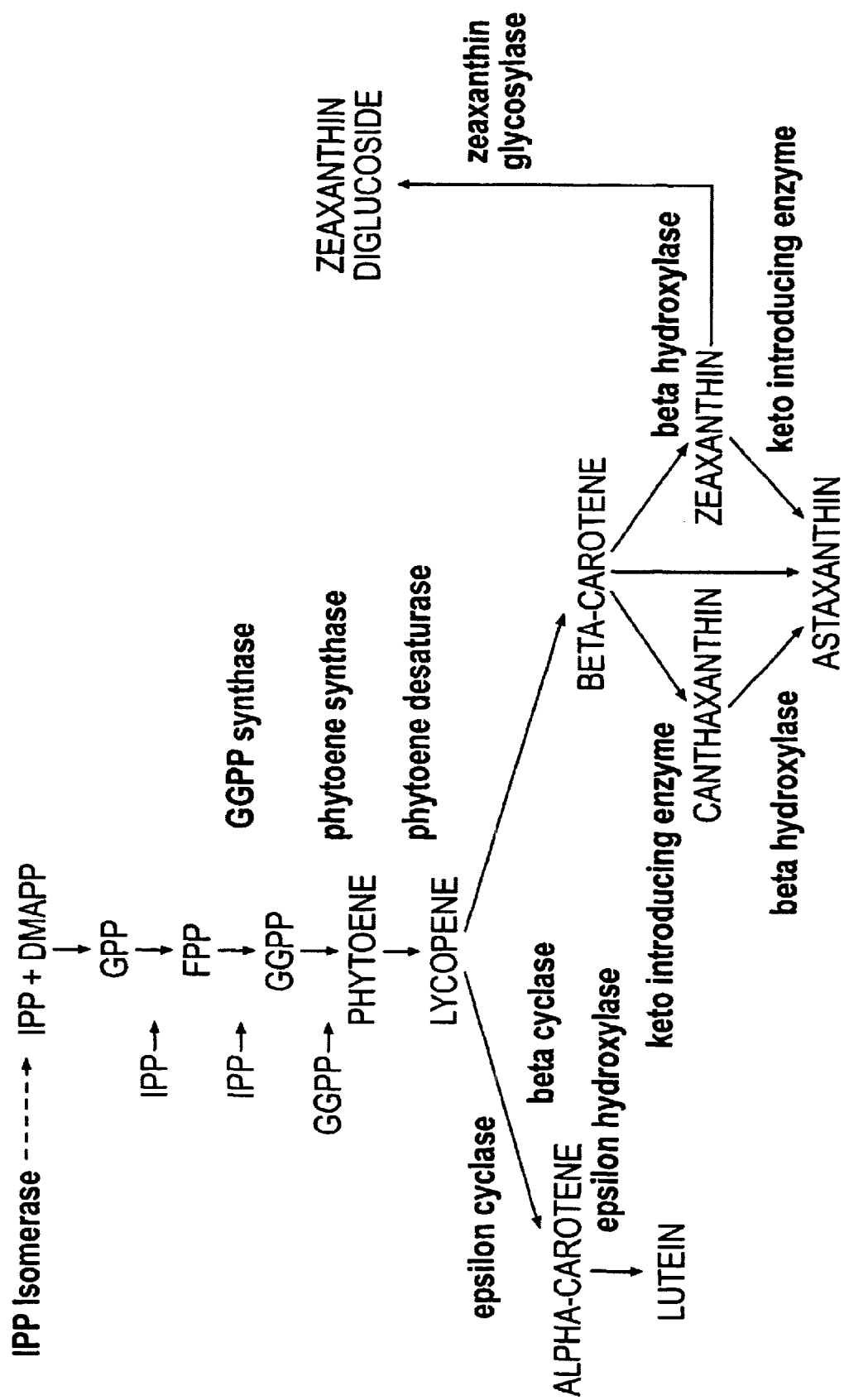
FIG. 8 shows a carotenoid biosynthesis pathway.

The trends in fatty acid composition data in the transgenic seeds which indicate positive and negative correlations of fatty acid composition changes with the observed increase in 18:1 levels are provided in FIGS. 5–7. The increase in 18:1 correlate switch the decreases in 18:2 and 18:3. (FIG. 5). The increase in 18:1 also correlates with an increase in both 18:0 and 20.0, but little effect on 16:0 was seen (FIG. 6). The increase in 18:0 also correlated with an increase in 20:0 (FIG. 7).

F. Carotenoid Analysis of Mature Seeds from crtE Transgenic Plants

Carotenoids were analyzed in mature T2 seeds of 3392 *B. napus* plants tranformed to express the *E. uredovora* crtE gene. Approximately two fold increases in levels of lutein and β-carotene was observed in seeds of plant 3392-SP30021-16. Lycopene was also detected in these seeds and is undetectable in seeds of untransformed control plants. Analysis of seeds from 7 additional 3392 transformants did not reveal significant increases in the carotenoid levels.

G. Analysis of Chlorophyll and Tocopherol Levels in crtE Transgenic Plants

Chlorophyll levels were analyzed using a spectrophotometric assay (Bruinsma, J. 1961, A comment on the spectrophotometric determination of chlororphyll, Biochem Biophy Acta, 52:576–578) in mature T2 seeds of transgenic 3392 *B. napus* plants. Levels in 3392 transgenic plants were compared to seeds of transgenic *B. napus* plants expressing phytoene synthase (crtB) and to nontransformed control plants. Results are shown in Table 6 below.

TABLE 6

| Gene and sample | Pigment concentration (µg/gFW) | |
|---|---|---|
| | Total carotenoids | Total chlorophyll |
| Phytoene synthase | | |
| 27 DPA SP001 control | 53 | 676 |
| 27 DPA T4 3390-1-6 | 354 | 282 |
| 40 DPA SP001 control | 47 | 471 |
| 40 DPA T4 3390-1-6 | 534 | 179 |
| 50 DPA SP001 control | 16 | 125 |
| 50 DPA T4 3390-1-6 | 648 | 125 |
| GGPP synthase | | |
| 35 DPA SP30021 control | 68 | 407 |
| 35 DPA T2 33924 | 65 | 660 |
| 35 DPA T2 3392-16 | 73 | 648 |
| Mature SP30021 control | 21 | 35 |
| Mature T2 3392-4 | 25 | 31 |
| Mature T2 3392-16 | 50 | 60 |

Chlorophyll concentrations of the 35 DPA seeds of two lines were increased by approximately 60% compared to the levels of the control plant. The initial results demonstrate that the GGPP synthase gene increased the GGPP substrate availability for chlorophyll biosynthesis during seed development. Mature seeds of the 3392-16 line had higher chlorophyll and carotenoid concentrations than those of the control.

H. Carotenoid Analysis of Mature Seeds from crtI Transgenic Plants.

Carotenoids were analyzed in mature T2 seeds of 901*B. napus* plants tranformed to express the antisense lycopene ε-cyclase gene. Seeds of nine transgenic plants were analyzed for carotenoid content. An approximately two fold increase in levels of lutein, β-carotene and total carotenoids was observed in seeds of one line, 9010-SP30021-10, when compared to control plants.

I. Carotenoid Analysis of Mature Seeds from crtB+crtI Transgenic Plants

Carotenoid levels of Mature 9009 T2 seeds were extracted and quantified on an HPLC as follows. Approximately 100 mg of seeds were ground in a mortar and pestle in 3 ml extraction solvent (hexane/acetone/ethanol (50/25/25 v/v) with 0.2 ml of an internal standard (5 mg/ml µ-apo-8' carotenal (dissolved in 100 µl hexane), in acetonitrile/methylene chloride/methanol:(50/40/10, v/v/)). The extraction solution was transformed to a new glass tube, and the remaining seed was again extracted with the extraction solvent and pooled with first extraction solution. The extraction was repeated until no color was visible in the extraction solution. Pooled extracts were mixed by vortexing briefly, then centrifuged for approximately 5 minutes. The resulting supernatant was transfered to a new tube and dried under nitrogen gas. The residue was resuspended in 2 ml of hexane. Potassium hydroxide, in methanol, was added to a final concentration of 5%, and the solution was incubated overnight in the dark at 4° C. Another 2 ml of hexane was then added to the solution with 1 ml of saturated sodium chloride. The solution was mixed briefly by vortexing and centrifuged for approximately 5 minutes. The upper hexane layer was removed and transfered to a new glass tube. The remaining bottom phase was again extracted with hexane and centrifuged. The upper phase was combined with the previous hexane phase. This was repeated until the hexane phase was colorless. The pooled hexane phases were dried under nitrogen gas, and the residue was dissolved in 2.0 ml of acetonitrile/methylene chloride/methanol (50/40/10 v/v). The solution was filtered through a 0.45 cm filter and colected in a brown 1050 High-Performance Liquid Chromatograph (HPLC), and isocratic separation of carotenoids was performed on a Hewlett Packard reverse phase C-18 (51) column (4.6 mm×20 cm) at 30° C. The mobile phase was acetonitrile/ methylene chloride/ methanol (80/10/10, v/v) with a flow rate of 1.0 ml/min and a sample injection volume of 20 µl (running time of 22 min). Routine detection of colored carotenoids is at 450 nm, phytoene at 280 nm, and phytofluene at 365 nm. Spectral scans for peak purity were made at 250 nm and 600 nm. Spectra of peaks at the upslope, apex, and downslope are normalized and overlaid. Superimposing spectra were taken as evidence of peak purity. The results are shown in Table 7 below. Carotenoid levels are presented as µg/gFW.

TABLE 7

| Sample ID # | Lutein | Lycopene | α-Carotene | β-Carotene | Phytoene | Total |
|---|---|---|---|---|---|---|
| SP30021 control | 36 | ND | ND | 4 | ND | 40 |
| 3390-SP001-1-6-15 (T5 Homo) | 54 | 4 | 552 | 638 | 277 | 1525 |
| 9009-SP30021-1 | 44 | 44 | 336 | 691 | 42 | 1157 |
| 9009-SP30021-6 | 53 | 87 | 689 | 1118 | 152 | 2099 |
| 9009-SP30021-9 | 48 | 34 | 487 | 798 | 194 | 1561 |
| 9009-SP30021-10 | 33 | 25 | 248 | 489 | 34 | 829 |
| 9009-SP30021-12 | 31 | ND | ND | 2 | ND | 33 |
| 9009-SP30021-14 | 42 | 37 | 404 | 791 | 81 | 1355 |
| 9009-SP30021-15 | 37 | 15 | 137 | 278 | ND | 467 |
| 9009-SP30021-16 | 50 | 38 | 428 | 828 | 65 | 1409 |

The results demonstrate that as with plants transformed to express crtB alone, plants expressing crtB and crtI contain significant increases in total carotenoid levels. Furthermore, it is apparent that expression of crtI with crtB, leads to further modification of the phytoene pools which accumulate in crtB transformants. Phytoene levels were reduced from about 20% of total carotenoids in lines transformed with crtB alone, to 4% to 7% of total carotenoids in the crtB+crtI lines. This indicates that phytoene desaturase can have a synergistic effect with phytoene synthase in increasing the metabolic flux through the carotenoid/isoprenoid pathway, and provides for even greater increases in a desired carotenoid compound, such as α-carotene and β-carotene, than is obtained by expression of crtB alone. The increased flux also appears to result in increased total carotenoid production, in addition to the composition shift from phytoene. For example, the carotenoid levels in the segregating T2 seed populations of 9009-10 are significantly higher than those detected in the 3390 homozygous seed population in 3390-1-6-15.

J. Carotenoid Analysis of Mature Seeds from crtB+ Antisense ε-Cyclase Transgenic Plants Carotenoids from mature seeds from 9002 transformants were extracted and analyzed using the method described in example 2I above. These results are shown in FIG. 14.

The initial results show a modification to the ratio of β-carotene to α-carotene. In addition, several lines show a significant reduction in lutein levels when compared to nontransgenic controls. In 9002 T2 lines, 5β-carotene to α-carotene ratios averaged 1.5, ranging from 1.1 to 2.5. For comparison, T2 3390 lines containing crtB, the ratio of β-carotene to α-carotene averaged 1.9, ranging from 1.5 to 2.4.

K. Carotenoid Analysis of Mature Seeds from crtB Transgenic Cotton Plants

Mature 3390 T2 seeds from cotton were collected and carotenoid extracts were prepared and analyzed according to the method described in 2I above. These results are shown in Table 8 below. Carotenoid levels are presented as μg/gFW.

TABLE 8

| Sample ID # | Lutein | Lycopene | α-Carotene | β-Carotene | Phytoene | Total |
|---|---|---|---|---|---|---|
| C130 control | 2 | ND | ND | ND | ND | 2 |
| 3390-C130-5-1 | 7 | ND | 4 | 86 | 420 | 517 |

An approximately 3 fold increase in lutein was observed in seeds of plant 3390-C130-5-1. Alpha β-carotene, β-carotene and phytoene were also observed in this line and are undetectable in nontransformed control plants. With β-carctenoid levels being fold higher than those of β-carotene. Total carotenoid levels were increased by more than 250 fold, with phytoene accounting for approximately 80% of that total.

EXAMPLE 3

Crosses of crtB Plants

A. Transgenic Oil Traits

To evaluate the high oleic trait of the napin-crtB transgenic plants in conjunction with expression of other oils traits, crosses off 3390-1-6-8 with a mangosteen thioesterase (5266) and a nutmeg thioesterase (3854; see WO 96/23892) were made. Crosses were also made with two low linoleic (LPOO4 and LP30108) varieties. Half-seed analyses of carotenoids and fatty acid composition were conducted on the segregating seeds, and the average of the half seed values are shown below in Tables 9 and 10.

TABLE 9

Carotenoid Levels in Half Seeds Resulting from 3390 Crosses

| Cross | Lutein | Lycopene | α-Carotene | β-Carotene | Total |
|---|---|---|---|---|---|
| F1 3390-SP001-1-6-8 × SP30021 | 21.6 | 26.2 | 271.5 | 413.1 | 732.4 |
| F1 3390-SP001-1-6-8 × 5266-SP30021-5-26 | 18.0 | 21.7 | 187.9 | 284.1 | 511.7 |
| F1 3390-SP001-1-6-8 × 5266-SP30021-35-2 | 16.2 | 22.1 | 223.0 | 318.4 | 579.7 |
| F1 3390-SP001-1-6-8 × 5266-SP30021-35-12 | 19.5 | 22.9 | 196.8 | 312.8 | 552.0 |
| F1 3390-SP001-1-6-8 × LP39108-19 | 23.7 | 22.7 | 213.4 | 355.0 | 614.8 |
| F1 LP30108-19 × F1 3390-SP001-1-6-8 | 16.4 | 19.6 | 156.7 | 224.5 | 417.2 |

TABLE 10

Fatty Acid Composition in Half Seeds Resulting from 3390 Crosses

| STRAIN_ID | % 14:0 | % 16:0 | % 18:0 | % 18:1 | % 18:2 | % 18:3 | % 20:0 |
|---|---|---|---|---|---|---|---|
| (3390-SP001-1-6-8 X SP30021) | 0.05 | 3.55 | 1.70 | 74.78 | 11.29 | 5.71 | 0.73 |
| (3390-SP001-1-6-8 X 5266-SP30021-35-12) | 0.06 | 3.84 | 11.37 | 62.86 | 11.06 | 5.08 | 3.38 |

TABLE 10-continued

Fatty Acid Composition in Half Seeds Resulting from 3390 Crosses

| STRAIN_ID | % 14:0 | % 16:0 | % 18:0 | % 18:1 | % 18:2 | % 18:3 | % 20:0 |
|---|---|---|---|---|---|---|---|
| (3390-SP001-1-6-8 X 5266-SP30021-35-2) | 0.06 | 3.68 | 11.27 | 64.80 | 9.81 | 5.16 | 3.04 |
| 3390-SPOO1-1-6-8 X 5266-SP30021-5-26 | 0.06 | 3.66 | 15.36 | 60.78 | 9.30 | 4.77 | 3.87 |
| (3390-SP001-1-6-1 X 3854-SP30021-20-3) | 2.69 | 9.80 | 3.65 | 64.62 | 9.72 | 4.57 | 1.51 |
| (3390-SP001-1-6-1 X 3854-SP30021-20-1) | 6.14 | 16.35 | 5.12 | 54.91 | 8.23 | 4.23 | 2.03 |
| (3390-SP001-1-6-1 X 5266-LP004-2-31) | 0.07 | 3.82 | 11.67 | 64.52 | 11.46 | 3.14 | 3.08 |
| (3390-SP001-1-6-8 X LP30108-19) | 0.05 | 3.80 | 1.44 | 73.66 | 14.02 | 3.93 | 0.67 |
| (LP30108-19 X 3390-SP001-1-6-8) | 0.04 | 3.31 | 1.79 | 79.69 | 9.26 | 2.97 | 0.75 |
| SPOO1-4-10 | 0.07 | 4.44 | 0.99 | 56.06 | 21.79 | 14.31 | 0.44 |
| 3390-SPOO1-1-6-8 | 0.04 | 3.46 | 1.44 | 77.26 | 9.30 | 5.71 | 0.63 |

As the above results demonstrate, a dramatic increase (100 to 200 fold) in α- and β-carotene as well as a 60 fold increase in total carotenoids May be obtained by transformation of plants for expression of an early carotenoid biosynthesis gene under the regulatory control of promoter preferentially expressed in plant seed tissue. This increase in flux primes the pathway for the production of speciality products as described above, and also results in increased production of α-tocopherol (Vitamin E).

Furthermore, it is evident that the fatty acid composition can also be altered in the transgenic plant seeds. In this manner, seeds can be used to produce novel products, to provide for production of particular carotenoids, to provide high oleic oils, and the like.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for increasing carotenoid production in seed from a host plant, said method comprising transforming said host plant with a construct comprising as operably linked components, a seed-preferred transcriptional initiation region, a nucleic acid sequence encoding a plastid transit peptide, an *Erwinia uredora* DNA coding sequence encoding phytoene synthase, and a transcriptional termination region, wherein said transformed plant produces seeds, wherein said increased carotenoid production results in an increase in total carotenoid levels in said seed as compared to native carotenoid levels in said seed.

2. The method of claim 1, wherein said method further comprises transforming said host plant with an *Erwinia uredora* DNA coding sequence encoding phytoene desaturase.

3. The method of claim 2, wherein said increased carotenoid production results in an increased ratio of α-carotene and β-carotene to phytoene.

4. The method of claim 2, wherein said transcriptional initiation region is from a gene preferentially expressed in Brassica seed tissue.

5. The method of claim 1, wherein said transcriptional initiation region is from a napin gene.

6. A method for producing a carotenoid compound in a seed, said method comprising obtaining a transformed plant which produces said seed, said plant having and expressing in its genome:

an *Erwinia uredora* DNA coding sequence encoding phytoene synthase, which is operably linked to a nucleic acid sequence encoding a plastid transit peptide and a seed-preferred transcriptional initiation region; and, an *Erwinia uredora* DNA coding sequence encoding phytoene desaturase, which is operably linked to a seed-preferred transcriptional initiation region and to a nucleic acid sequence encoding a plastid transit peptide, wherein said method results in an increase in the level of said carotenoid compound in said seed as compared to native carotenoid levels in said seed.

7. The method of claim 6, wherein said seed is Brassica.

8. The method of claim 6, wherein said transcriptional initiation region is from a gene preferentially expressed in Brassica seed tissue.

9. The method of claim 6, wherein said transcriptional initiation region is from a napin gene.

10. A transformed seed, wherein said seed was transformed with an *Erwinia uredora* DNA coding sequence encoding phytoene synthase operably linked to a seed-preferred transcriptional initiation region, and wherein said transformed seed has altered carotenoid levels as compared to native carotenoid levels in said seed.

11. The transformed seed of claim 10, wherein said seed produces increased levels of at least one carotenoid compound, said compound selected from the group consisting of α-carotene, β-carotene, lycopene, lutein, zeaxanthin, canthaxanthin, α-cryptoxanthin, β-cryptoxanthin, ζ-carotene, phytofluene, neurosporane, and astaxanthin.

12. The transformed seed of claim 11, wherein said seed produces increased levels of α- and β-carotene and lutein.

13. The transformed seed of claim 10, wherein said seed has increased levels of oleic acid and decreased levels of linoleic and/or linolenic acid.

14. A method for producing a carotenoid compound in a seed, said method comprising obtaining a transformed plant which produces said seed, said plant having and expressing in its genome:
  an *Erwinia uredora* DNA coding sequence encoding phytoene synthase which is operably linked to a nucleic acid sequence encoding a plastid transit peptide and a seed-preferred transcriptional initiation region; and,
  a *Brassica napus* lycopene ε-cyclase DNA coding sequence which is operably linked in antisense orientation to a seed-preferred transcriptional initiation region, wherein said lycopene ε-cyclase DNA coding sequence results in inhibition of a carotenoid biosynthesis gene, and wherein said method results in an increase in the level of said carotenoid compound in said seed as compared to native carotenoid levels in said seed.

15. A method for increasing carotenoid production in seed from a host plant, said method comprising transforming said host plant with a construct comprising as operably linked components, a seed-preferred transcriptional initiation region, a nucleic acid sequence encoding a plastid transit peptide, an *Erwinia uredora* DNA coding sequence encoding geranylgeranyl pyrophosphate synthase, and a transcriptional termination region, wherein said transformed plant produces seeds, wherein said increased carotenoid production results in an increase in total carotenoid levels in said seed as compared to native carotenoid levels in said seed.

16. A method for increasing carotenoid production in seed from a host plant, said method comprising transforming said host plant with a construct comprising as operably linked components, a first seed-preferred transcriptional initiation region, a nucleic acid sequence encoding a plastid transit peptide, an *Erwinia uredora* DNA coding sequence encoding phytoene synthase, a second seed-preferred transcriptional initiation region, an *Erwinia uredora* DNA coding sequence encoding phytoene desaturase, and a transcriptional termination region, wherein said transformed plant produces seeds, wherein said increased carotenoid production results in an increase in total carotenoid levels in said seed as compared to native carotenoid levels in said seed.

17. A method for increasing carotenoid production in seed from a host plant, said method comprising transforming said host plant with a construct comprising as operably linked components, a first seed-preferred transcriptional initiation region, a nucleic acid sequence encoding a plastid transit peptide, an *Erwinia uredora* DNA coding sequence encoding phytoene synthase, and a transcriptional termination region, wherein said method further comprises transforming said host plant with a second construct comprising as operably linked components a second seed-preferred transcriptional initiation region, a nucleic acid sequence encoding a plastid transit peptide, an *Erwinia uredora* DNA coding sequence encoding phytoene desaturase, and a transcriptional termination region, wherein said transformed plant produces seeds, wherein said increased carotenoid production results in an increase in total carotenoid levels in said seed as compared to native carotenoid levels in said seed.

18. A method for producing a carotenoid compound in a seed, said method comprising obtaining a transformed plant which produces said seed, said plant having and expressing in its genome:
  an *Erwinia uredora* DNA coding sequence encoding phytoene synthase, which is operably linked to a nucleic acid sequence encoding a plastid transit peptide and a seed-preferred transcriptional initiation region; and,
  wherein said method results in an increase in the level of said carotenoid compound in said seed as compared to native carotenoid levels in said seed.

19. A method for producing a carotenoid compound in a seed, said method comprising obtaining a transformed plant which produces said seed, said plant having and expressing in its genome:
  an *Erwinia uredora* DNA coding sequence encoding geranylgeranyl pyrophosphate synthase, which is operably linked to a nucleic acid sequence encoding a plastid transit peptide and a seed-preferred transcriptional initiation region; and,
  wherein said method results in an increase in the level of said carotenoid compound in said seed as compared to native carotenoid levels in said seed.

20. Seed produced by the method of any one of claims 1, 6, 14, 15, 16, 17, 18, or 19.

21. Plants produced by the method of any one of claims 1, 6, 14, 15, 16, 17, 18, or 19.

22. The method of any one of claims 1, 6, 14, 15, 16, 17, 18, or 19 wherein said seed is from a plant selected from the group consisting of oilseed Brassica, cotton, soybean, safflower, sunflower, coconut, palm, wheat, barley, rice, corn, oats, amaranth, pumpkin, squash, sesame, poppy, grape, mung beans, peanut, peas, beans, radish, alfalfa, cocoa, coffee, and tree nuts.

23. The method of claim 22, wherein said seed is from an oilseed crop plant selected from the group consisting of oilseed Brassica, cotton, soybean, safflower, sunflower, palm, coconut, and corn.

24. The method of claim 14, wherein said seed is Brassica.

25. The method of claim 14, wherein said transcriptional initiation region is from a gene preferentially expressed in Brassica seed tissue.

26. The method of claim 14, wherein said transcriptional initiation region is from a napin gene.

27. The transformed seed of claim 10, wherein said transcriptional initiation region is from a gene preferentially expressed in Brassica seed tissue.

28. The transformed seed of claim 10, wherein said transcriptional initiation region is from a napin gene.

29. The method of claim 15, wherein said transcriptional initiation region is from a gene preferentially expressed in Brassica seed tissue.

30. The method of claim 15, wherein said first transcriptional initiation region is from a napin gene.

31. The method of claim 16, wherein said transcriptional initiation region is from a gene preferentially expressed in Brassica seed tissue.

32. The method of claim 16, wherein said second transcriptional initiation region is from a gene preferentially expressed in Brassica seed tissue.

33. The method of claim 16, wherein said first transcriptional initiation region is from a napin gene.

34. The method of claim 16, wherein said second transcriptional initiation region is from a napin gene.

35. The method of claim 17, wherein said first transcriptional initiation region is from a gene preferentially expressed in Brassica seed tissue.

36. The method of claim 17, wherein said second transcriptional initiation region is from a gene preferentially expressed in Brassica seed tissue.

37. The method of claim 17, wherein said first transcriptional initiation region is from a napin gene.

38. The method of claim 17, wherein said second transcriptional initiation region is from a napin gene.

39. The method of claim 18, wherein said seed is Brassica.

40. The method of claim 18, wherein said transcriptional initiation region is from a gene preferentially expressed in Brassica seed tissue.

41. The method of claim 18, wherein said transcriptional initiation region is from a napin gene.

42. The method of claim 19, wherein said seed is Brassica.

43. The method of claim 19, wherein said transcriptional initiation region is from a gene preferentially expressed in Brassica seed tissue.

44. The method of claim 19, wherein said transcriptional initiation region is from a napin gene.

45. A transformed seed, wherein said seed was transformed with an *Erwinia uredora* DNA coding sequence encoding geranylgeranyl pyrophosphate synthase operably linked to a seed-preferred transcriptional initiation region, and wherein said transformed seed has increased carotenoid levels as compared to native carotenoid levels in said seed.

46. The transformed seed of claim 45, wherein said transcriptional initiation region is from a gene preferentially expressed in Brassica seed tissue.

47. The transformed seed of claim 45, wherein said transcriptional initiation region is from a napin gene.

48. The transformed seed of claim 45, wherein said seed produces increased levels of at least one carotenoid compound, said compound selected from the group consisting of α-carotene, β-carotene, lycopene, lutein, zeaxanthin, canthaxanthin, α-cryptoxanthin, β-cryptoxanthin, ζ-carotene, phytofluene, neurosporane, and astaxanthin.

49. A transformed seed, wherein said seed was transformed with an *Erwinia uredora* DNA coding sequence encoding phytoene synthase operably linked to a first seed-preferred transcriptional initiation region and an *Erwinia uredora* DNA coding sequence encoding phytoene desaturase operably linked to a second seed-preferred transcriptional initiation region, wherein said transformed seed has increased carotenoid levels as compared to native carotenoid levels in said seed.

50. The transformed seed of claim 49, wherein said first or second transcriptional initiation region is from a gene preferentially expressed in Brassica seed tissue.

51. The transformed seed of claim 49, wherein said first or second transcriptional initiation region is from a napin gene.

52. The transformed seed of claim 49, wherein said seed produces increased levels of at least one carotenoid compound, said compound selected from the group consisting of α-carotene, β-carotene, lycopene, lutein, zeaxanthin, canthaxanthin, α-cryptoxanthin, β-cryptoxanthin, ζ-carotene, phytofluene, neurosporane, and astaxanthin.

* * * * *

SEQUENCE LISTING

<160> NUMBER OF SEQ ID NOS: 6

<210> SEQ ID NO 1
<211> LENGTH: 1232
<212> TYPE: DNA
<213> ORGANISM: Zea mays
<220> FEATURE:
<221> NAME/KEY: misc_feature
<223> OTHER INFORMATION: Description of Artificial Sequence: ssu
      leader/crtB fusion sequence

<400> SEQUENCE: 1

```
agatctgcta gagagctttg caattcatac agaagtgaga aaaatggctt ctatgatatc      60
ctcttccgct gtgacaacag tcagccgtgc ctctaggggg caatccgccg cagtggctcc     120
attcggcggc ctcaaatcca tgactggatt cccagtgaag aaggtcaaca ctgacattac     180
ttccattaca agcaatggtg gaagagtaaa gtgcatgaat aatccgtcgt tactcaatca     240
tgcggtcgaa acgatggcag ttggctcgaa aagttttgcg acagcctcaa agttatttga     300
tgcaaaaacc cggcgcagcg tactgatgct ctacgcctgg tgccgccatt gtgacgatgt     360
tattgacgat cagacgctgg gctttcaggc ccggcagcct gccttacaaa cgcccgaaca     420
acgtctgatg caacttgaga tgaaaacgcg ccaggcctat gcaggatcgc agatgcacga     480
accggcgttt gcggcttttc aggaagtggc tatggctcat gatatcgccc cggcttacgc     540
```

-continued

| | |
|---|---|
| gtttgatcat ctggaaggct tcgccatgga tgtacgcgaa gcgcaataca gccaactgga | 600 |
| tgatacgctg cgctattgct atcacgttgc aggcgttgtc ggcttgatga tggcgcaaat | 660 |
| catgggcgtg cgggataacg ccacgctgga ccgcgcctgt gaccttgggc tggcatttca | 720 |
| gttgaccaat attgctcgcg atattgtgga cgatgcgcat gcgggccgct gttatctgcc | 780 |
| ggcaagctgg ctggagcatg aagtctgaa caaagagaat tatgcggcac tgaaaaccg | 840 |
| tcaggcgctg agccgtatcg cccgtcgttt ggtgcaggaa gcagaacctt actatttgtc | 900 |
| tgccacagcc ggcctggcag ggttgcccct gcgttccgcc tggcaatcg ctacggcgaa | 960 |
| gcaggtttac cggaaaatag gtgtcaaagt tgaacaggcc ggtcagcaag cctgggatca | 1020 |
| gcggcagtca cgaccacgc cgaaaaaatt aacgctgctg ctggccgcct ctggtcaggc | 1080 |
| ccttacttcc cggatgcggg ctcatcctcc ccgccctgcg catctctggc agcgcccgct | 1140 |
| ctagcgccat gtctttcccg gagcgtccga attatcgatg aattcgagct cggtacccgg | 1200 |
| ggatcctcta gagtcgacct gcaggcatgc aa | 1232 |

<210> SEQ ID NO 2
<211> LENGTH: 962
<212> TYPE: DNA
<213> ORGANISM: Brassica napus

<400> SEQUENCE: 2

| | |
|---|---|
| tgaattgtaa tacgactcac tatagggcga attggcccct ctagatgcat gctcgagcgg | 60 |
| ccgccagtgt gatggatatc tgcagaattc ggcttgtttg tggtcctgct ggtttagcct | 120 |
| tggctgcaga atcagcaagg ttaggtctca agttggact cattggtcct gatcttcctt | 180 |
| tcactaacaa ctacggtgtt tgggaagatg agttcaacga tcttggcttg caaaaatgta | 240 |
| ttgagcatgt ttggagagat acccttgtgt atctggacga tgacaatcct attaccattg | 300 |
| gtcgtgctta tggaagagtt agtcgacgtt tacttcacga ggagctcttg aggaggtgtg | 360 |
| tggagtcagg tgtctcgtat cttagctcca agttgagag cataacagaa gctcctgatg | 420 |
| gccttaggct tgtttcctgt gaacaaaaca cccttgttcc gtgcaggctt gccactgttg | 480 |
| cttctggagc agcttctggg aagctcttgc aatacgaagt tggagggcct agagtctgtg | 540 |
| tccaaactgc ttacggcttg gaggttgagg tggaaaagag tccatatgat ccagagcaga | 600 |
| tggtgttcat ggattacaga gattatacaa acgagaaaat ccggagctta aagctgaat | 660 |
| atccaacgtt tctctacgcc atgcctatga caaagaccag agtcttcttt gaggagacat | 720 |
| gtcttgcttc aaaagatgtc atgcccttg atttgcttaa aagaagctc ttgttgagat | 780 |
| tagagacact cggaatccga atactaaaga cttacgaaga ggaatggtct tatatcccag | 840 |
| taggtggttc cttgccaaac acggaacaaa agaatctcgc ctttggcgct gcagctagca | 900 |
| tggtacatcc cgcaacagaa gccgaattcc agcacactgg cggccgttac tagtggatcc | 960 |
| ga | 962 |

<210> SEQ ID NO 3
<211> LENGTH: 1282
<212> TYPE: DNA
<213> ORGANISM: Brassica napus

<400> SEQUENCE: 3

| | |
|---|---|
| gtgaattgta atacgactca ctatagggcg aattggccct tctagatgca tgctcgagcg | 60 |
| gccgccagtg tgatggatat ctgcagaatt cggcttgttt gtggtcctgc tggtttagcc | 120 |
| ttggcggctg aatcagctaa gttaggactt aaagttggac tgattggtcc tgaccttcct | 180 |

```
ttcactaaca actacggtgt ttgggaagat gagttcaacg atcttggctt gcaaaaatgt      240
attgagcatg tttggagaga tacccttgtg tatctggacg atgacaatcc tattaccatt      300
ggtcgtgctt atggaagagt tagtcgacgt ttacttcacg aggagttctt gaggaggtgt      360
gtggagtcag gtgtctcgta tcttagctcc aaagttgaga gcataacaga agctcctgat      420
ggccttaggc ttgtttcctg tgaacaaaac acccttgttc cgtgcaggct tgccactgtt      480
gcttctggag cagcttctgg gaagctcttg caatacgaag ttggagggcc tagagtctgt      540
gtccaaactg cttacggctt ggaggttgag gtggaaaaga gtccatatga tccagagcag      600
atggtgttca tggattacag agattataca aacgagaaaa aacgagaaaa tccggagctt      660
agaagctgaa tatccaacgt ttctctacgc catgcctatg acaaagacca gagtcttctt      720
tgaggagaca tgtcttgctt caaaagatgt catgccctt  gatttgctta aaagaagct       780
cttgttgaga ttagagacac tcggaatccg aatactaaag acttacgaag aggaatggtc      840
ttatatccca gtaggtggtt ccttgccaaa cacggaacaa agaatctcg  cctttggtgc      900
tgcagctagc atggttcatc ctgcaacagg ctattcagtt gtgagatctt tgtctgaagc      960
tccaaaatac gcatcagtca tcgctaatat actaaaacat gagaccacta cttccttcac     1020
cagacacatc aacaccaata tttcaagaca agcttgggat actttatggc caccagaaag     1080
gaaacgacag agagcattct ttctaagccg aattccagca cactggcggc cgttactagt     1140
ggatccgagc tcggtaccaa gcttggcgta atcatggtca tagctgtttc ctgtgtgaaa     1200
ttgttatccg ctcacaattc cacacaacat acgagccgga agcataaagt gtaaagcctg     1260
gggtgcctaa tgagtgagct aa                                              1282
```

<210> SEQ ID NO 4
<211> LENGTH: 1590
<212> TYPE: DNA
<213> ORGANISM: Brassica napus

<400> SEQUENCE: 4

```
gagctcggat ccactagtaa cggccgccag tgtgctggaa ttcggcttct atcttgtacc       60
aaattgttga tcatcttagc aagaggaaca gttcccttcg tcatgatctc caacctcgag      120
gtattagaag catgcgagaa gagcgacagc ccgaagaaca ccaggtccgg gagaaacagc      180
ctcgacgaca agaaaccatg ccagtaacgc ggttccaggt caagaacgc  atcaaagaac      240
ctcctagtag catccaaatc aagcttcagc aaaatatcca tcccaaaaca gaagaactcc      300
ctctgtctcc gcctctcaat aggccacaag tctctccaca cctcagccga gagctcatct      360
cctctcaagc cgttgttgtt accaccacca aggtaccgca ctatagcgtt tgcaactatc      420
ggagcagctg caagagtcct agcaaccatg taaccagtcg aaggatgaac catccccgcc      480
gtaccgccaa tgccaacaac tctttgaggc aagaccggta aggacctcc  catgggatc       540
acacaacgct cgtcttcctc aatccgcttc acgttgatcc ccaaatgttt cagcctcgca      600
accatcctct cttggatatc ttccatcttc agacccggcc tagccacaag agacgtctct      660
tcaagaaaga tcctgttgga agaaaacggc atcgcgtaca ggaacgtagg gatcttgctg      720
ttccgctctt taacctcagg gtacgcgtca agatgcttat ctctccagtc catgaacacc      780
atcttatcca catcaaacgg gtgaccatcg acctcagcaa tgataccata agctacttga      840
tacccagggt tataaggctt atcatactga accaagcatc ttgaaaaacc agtagcgtcg      900
agaacaacag aagcctgaat cttcacaccg tcactgcaga caacagtgga gttaacctcc      960
```

-continued

```
tcgtgaacca cgtcagtgac tttagcctga tggaatctaa caccgttggt gatgcacttc    1020
tgaagcatct tggatttgag ctgtttacgg ttcactctcc cgtaaggccg ggacaggtcc    1080
ttttcggagc cgtcgttgat gtagacgacg gcgccggacc aggtggtgtc gaggcagtct    1140
agcaagtcca tggcttcgaa ctcgtcaacc caaactccgt agttgttagg ccaaatgagt    1200
ttgggggaag gatcgatgga gcagacagag agtccagctt cggagacttg ctgagccacg    1260
gctaaaccag cggggccgcc gccaacgata gctagatcaa caactttgtt cagggaagtg    1320
tcgtttaaag gaaggtccaa gtcgagattc tccttcttgg tttcaggaac aagatccaaa    1380
agagcactac tagcactagt gatactacta ccgattctga ttgctctttt cttcaaacca    1440
agcttaaccc ttgaaggatt tggacttaat ctctcgaacc catgaaactg agggatgaaa    1500
aactcgagct tgttgggtgt tttcaacaga gtatccatcg aattctgcag atatccatca    1560
cactggcggc cgctcgagca tgcatctaga                                     1590
```

<210> SEQ ID NO 5
<211> LENGTH: 1645
<212> TYPE: DNA
<213> ORGANISM: Zea mays

<400> SEQUENCE: 5

```
gaattcggct cgagggcggc ggctgcgggt ggcggtggtg ggaggcggcc ccgccggtgg     60
cgccgcggcg gaggcgctgg ccaagggcgg cgtggagacg gtgctgatcg agcggaagat    120
ggacaactgc aagccctgcg gcggcgctat cccgctgtgc atggtgtcgg agttcgacct    180
gccgctcgac ctcgtggacc gcaaggtgag gaagatgaag atgatttcgc cgtccaacgt    240
cgccgtcgac atcggccgca cgctcgcgcc ccacgagtac atcgggatgg tcaggcgcga    300
ggtgctcgac gcctacctcc gctcacgggc acagtccgtc ggcgcggagg tcgtcaacgg    360
cctcttccta aggtacgagg cgcccaaaga gccgaacggc tcgtacgtgg tgcactacaa    420
ccactacgac ggcagcaacg gcaaggtcgg cggcgagaag cggtcgttcg aggtggacgc    480
gatcgtgggc gcggacggcg ccaactctcg cgtggccaac gacatgggcg cgggcgacta    540
cgagtacgcc atcgcgttcc aggagcgcgt caagatcccc gacgacaaga tggtgtacta    600
cgaggagcgc gcggagatgt acgtcggcga cgacgtctct cccgacttct acggctgggt    660
gttccccaag tgcgaccacg tcgccgtcgg caccggcacc gtcacgcaca aggccgacat    720
caagaagttt caggccgcca cgcgcctccg cgccaaggac aagattgagg cggcaagat     780 catccgcgtc gaggcgcacc ccatccccga gcaccccagg cctaagaggg tgtccgggcg    840
ggtgacgctt gtgggcgatg ccgcggggta cgtgaccaag tgctctggcg agggcatcta    900
cttcgcggcg aagagcgggc ggatgtgcgc cgaggccatc gtggcgggct ccgccaacgg    960
gacgcggatg gtgaggaga gcgacctgcg caagtacctg gccgagttcg accgcctcta    1020
ctggcccact tacaaggtgc tggacatcct gcagaaggtg ttctaccgct ccaacgcggc    1080
gcgcgaggcc ttcgtggaga tgtgcgccga cgactacgtg cagaagatga ccttcgacag    1140
ctacctctac aagcgcgtcg tgccgggcaa cccgctcgac gacatcaagc tcgccgtcaa    1200
caccatcggc agcctcgtca gggccaccgc actgcgccgg gagatggaga aggtcacctt    1260
gtgagccgcc gcccgccacg tcattgccgt cgaaatggtg tcgcagctga tcggccggtg    1320
tattagtaga gatttgcggc tgatcgggtt aatttaggcc aacatgcgtg ggcagtgggc    1380
gcggagagga agagaaacaa gttgtgcaag tgcagcaagt agatcaaaag tgctgcctgt    1440
ttgtatcgat ggatcctgca acatatagca tctggtgatg ttgagaattc ggagcagttg    1500
```

```
atcgactgga ttctgacgcc ggcaagcatc gacgtcaatg aatgtctaat acttagtaca   1560
tcaagacatg taataaaact gaaactcccc cgttctggtt caaaaaaaaa aaaaaaaaa    1620 aaaaaaaaaa aaaaagggcg gccgc                                        1645
```

```
<210> SEQ ID NO 6
<211> LENGTH: 541
<212> TYPE: PRT
<213> ORGANISM: Zea mays
<220> FEATURE:
<221> NAME/KEY: misc_feature
<222> LOCATION: (1)..(541)
<223> OTHER INFORMATION: unknown at all Xaa locations

<400> SEQUENCE: 6
```

```
Leu Arg Val Ala Val Gly Gly Gly Pro Ala Gly Gly Ala Ala Ala
1               5                   10                  15

Glu Ala Leu Ala Lys Gly Gly Val Glu Thr Val Leu Ile Glu Arg Lys
                20                  25                  30

Met Asp Asn Cys Lys Pro Cys Gly Gly Ala Ile Pro Leu Cys Met Val
            35                  40                  45

Ser Glu Phe Asp Leu Pro Leu Asp Leu Val Asp Arg Lys Val Arg Lys
50                  55                  60

Met Lys Met Ile Ser Pro Ser Asn Val Ala Val Asp Ile Gly Arg Thr
65                  70                  75                  80

Leu Ala Pro His Glu Tyr Ile Gly Met Val Arg Arg Glu Val Leu Asp
                85                  90                  95

Ala Tyr Leu Arg Ser Arg Ala Gln Ser Val Gly Ala Glu Val Val Asn
            100                 105                 110

Gly Leu Phe Leu Arg Tyr Glu Ala Pro Lys Glu Pro Asn Gly Ser Tyr
        115                 120                 125

Val Val His Tyr Asn His Tyr Asp Gly Ser Asn Gly Lys Val Gly Gly
    130                 135                 140

Glu Lys Arg Ser Phe Glu Val Asp Ala Ile Val Gly Ala Asp Gly Ala
145                 150                 155                 160

Asn Ser Arg Val Ala Asn Asp Met Gly Ala Gly Asp Tyr Glu Tyr Ala
                165                 170                 175

Ile Ala Phe Gln Glu Arg Val Lys Ile Pro Asp Asp Lys Met Val Tyr
            180                 185                 190

Tyr Glu Glu Arg Ala Glu Met Tyr Val Gly Asp Val Ser Pro Asp
        195                 200                 205

Phe Tyr Gly Trp Val Phe Pro Lys Cys Asp His Val Ala Val Gly Thr
    210                 215                 220

Gly Thr Val Thr His Lys Ala Asp Ile Lys Lys Phe Gln Ala Ala Thr
225                 230                 235                 240

Arg Leu Arg Ala Lys Asp Lys Ile Glu Gly Lys Ile Ile Arg Val
                245                 250                 255

Glu Ala His Pro Ile Pro Glu His Pro Arg Pro Lys Arg Val Ser Gly
            260                 265                 270

Arg Val Thr Leu Val Gly Asp Ala Ala Gly Tyr Val Thr Lys Cys Ser
        275                 280                 285

Gly Glu Gly Ile Tyr Phe Ala Ala Lys Ser Gly Arg Met Cys Ala Glu
    290                 295                 300

Ala Ile Val Ala Gly Ser Ala Asn Gly Thr Arg Met Val Glu Glu Ser
305                 310                 315                 320
```

-continued

```
Asp Leu Arg Lys Tyr Leu Ala Glu Phe Asp Arg Leu Tyr Trp Pro Thr
                325                 330                 335

Tyr Lys Val Leu Asp Ile Leu Gln Lys Val Phe Tyr Arg Ser Asn Ala
            340                 345                 350

Ala Arg Glu Ala Phe Val Glu Met Cys Ala Asp Asp Tyr Val Gln Lys
        355                 360                 365

Met Thr Phe Asp Ser Tyr Leu Tyr Lys Arg Val Val Pro Gly Asn Pro
    370                 375                 380

Leu Asp Asp Ile Lys Leu Ala Val Asn Thr Ile Gly Ser Leu Val Arg
385                 390                 395                 400

Ala Thr Ala Leu Arg Arg Glu Met Glu Lys Val Thr Leu Xaa Ala Ala
                405                 410                 415

Ala Arg Asp Val Ile Ala Val Glu Met Val Ser Gln Leu Ile Gly Arg
                420                 425                 430

Cys Ile Ser Arg Asp Leu Arg Leu Ile Gly Leu Ile Xaa Ala Asn Met
            435                 440                 445

Arg Gly Gln Trp Ala Arg Arg Gly Arg Glu Thr Ser Cys Ala Ser Ala
        450                 455                 460

Ala Ser Arg Ser Lys Val Leu Pro Val Cys Ile Asp Gly Ser Cys Asn
465                 470                 475                 480

Ile Xaa His Leu Val Met Leu Arg Ile Arg Ser Ser Ser Ser Thr Gly
                485                 490                 495

Phe Xaa Arg Arg Gln Ala Ser Thr Ser Met Asn Val Xaa Tyr Leu Val
            500                 505                 510

His Gln Asp Met Xaa Xaa Asn Xaa Asn Ser Pro Val Leu Val Gln Lys
        515                 520                 525

Lys Lys Lys Lys Lys Lys Lys Lys Gly Gly Arg
530                 535                 540
```